(12) United States Patent
Huang et al.

(10) Patent No.: US 8,389,768 B2
(45) Date of Patent: Mar. 5, 2013

(54) METHODS AND COMPOSITIONS COMPRISING NOVEL CATIONIC LIPIDS

(75) Inventors: Leaf Huang, Durham, NC (US); Yunching Chen, Boston, MA (US); Joyeeta Sen, West Bengal (IN); Surendar Reddy Bathula, Tarnaka Hyderabad (IN); Sumio Chono, Hokkaido (JP); Shyh-Dar Li, Toronto (CA); Michael Hackett, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 211 days.

(21) Appl. No.: 12/993,421

(22) PCT Filed: May 1, 2009

(86) PCT No.: PCT/US2009/042476
§ 371 (c)(1),
(2), (4) Date: Feb. 1, 2011

(87) PCT Pub. No.: WO2009/142892
PCT Pub. Date: Nov. 26, 2009

(65) Prior Publication Data
US 2011/0117141 A1   May 19, 2011

Related U.S. Application Data

(60) Provisional application No. 61/054,338, filed on May 19, 2008, provisional application No. 61/054,328, filed on May 19, 2008, provisional application No. 61/054,351, filed on May 19, 2008.

(51) Int. Cl.
*C07C 237/00* (2006.01)
*C07C 279/00* (2006.01)
*A61K 31/16* (2006.01)
*A61K 31/155* (2006.01)

(52) U.S. Cl. ........ 564/197; 564/176; 564/236; 564/240; 424/400; 435/458; 514/44 R; 514/44 A; 514/626; 514/634

(58) Field of Classification Search .................. 564/197, 564/236, 240; 514/626, 634
See application file for complete search history.

(56) References Cited

FOREIGN PATENT DOCUMENTS

EP 0 846 680 6/1998
WO WO2009/142893 11/2009

OTHER PUBLICATIONS

Byk et al., "Genetic Chemistry: Tools for Gene Therapy Coming from Unexpected Directions," Drug Development Research, vol. 50, No. 4/04, pp. 566-572 (Jan. 1, 2000).
International Search Report corresponding to International Application No. PCT/US2009/042476 dated Jul. 7, 2009.
Vigneron et al., "Guanidinium-Cholesterol Cationic Lipids: Efficient Vectors for the Transfection of Eukaryotic Cells," Proceedings of the National Academy of Sciences of USA, vol. 93, No. 18, pp. 9682-9686 (Sep. 3, 1996).

*Primary Examiner* — Daniel Sullivan
*Assistant Examiner* — Barbara Frazier
(74) *Attorney, Agent, or Firm* — Jenkins, Wilson, Taylor & Hunt, P.A.

(57) ABSTRACT

Provided herein are novel cationic lipids, compositions comprising the cationic lipids, and methods of using the cationic lipids. In some claims, the cationic lipids have cytotoxic activity and can be used alone or in combination with a cytotoxic bioactive compound to kill a cell. In some of these claims, the cationic lipid enhances the cytotoxic activity of the cytotoxic bioactive compound. Methods for treating a subject afflicted with a disease or unwanted condition are provided, wherein the method comprises administering a delivery system comprising a novel cationic lipid to the subject. The invention further provides methods for making delivery systems comprising the novel cationic lipids of the invention.

19 Claims, 16 Drawing Sheets

Where $R_1 = R_2 = C_{14}H_{29}$

Where $R_1 = R_2 = C_{14}H_{29}$

Scheme I

Where $R_1 = R_2 = C_{14}H_{29}$

Reagents:
(a) DCC/NHS/DCM, 0°C-rt
(b) HCOONH$_4$, 10% Pd-C, CH$_3$COOH, N$_2$ atm
(c) SC(NHBOC)$_2$, HgCl$_2$, DMF/DCM, N$_2$ atm
(d) MeI
(e) TFA/DCM, Cl ion exchange resin
(f) TFA/DCM A= Stearyl bromide, K2CO3, Ethyl acetate, 80oC B= Trifluoroacetic acid, Dichloromethane, 1N NaOH C= Tri-Boc-Arginine, EDCI, NHS, Dry Dichloromethane D= Methyl Iodide and DCM E= 3N HCl in Dioxane, Amberlyst- A 26 chloride ion-exchange resin

METHODS AND COMPOSITIONS COMPRISING NOVEL CATIONIC LIPIDS

CROSS REFERENCE TO RELATED APPLICATIONS

This application is a National Stage application under 35 U.S.C. §371 of PCT International Patent Application Serial No. PCT/US2009/042176, filed May 1, 2009, which itself claimed the benefit of U.S. Provisional Application Serial Nos. 61/054,328; 61/054,338; and 61/054,351; all filed May 19, 2008. The disclosure of each of these applications is incorporated herein by reference in its entirety.

FIELD OF THE INVENTION

The present invention relates to cationic lipids and their use as vehicles for the delivery of therapeutic agents, such as drugs into cells.

BACKGROUND OF THE INVENTION

Treatments for diseases such as cancer, for which the ultimate therapeutic goal is to kill the diseased cell or prevent or inhibit its reproduction, include the administration of cytotoxic drugs. Cytotoxic drugs include many chemotherapeutic agents that are used in the treatment of cancers, including alkylating agents, antimetabolites, and toxins. Most cytotoxic drugs are non-selective, killing healthy cells as well as diseased cells, which contributes to undesirable side effects when these agents are delivered systemically. Thus, a need exists for cytotoxic agents that are more efficacious and more selective for diseased cells over healthy cells.

BRIEF SUMMARY OF THE INVENTION

The present invention provides novel cationic lipids of Formula (I):

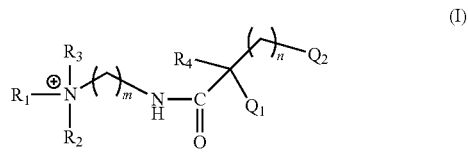

wherein:
m and n are each independently integers from 1 to 8;
$R_1$ and $R_2$ are each independently —$(CH_2)_p$—$CH_3$, wherein p is an integer from 8 to 24;
$R_3$ and $R_4$ are each independently selected from the group consisting of H, alkyl, and substituted alkyl;
$Q_1$ and $Q_2$ are selected from the group consisting of:

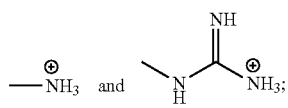

wherein at least $Q_1$ or $Q_2$ is:

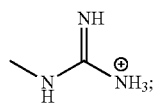

and pharmaceutically acceptable salts thereof.

Compositions comprising the novel cationic lipids and methods of using the cationic lipids of formula (I) are also presented herein. Compositions include delivery systems comprising a lipid vehicle and a bioactive compound, wherein the lipid vehicle encapsulates the bioactive compound, and wherein the lipid vehicle comprises a cationic lipid of formula (I).

The present invention also describes methods for delivering a bioactive compound to a cell using a delivery system comprising a cationic lipid of formula (I). Methods are provided for killing a cell by contacting the cell with a cytotoxic cationic lipid of formula (I) or a cytotoxic delivery system.

Further, provided herein are methods for enhancing the cytotoxic activity of a cytotoxic bioactive compound in a subject comprising administering a cytotoxic bioactive compound and a cytotoxic cationic lipid of formula (I), or administering a cytotoxic delivery system comprising a lipid vehicle comprising a cytotoxic cationic lipid of formula (I) encapsulating the cytotoxic bioactive compound.

Methods for making a delivery system and a cytotoxic delivery system comprising a lipid vehicle comprising a cationic lipid of formula (I) encapsulating a bioactive compound are also provided herein.

As such, the presently disclosed subject matter provides in some embodiments cationic lipids of Formula (I):

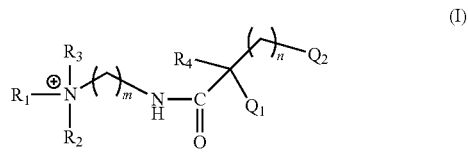

wherein m and n are each independently integers from 1 to 8; $R_1$ and $R_2$ are each independently —$(CH_2)_p$—$CH_3$, wherein p is an integer from to 24; $R_3$ and $R_4$ are each independently selected from the group consisting of H, alkyl, and substituted alkyl; $Q_1$ and $Q_2$ are selected from the group consisting of:

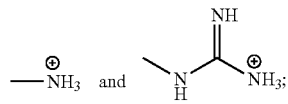

wherein at least Q1 or Q2 is:

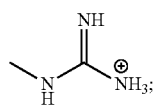

and pharmaceutically acceptable salts thereof. In some embodiments, m is 2; n is 4; p is 13; $R_3$ and $R_4$ are each methyl; and the cationic lipid of formula (I) is selected from the group consisting of:

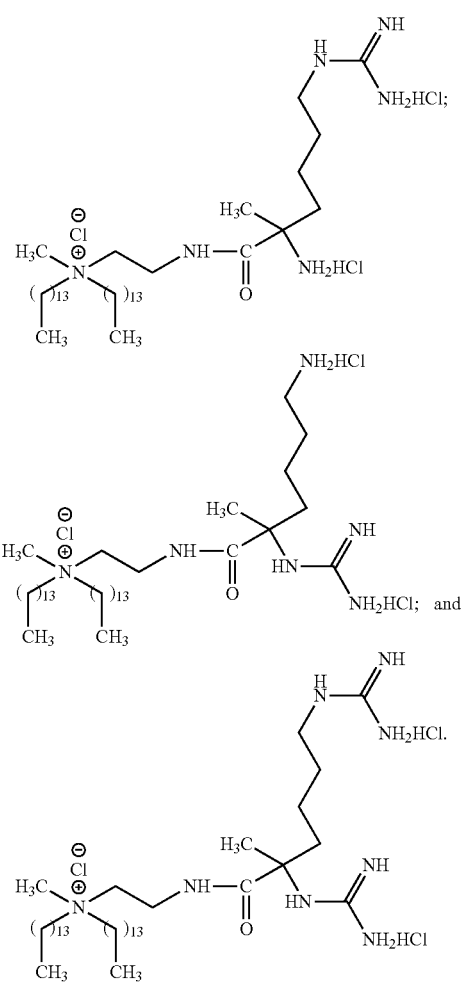

In some embodiments, m is 2; n is 3; p is 17; $R_3$ is H; $R_4$ is methyl;

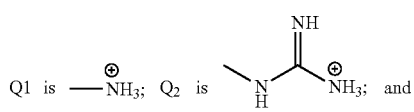

the cationic lipid of formula (I) has the following chemical structure:

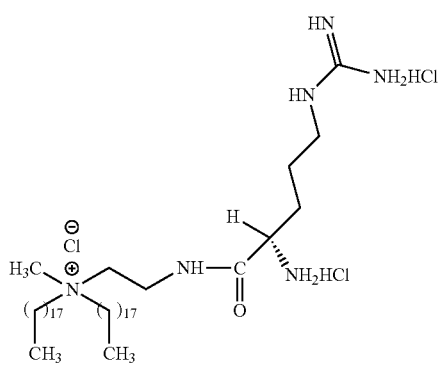

In some embodiments, m is 2; n is 4; p is 17; $R_3$ and $R_4$ are each methyl;

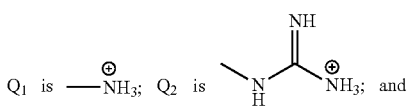

the cationic lipid of formula (I) has the following chemical structure:

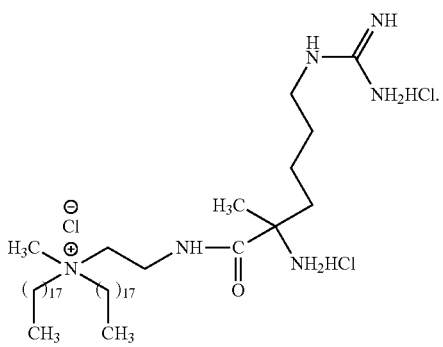

In some embodiments of the cationic lipids of the presently disclosed subject matter, said cationic lipid has cytotoxic activity.

The presently disclosed subject matter also provides in some embodiments pharmaceutical compositions comprising the cationic lipids disclosed herein and a pharmaceutically acceptable carrier.

The presently disclosed subject matter also provides in some embodiments delivery systems comprising a lipid vehicle and a bioactive compound. In some embodiments, said lipid vehicle encapsulates said bioactive compound, and wherein said lipid vehicle comprises a cationic lipid as disclosed herein. In some embodiments, said lipid vehicle comprises a co-lipid. In some embodiments, said co-lipid comprises cholesterol or dioleoyl-phosphatidylethanolamine (DOPE). In some embodiments, said lipid vehicle comprises a liposome.

In some embodiments, said liposome comprises a cationic liposome. In some embodiments, the presently disclosed delivery systems further comprise a polycation, wherein said lipid vehicle encapsulates said polycation. In some embodiments, said polycation comprises a polycationic polypeptide. In some embodiments, said polycationic polypeptide comprises protamine.

In some embodiments of the presently disclosed subject matter, said bioactive compound comprises a cytotoxic bioactive compound. In some embodiments of the presently disclosed subject matter, said bioactive compound comprises a polynucleotide. In some embodiments, said polynucleotide comprises a silencing element, wherein expression or introduction of said silencing element into a cell reduces the expression of a target polynucleotide or the polypeptide encoded thereby. In some embodiments, said silencing element comprises an interfering RNA. In some embodiments, said interfering RNA comprises an siRNA. In some embodiments, said target polynucleotide comprises an oncogene. In some embodiments, said oncogene comprises an epidermal growth factor receptor. In some embodiments, said polynucleotide comprises a coding sequence for a polypeptide of interest. In some embodiments, said polypeptide of interest comprises a tumor suppressor.

In some embodiments, the delivery systems of the presently disclosed subject matter further comprise a polyanionic carrier macromolecule, wherein said polyanionic carrier macromolecule is encapsulated by said lipid vehicle. In some embodiments, said polyanionic carrier macromolecule comprises a carrier polynucleotide. In some embodiments, said polyanionic carrier macromolecule comprises a polyanionic carrier polysaccharide, a polyanionic carrier polypeptide, or a combination thereof. In some embodiments, said polyanionic carrier polysaccharide comprises a glycosaminoglycan. In some embodiments, said glycosaminoglycan is selected from the group consisting of heparin sulfate, hyaluronic acid, chondroitin sulfate, dermatin sulfate, keratan sulfate, and dextran sulfate. In some embodiments, said glycosaminoglycan comprises hyaluronic acid. In some embodiments, said polyanionic carrier polypeptide comprises a poly-glutamic acid or a poly-aspartic acid.

In some embodiments of the presently disclosed delivery systems, said lipid vehicle comprises an exterior surface, wherein said exterior surface comprises a polyethylene glycol (PEG) molecule.

In some embodiments of the presently disclosed delivery systems, said lipid vehicle comprises a supported bilayer. In some embodiments, said delivery system comprises a stealth delivery system.

In some embodiments of the presently disclosed delivery systems, said lipid vehicle of said delivery system comprises an exterior surface, wherein said exterior surface comprises a targeting ligand, thereby forming a targeted delivery system, wherein said targeting ligand targets said targeted delivery system to a targeted cell. In some embodiments, said targeting ligand comprises a benzamide derivative. In some embodiments, said benzamide derivative comprises anisamide. In some embodiments, anisamide (AA) is conjugated to 1,2-distearoyl-sn-glycero-S-phosphoethanolamine-N-carboxypolyethylene glycol (DSPE-PEG), thereby producing DSPE-PEG-AA.

In some embodiments of the presently disclosed delivery systems, said targeted cell comprises a cancer cell. In some embodiments, said cancer is selected from the group consisting of a bladder cancer, a brain tumor, a breast cancer, a cervical cancer, a colorectal cancer, an esophageal cancer, an endometrial cancer, a hepatocellular carcinoma, a laryngeal cancer, a lung cancer, an osteosarcoma, an ovarian cancer, a pancreatic cancer, a prostate cancer, a renal cancer, and a thyroid cancer. In some embodiments, said cancer comprises a lung cancer.

The presently disclosed subject matter also provides in some embodiments pharmaceutical compositions comprising presently disclosed delivery systems and a pharmaceutically acceptable carrier.

The presently disclosed subject matter also provides in some embodiments methods for delivering bioactive compounds to cells. In some embodiments, said methods comprise contacting said cells with a delivery system of the presently disclosed subject matter.

The presently disclosed subject matter also provides in some embodiments methods for killing cells. In some embodiments, said methods comprise contacting said cells with a cationic lipid of the presently disclosed subject matter.

The presently disclosed subject matter also provides in some embodiments methods for killing cells comprising contacting said cells with a delivery system of the presently disclosed subject matter, wherein said cationic lipids have cytotoxic activity.

The presently disclosed subject matter also provides methods for selectively killing cells. In some embodiments, said methods comprise contacting said cells with lipid-targeting ligand conjugates, wherein said lipid-targeting ligand conjugates comprise a cationic lipid of the presently disclosed subject matter, and wherein said cationic lipids are physically associated with a targeting ligand.

The presently disclosed subject matter also provides in some embodiments methods for selectively killing cells comprising contacting said cells with a targeted delivery system, wherein said targeted delivery system comprises a lipid vehicle encapsulating said bioactive compound, wherein said lipid vehicle comprises a cationic lipid of the presently disclosed subject matter, wherein said lipid vehicle comprises an exterior surface, and wherein said exterior surface of said lipid vehicle comprises a targeting ligand. In some embodiments, said bioactive compound comprises a cytotoxic bioactive compound. In some embodiments, said targeting ligand comprises a benzamide derivative. In some embodiments, said benzamide derivative comprises anisamide.

The presently disclosed subject matter also provides in some embodiments methods for treating cancers in subjects. In some embodiments, said methods comprise administering to said subjects a pharmaceutical composition of the presently disclosed subject matter.

The presently disclosed subject matter also provides in some embodiments methods for treating disease or unwanted conditions in a subject. In some embodiments, said methods comprise administering to said subject a pharmaceutical composition of the presently disclosed subject matter comprising a bioactive compound that has therapeutic activity against said diseases or unwanted conditions. In some embodiments, said disease comprises a cancer. In some embodiments, said cancer comprises a lung cancer.

The presently disclosed subject matter also provides in some embodiments methods for enhancing the cytotoxic activity of a cytotoxic bioactive compound in a subject. In some embodiments, said method comprises administering to said subject a pharmaceutical composition of the presently disclosed subject matter and a cytotoxic bioactive compound.

The presently disclosed subject matter also provides in some embodiments methods for enhancing the cytotoxic activity of a cytotoxic bioactive compound in a subject comprising administering a pharmaceutical composition of the presently disclosed subject matter to said subject, wherein said cationic lipid and said bioactive compound of said delivery system have cytotoxic activity.

The presently disclosed subject matter also provides in some embodiments methods for making a cytotoxic delivery system comprising a lipid vehicle and a bioactive compound, wherein said lipid vehicle encapsulates said bioactive compound, said method comprising mixing a lipid vehicle comprising a cationic lipid of the presently disclosed subject matter with a bioactive compound, thereby forming said cytotoxic delivery system. In some embodiments, said bioactive compound comprises a cytotoxic bioactive compound.

The presently disclosed subject matter also provides in some embodiments methods for making a cytotoxic polynucleotide delivery system comprising a lipid vehicle encapsulating a polycation and a polynucleotide. In some embodiments, said methods comprise (a) mixing a polynucleotide and a polycation, thereby forming a polynucleotide/polycation solution; and (b) mixing a lipid vehicle comprising a cationic lipid of the presently disclosed subject matter with said polynucleotide/polycation solution, thereby forming said cytotoxic delivery system. In some embodiments, a method for making a cytotoxic polynucleotide delivery system comprising a lipid vehicle encapsulating a polycation and a polynucleotide of the presently disclosed subject matter comprises (a) mixing a lipid vehicle comprising the cationic lipid according to claim 5 and a polycation, thereby forming a lipid vehicle/polycation solution; and (b) mixing said lipid vehicle/polycation solution with a polynucleotide, thereby forming said cytotoxic delivery system. In some embodiments, said polynucleotide comprises a cytotoxic polynucleotide. In some embodiments, step (b) produces a lipid vehicle comprising a core supported bilayer. In some embodiments, said lipid vehicle comprises a liposome. In some embodiments, said liposome comprises a cationic liposome.

In some embodiments, the presently disclosed methods further comprise post-inserting at least one of a lipid-targeting ligand conjugate and a lipid-PEG conjugate into a lipid vehicle of the presently disclosed subject matter, wherein said post-insertion step is performed after forming said delivery system or said polynucleotide delivery system. In some embodiments, said cytotoxic delivery system or said cytotoxic polynucleotide delivery system comprises a stealth cytotoxic delivery system or a stealth cytotoxic polynucleotide delivery system. In some embodiments, said post-insertion step comprises incubating said delivery system or said polynucleotide delivery system with a lipid-PEG conjugate at a concentration of about 5 to about 20 mol %. In some embodiments, said concentration of said lipid-PEG conjugate comprises about 10 mol %. In some embodiments, said lipid-PEG conjugate comprises a PEG molecule having a molecular weight of about 2000 g/mol. In some embodiments, said lipid-PEG conjugate comprises a 1,2-distearoyl-sn-glycero-5-phosphoethanolamine-N-carboxy-polyethylene glycol$_{2000}$ (DSPE-PEG$_{2000}$).

DETAILED DESCRIPTION OF THE INVENTION

Figure 1:
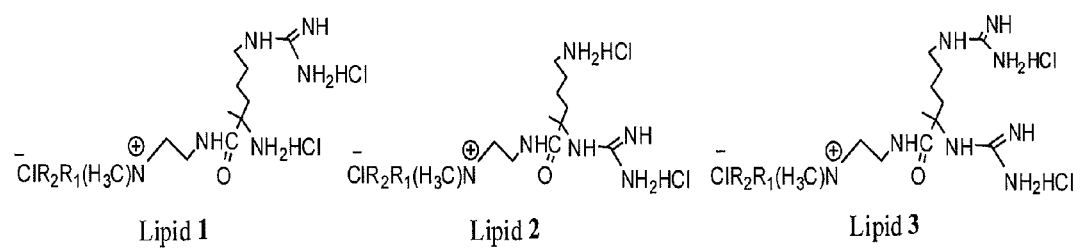
FIG. 1 presents the chemical structures of lipids 1-3.

The present inventions now will be described more fully hereinafter with reference to the accompanying figures, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated figures. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

It is to be noted that the term "a" or "an" entity refers to one or more of that entity; for example, "a cationic lipid" is understood to represent one or more cationic lipids. As such, the terms "a" (or "an"), "one or more," and "at least one" can be used interchangeably herein.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

I. Compositions

Provided herein are novel cationic lipids and pharmaceutical compositions comprising the same. Further provided are delivery systems comprising the cationic lipids of the invention.

A. Cationic Lipids

The invention provides guanidinium-containing cationic, amphiphilic lipids having a single or double guanidinium headgroup. The guanidinium group remains protonated over a much wider range of pH than other basic groups due to its high pKa value (13.5). This characteristic contributes to the cationic nature of the lipids.

The novel cationic lipids are of formula (I):

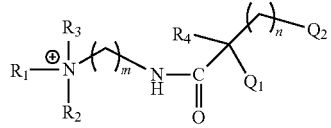

wherein:

m and n are each independently integers from 1 to 8;

$R_1$ and $R_2$ are each independently —$(CH_2)_p$—$CH_3$, wherein p is an integer from 8 to 24;

$R_3$ and $R_4$ are each independently selected from the group consisting of H, alkyl, and substituted alkyl;

$Q_1$ and $Q_2$ are selected from the group consisting of:

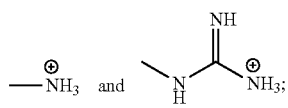

wherein at least one of $Q_1$ or $Q_2$ is:

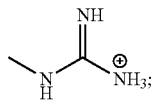

and pharmaceutically acceptable salts thereof.

In some embodiments of the cationic lipid of formula (I), m is 2, n is 4, p is 13, $R_3$ and $R_4$ are each methyl and the cationic lipid can be selected from the group consisting of:

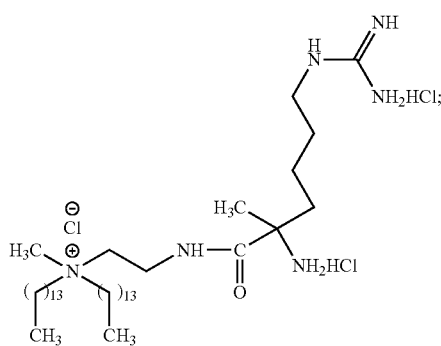

N,N-di-myristoyl-N-methyl-N-2[N'—(N⁶-guanidino-L-lysinyl)]aminoethyl ammonium chloride (DMGLA), hereinafter referred to as lipid 1 (see FIG. 1);

N,N-dimyristoyl-N-methyl-N-2[$N^2$-guanidino-L-lysinyl] aminoethyl ammonium chloride, hereinafter referred to as lipid 2 (see FIG. 1); and

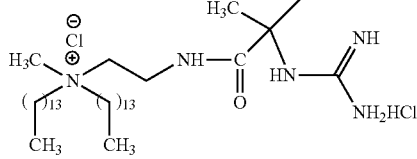

N,N-dimyristoyl-N-methyl-N-2[N'—(N2, N6-di-guanidino-L-lysinyl)]aminoethyl ammonium chloride, hereinafter referred to as lipid 3 (see FIG. 1).

In certain embodiments of the cationic lipid of formula (I), m is 2, n is 3, p is 17, $R_3$ is H, $R_4$ is methyl,

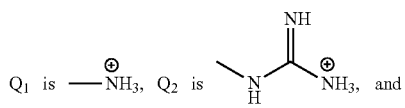

the lipid has the following chemical structure:

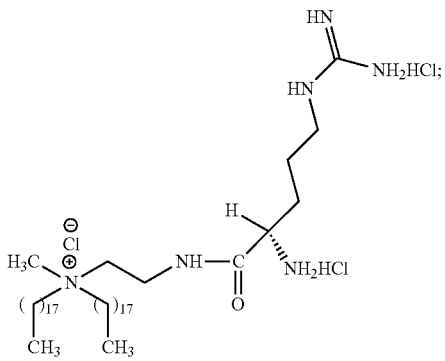

hereinafter referred to as N-methyl-N-(2-(arginoylamino)ethyl)-N,N-Dioctadecyl aminium chloride or distearoyl arginyl ammonium chloride] (DSAA).

In other embodiments of the cationic lipid of formula (I), m is 2, n is 4, p is 17, $R_3$ and $R_4$ are each methyl,

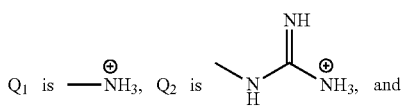

the cationic lipid of formula (I) has the following chemical structure:

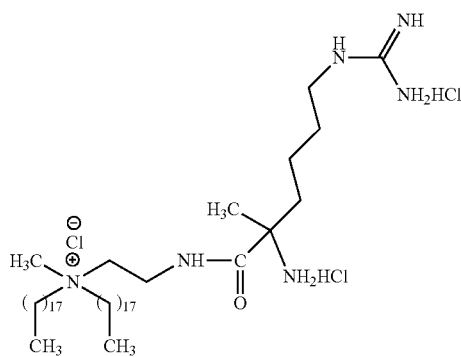

N,N-di-stearoyl-N-methyl-N-2[N'—(N-6-guanidino-L-lysinyl)]aminoethyl ammonium chloride; hereinafter referred to as DSGLA. For the purposes of the present invention, DSAA and DSGLA are referred to as derivatives of lipid 1 (DMGLA).

As used herein, a "derivative" refers to a chemical compound that is derived from or obtained from a parent compound and contains essential elements of the parent compound, but typically has one or more different functional groups. Such functional groups can be added to a parent compound, for example, to improve the molecule's solubility, absorption, biological half life, fluorescent properties, and the like, or to decrease the toxicity of the molecule, eliminate or attenuate any undesirable side effect of the molecule, and the like. It is to be understood that the term "derivative" encompasses a pharmaceutically acceptable salt, as described herein. An "active derivative" is a derivative that retains an activity recited herein (e.g., the ability to deliver a bioactive compound to a cell, cytotoxic activity).

Figure 2:
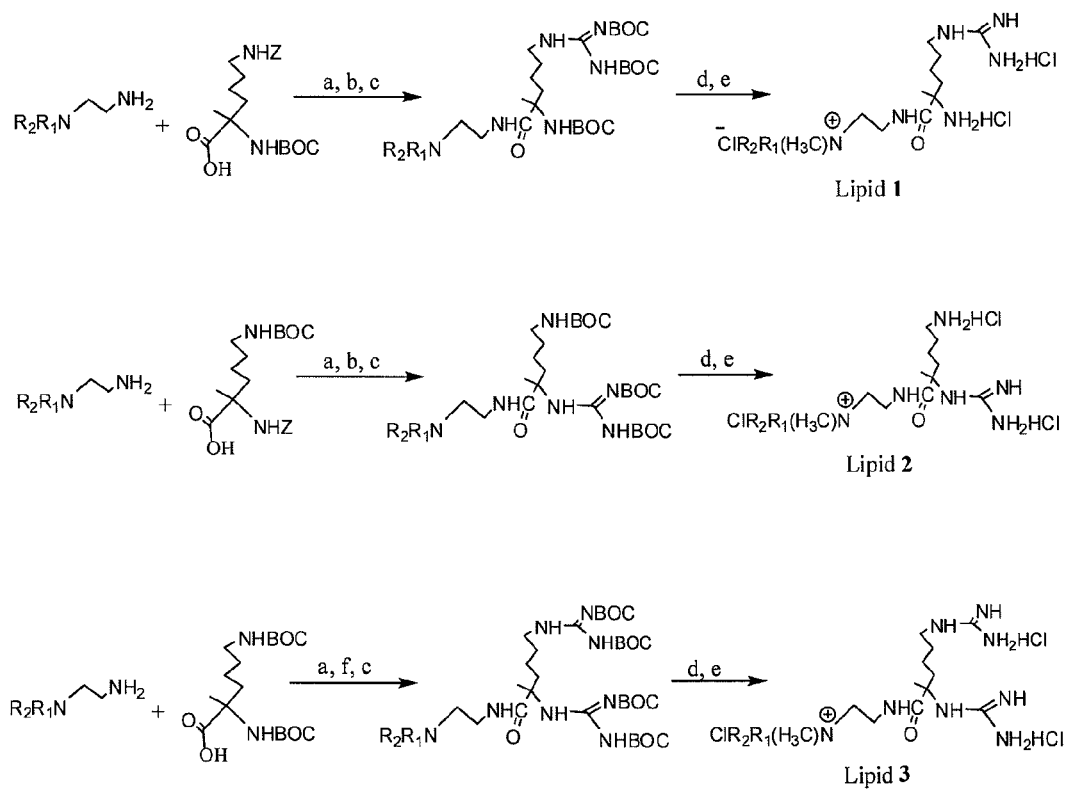
FIG. 2 depicts the scheme used to synthesize lipids 1, 2, and 3.
Figure 3:
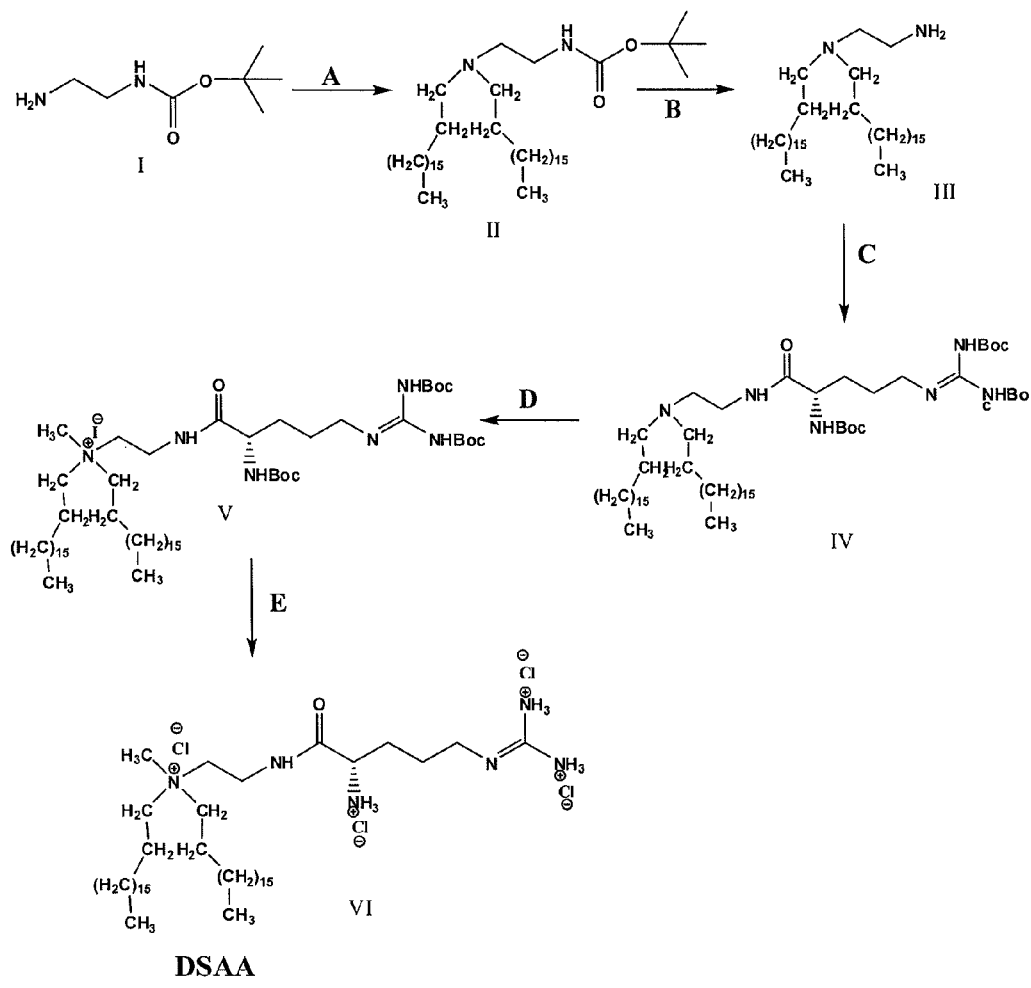
FIG. 3 depicts the scheme used to synthesize the lipid N-methyl-N-(2-(arginoylamino) ethyl)-N,N-Di octadecyl aminium chloride or di stearoyl arginyl ammonium chloride] (DSAA).

One may use any method known to one of skill in the art to prepare the cationic lipids of formula (I), including those described herein. Non-limiting synthetic methods for the synthesis of the cationic lipids are summarized in Examples 1 and 9 and are depicted in FIGS. 2 and 3.

It will be apparent to one of skill in the art that a cationic lipid of formula (I) can be isolated or purified from its constituents using methods well known to the skilled artisan. Thus, the invention embodies isolated cationic lipids of formula (I), wherein the term "isolated" when referring to a lipid species means that the lipid has been separated, fully or partially, from all other substances. Isolated lipids also can refer to lipids dissolved in a solvent.

1. Pharmaceutically Acceptable Salts

The cationic lipids as described herein can be formulated as a pharmaceutically acceptable salt. The phrase "pharmaceutically acceptable salt(s)," as used herein, means those salts of the presently disclosed compounds that are safe and effective for use in a subject and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, borate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, pamoate (i.e., 1,1'-methylene-bis-(2-hydroxy-3-naphthoate)), mesylate salts. Certain of the presently disclosed compounds can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see Berge et al. (1977) *J. Pharm. Sci.* 66:1-19, which is incorporated herein by reference. The salts of the lipids described herein can be prepared, for example, by reacting the appropriate equivalent of the compound with the desired acid or base in solution. After the reaction is complete, the salts are crystallized from solution by the addition of an appropriate amount of solvent in which the salt is insoluble.

2. Cytotoxic Lipids

In some embodiments, the cationic lipids of formula (I) have cytotoxic activity. As used herein, a compound having "cytotoxic activity" comprises a compound (i.e., a cationic lipid or drug) which, upon contacting a cell or entering a cell, results in the prevention or reduction in the rate of reproduction, cell division, or growth of a cell. The cytotoxic molecule can also induce cell death, either by necrosis or apoptosis. Methods for testing a molecule for cytotoxic activity are well known in the art and include, but are not limited to, the following in vitro assays: the MTT assay, a colorimetric assay, which measures the activity of mitochondrial reductase enzymes with the tetrazolium salt 3-(4,5-Dimethylthiazol-2-yl)-2,5-diphenyltetrazolium bromide, and similar assays using other tetrazolium salts and formazan dyes, such as XTT, and the WST assay; the Trypan blue (TB) assay, Sulforhodamine B (SRB) assay, and the clonogenic assay. Further, methods that are known in the art for measuring levels of cellular necrosis and apoptosis can be used to determine if a cationic lipid or drug has cytotoxic activity. Such methods for the detection of apoptosis include, but are not limited to, the TUNEL Assay, measuring caspase activity, DNA fragmentation, poly(ADP-ribose) polymerase (PARP) activation, mitochondrial cytochrome C release, apoptosis-inducing factor (AIF) translocation, and Annexin-V staining. In some embodiments, the percentage of cells that are killed or exhibit a reduced rate of reproduction, cell division, or cellular growth upon contacting the cytotoxic molecule are in the range of about 1% to about 100%, including, for example, 1%, 5%, 10%, 20%, 30%, 40%, 50%, 60%, 70%, 80%, 90%, 100%, and any other such value between about 1% and about 100%.

While not being bound by any theory or mechanism of action, it is believed that the guanidinium group of the cationic lipids of formula (I), which easily donates an electron, can generate a superoxide, forming a hydroxyl radical, which might contribute to the cytotoxicity of the compounds (Hiramatsu (2003) *Mol. Cell. Biochem.* 244:57-62). In addition, DSGLA, a derivative of lipid 1, can induce reactive oxygen species (ROS) (data not shown). While not being bound by any theory or mechanism of action, DSGLA-induced ROS may cause membrane and DNA damage, enhancing poly (ADP-ribose) polymerase-1 (PARP-1) activation and triggering AIF translocation from the mitochondria to the nucleus, key events in the induction of apoptosis (Fleury, Mignotte, and Vayssiere (2002) *Biochimie* 84:131-141; Zorov, Juhaszova, and Sollott (2006) *Biochim. Biophys. Acta* 1757:509-517). DSGLA also inhibits the activation of ERK (FIG. 5C and Experimental Example 4), which might also trigger apoptosis (Liu et al. (2006) *Oncogene* 25:5640-5647).

3. Targeting Ligands

Further provided are compositions comprising a cationic lipid of formula (I) and a targeting ligand that is physically associated with the cationic lipid. In some embodiments, the cationic lipid of formula (I) that is physically associated with a targeting ligand has cytotoxic activity.

By "targeting ligand" is intended a molecule that targets the cationic lipid or a physically associated molecule to a targeted cell or tissue. Targeting ligands can include, but are not limited to, small molecules, peptides, lipids, sugars, oligonucleotides, hormones, vitamins, antigens, antibodies or fragments thereof, specific membrane-receptor ligands, ligands capable of reacting with an anti-ligand, fusogenic peptides, nuclear localization peptides, or a combination of such compounds. Non-limiting examples of targeting ligands include asialoglycoprotein, insulin, low density lipoprotein (LDL), folate, benzamide derivatives, and monoclonal and polyclonal antibodies directed against cell surface molecules. In some embodiments, the small molecule comprises a benzamide derivative. In some of these embodiments, the benzamide derivative comprises anisamide.

By "targeted cell" is intended the cell to which a targeting ligand recruits a physically associated molecule. The targeting ligand can interact with one or more constituents of a target cell. The targeted cell can be any cell type or at any developmental stage, exhibiting various phenotypes, and can be in various pathological states (i.e., abnormal and normal states). For example, the targeting ligand can associate with normal, abnormal, and/or unique constituents on a microbe (i.e., a prokaryotic cell (bacteria), viruses, fungi, protozoa or parasites) or on a eukaryotic cell (e.g., epithelial cells, muscle cells, nerve cells, sensory cells, cancerous cells, secretory cells, malignant cells, erythroid and lymphoid cells, stem cells). Thus, the targeting ligand can associate with a constituent on a target cell which is a disease-associated antigen including, for example, tumor-associated antigens and autoimmune disease-associated antigens. Such disease-associated antigens include, for example, growth factor receptors, cell cycle regulators, angiogenic factors, and signaling factors.

In some embodiments, the targeting ligand interacts with a cell surface protein on the targeted cell. In some of these embodiments, the expression level of the cell surface protein that is capable of binding to the targeting ligand is higher in the targeted cell relative to other cells. For example, cancer cells overexpress certain cell surface molecules, such as the HER2 receptor (breast cancer) or the sigma receptor. In certain embodiments wherein the targeting ligand comprises a benzamide derivative, such as anisamide, the targeting ligand targets the associated molecule to sigma-receptor overexpressing cells, which can include, but is not limited to, cancer cells such as small- and non-small-cell lung carcinoma, renal carcinoma, colon carcinoma, sarcoma, breast cancer, melanoma, glioblastoma, neuroblastoma, and prostate cancer (Aydar, Palmer, and Djamgoz (2004) *Cancer Res.* 64:5029-5035).

Thus, in some embodiments, the targeted cell comprises a cancer cell. The terms "cancer" or "cancerous" refer to or describe the physiological condition in mammals that is typically characterized by unregulated cell growth. As used herein, "cancer cells" or "tumor cells" refer to the cells that are characterized by this unregulated cell growth. The term "cancer" encompasses all types of cancers, including, but not limited to, all forms of carcinomas, melanomas, sarcomas, lymphomas and leukemias, including without limitation, bladder carcinoma, brain tumors, breast cancer, cervical cancer, colorectal cancer, esophageal cancer, endometrial cancer, hepatocellular carcinoma, laryngeal cancer, lung cancer, osteosarcoma, ovarian cancer, pancreatic cancer, prostate cancer, renal carcinoma and thyroid cancer. In some embodiments, the targeted cancer cell comprises a lung cancer cell. The term "lung cancer" refers to all types of lung cancers, including but not limited to, small cell lung cancer (SCLC), non-small-cell lung cancer (NSCLC, which includes large-cell lung cancer, squamous cell lung cancer, and adenocarcinoma of the lung), and mixed small-cell/large-cell lung cancer.

The targeting ligand can be physically associated with a cationic lipid of formula (I). As used herein, the term "physically associated" refers to either a covalent or non-covalent interaction between two molecules. As used herein, the term "covalent bond" or "covalent interaction" refers to a chemical bond, wherein a pair of electrons is shared between two atoms. Two molecules are said to be chemically bound to one another when the molecules have at least one chemical bond between atoms that make up the molecules. One chemical bond between two molecules is therefore comprised of the sharing of one pair of electrons between an atom in one molecule with an atom in another molecule. For example, a targeting ligand can be covalently bound to a lipid of the invention through one of the nitrogen atoms or one of the R groups of the cationic lipids. A "conjugate" refers to the complex of molecules that are covalently bound to one another. For example, the complex of a lipid covalently bound to a targeting ligand can be referred to as a lipid-targeting ligand conjugate.

Alternatively, the targeting ligand can be non-covalently bound to the lipids of formula (I) or active derivatives thereof. "Non-covalent bonds" or "non-covalent interactions" do not involve the sharing of pairs of electrons, but rather involve more dispersed variations of electromagnetic interactions, and can include hydrogen bonding, ionic interactions, Van der Waals interactions, and hydrophobic bonds. Such lipid-targeting ligand conjugates can be readily obtained according to techniques widely described in the literature.

B. Delivery Systems

The invention further provides delivery systems. As used herein, a "delivery system" or "delivery system complex" comprises a lipid vehicle and a bioactive compound, wherein the lipid vehicle encapsulates the bioactive compound. As used herein, "lipid vehicle" refers to a lipid composition that is capable of delivering a bioactive compound to a physiological site or cell. Lipid vehicles can include, but are not limited to, micelles, microemulsions, macroemulsions, and liposomes. The lipid vehicles are comprised of a cationic lipid of formula (I). The lipid vehicles can further comprise at least one additional type of lipid, including, but not limited to, another cationic lipid and a co-lipid, as described herein.

As used herein, the term "lipid" refers to a group of organic compounds that has lipophilic or amphiphilic properties, including, but not limited to, fats, fatty oils, essential oils, waxes, steroids, sterols, phospholipids, glycolipids, sulpholipids, aminolipids, chromolipids (lipochromes), and fatty acids. The term "lipid" encompasses both naturally occurring and synthetically produced lipids. "Lipophilic" refers to those organic compounds that dissolve in fats, oils, lipids, and non-polar solvents, such as organic solvents. Lipophilic compounds are sparingly soluble or insoluble in water. Thus, lipophilic compounds are hydrophobic. Amphipathic lipids, also referred to herein as "amphiphilic lipids" refer to a lipid molecule having both hydrophilic and hydrophobic characteristics. The hydrophobic group of an amphipathic lipid, as described in more detail immediately herein below, can be a long chain hydrocarbon group. The hydrophilic group of an amphipathic lipid can include a charged group, e.g., an anionic or a cationic group, or a polar, uncharged group. Amphipathic lipids can have multiple hydrophobic groups, multiple hydrophilic groups, and combinations thereof. Because of the presence of both a hydrophobic group and a hydrophilic group, amphipathic lipids can be soluble in water, and to some extent, in nonpolar organic solvents.

As used herein, "hydrophilic" is a physical property of a molecule that is capable of hydrogen bonding with a water ($H_2O$) molecule and is soluble in water and other polar solvents. The terms "hydrophilic" and "polar" can be used interchangeably. Hydrophilic characteristics derive from the presence of polar or charged groups, such as carbohydrates, phosphate, carboxylic, sulfato, amino, sulfhydryl, nitro, hydroxy and other like groups.

Conversely, the term "hydrophobic" is a physical property of a molecule that is repelled from a mass of water and can be referred to as "nonpolar," or "apolar," all of which are terms that can be used interchangeably with "hydrophobic." Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s).

The lipid vehicles comprise amphipathic lipids including, but not limited to, phospholipids, aminolipids and sphingolipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine and dilinoleoylphosphatidylcholine. Other compounds lacking in phosphorus, such as sphingolipid, glycosphingolipid families, diacylglycerols and β-acyloxyacids, also are within the group designated as amphipathic lipids. Amphipathic lipids include cationic, anionic, zwitterionic, or neutral amphipathic lipids.

The lipid vehicles of the delivery systems comprise a cationic lipid of formula (I) and may comprise other cationic lipids. As used herein, "cationic lipid" encompasses any of a number of lipid species that carry a net positive charge at physiological pH, which can be determined using any method known to one of skill in the art. Such lipids include, but are not limited to, the lipids of the invention as described herein, and other previously described cationic lipids, such as N,N-dioleyl-N,N-dimethylammonium chloride ("DODAC"); N-(2,3-dioleoyloxy) propyl)-N,N,N-trimethylammonium chloride ("DOTAP"); N-(2,3-dioleyloxy) propyl)-N,N,N-trimethylammonium chloride ("DOTMA") or other N—(N,N-1-dialkoxy)-alkyl-N,N,N-trisubstituted ammonium surfactants; N,N-distearyl-N,N-dimethylammonium bromide ("DDAB"); 3-(N—(N',N'-dimethylaminoethane)-carbamoyl)cholesterol ("DC-Chol") and N-(1,2-dimyristyloxyprop-3-yl)-N,N-dimethyl-N-hydroxyethyl ammonium bromide ("DMRIE"); 1,3-dioleoyl-3-trimethylammonium-propane, N-(1-(2,3-dioleyloxy)propyl)-N-(2-(sperminecarboxamido) ethyl)-N,N-dimethyl-1 ammonium trifluoro-acetate (DOSPA); GAP-DLRIE; DMDHP; 3-β[$^4$N—($^1$N,$^8$N-diguanidino spermidine)-carbamoyl]cholesterol (BGSC); 3-β[N,N-diguanidinoethyl-aminoethane)-carbamoyl]cholesterol (BGTC); N,N$^1$,N$^2$,N$^3$ Tetra-methyltetrapalmityl-spermine (cellfectin); N-t-butyl-N'-tetradecyl-3-tetradecyl-aminopropion-amidine (CLONfectin); dimethyldioctadecyl ammonium bromide (DDAB); 1,3-dioleoyloxy-2-(6-carboxyspermyl)-propyl amide (DOSPER); 4-(2,3-bis-palmitoyloxy-propyl)-1-methyl-1H-imidazole (DPIM) N,N,N',N'-tetramethyl-N,N'-bis(2-hydroxyethyl)-2,3 dioleoyloxy-1,4-butanediammonium iodide) (Tfx-50); 1,2 dioleoyl-3-(4'-trimethylammonio) butanol-sn-glycerol (DOBT) or cholesteryl (4' trimethylammonia) butanoate (ChOTB) where the trimethylammonium group is connected via a butanol spacer arm to either the double chain (for DOTB) or cholesteryl group (for ChOTB); DORI (DL-1,2-dioleoyl-3-dimethylaminopropyl-β-hydroxyethylammonium) or DORIE (DL-1,2-O-dioleoyl-3-dimethylaminopropyl-β-hydroxyethylammonium) (DORIE) or analogs thereof as disclosed in WO 93/03709; 1,2-dioleoyl-3-succinyl-sn-glycerol choline ester (DOSC); cholesteryl hemisuccinate ester (ChOSC); lipopolyamines such as dioctadecylamidoglycylspermine (DOGS) and dipalmitoyl phosphatidylethanolamylspermine (DPPES) or the cationic lipids disclosed in U.S. Pat. No. 5,283,185; cholesteryl-3,3-carboxyl-amido-ethylenetrimethylammonium iodide; 1-dimethylamino-3-trimethylammonio-DL-2-propyl-cholesteryl carboxylate iodide; cholesteryl-3-β-carboxyamidoethyleneamine; cholesteryl-3-β-oxysuccinamido-ethylenetrimethylammonium iodide; 1-dimethylamino-3-trimethylammonio-DL-2-propyl-cholesteryl-3-β-oxysuccinate iodide; 2-(2-trimethylammonio)-ethylmethylamino ethyl-cholesteryl-3-β-oxysuccinate iodide; and 3-β-N-(polyethyleneimine)-carbamoylcholesterol.

In some embodiments, in addition to cationic lipids, the lipid vehicles used for delivery systems comprise a co-lipid. As used herein, a "co-lipid" refers to a non-cationic lipid, which includes neutral (uncharged), zwitterionic, or anionic lipids. The term "neutral lipid" refers to any of a number of lipid species that exist either in an uncharged or neutral zwitterionic form at physiological pH. The term "anionic lipid" encompasses any of a number of lipid species that carry a net negative charge at physiological pH. Co-lipids can include, but are not limited to, diacylphosphatidylcholine, diacylphosphatidylethanolamine, ceramide, sphingomyelin, cephalin, cholesterol, cerebrosides and diacylglycerols, phospholipid-related materials, such as lecithin, phosphatidylethanolamine, lysolecithin, lysophosphatidylethanolamine, phosphatidylserine, phosphatidylinositol, cardiolipin, phosphatidic acid, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), palmitoyloleyolphosphatidylglycerol (POPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-car-boxylate (DOPE-mal), stearylamine, dodecylamine, hexadecylamine; acetyl palmitate, glycerolricinoleate, hexadecyl stereate, isopropyl myristate, amphoteric acrylic polymers, triethanolamine-lauryl sulfate, alkylaryl sulfate polyethyloxylated fatty acid amides, lysophosphatidylcholine, and dioctadecyldimethyl ammonium bromide and the like.

Co-lipids also include polyethylene glycol-based polymers such as PEG 2000, PEG 5000 and polyethylene glycol conjugated to phospholipids or to ceramides, as described in U.S. Pat. No. 5,820,873, incorporated herein by reference.

The lipid vehicles of the delivery systems comprising a cationic lipid of formula (I) can include, but are not limited to, micelles, microemulsions, macroemulsions, and liposomes.

The term "micelles" refers to colloidal aggregates of amphipathic molecules, such as the novel cationic lipids of formula (I), that are formed at a well-defined concentration known as the critical micelle concentration. Micelles are oriented with the nonpolar portions of the lipid molecules at the interior of the micelle and the polar portions at the exterior surface, exposed to water. The typical number of aggregated molecules in a micelle (aggregation number) has a range from about 50 to about 100.

The term "micelles" also refers to inverse or reverse micelles, which are formed in a nonpolar solvent, wherein the nonpolar portions are at the exterior surface, exposed to the nonpolar solvent and the polar portion is oriented towards the interior of the micelle.

As described herein, microemulsions are essentially swollen micelles, although not all micellar solutions can be swollen to form a microemulsion. Microemulsions are thermodynamically stable, are formed spontaneously, and contain particles that are extremely small. Droplet diameters in microemulsions typically range from about 10 to about 100 nm. In contrast, the term macroemulsions refers to droplets having diameters greater than about 100 nm.

Liposomes are self-assembling, substantially spherical vesicles comprising a lipid bilayer that encircles an aqueous interior or core, wherein the lipid bilayer comprises amphipathic lipids having hydrophilic headgroups and hydrophobic tails, in which the hydrophilic headgroups of the amphipathic lipid molecules are oriented toward the aqueous solution, while the hydrophobic tails orient toward the interior of the bilayer. The lipid bilayer structure thereby comprises two opposing monolayers that are referred to as the "inner leaflet" and the "outer leaflet," wherein the hydrophobic tails are shielded from contact with the surrounding medium. The "inner leaflet" is the monolayer wherein the hydrophilic head groups are oriented toward the aqueous core of the liposome. The "outer leaflet" is the monolayer comprising amphipathic lipids, wherein the hydrophilic head groups are oriented towards the exterior surface of the liposome. Liposomes typically have a diameter ranging from about 25 nm to about 1 (see, e.g., Shah (ed.) (1998) *Micelles, Microemulsions, and Monolayers: Science and Technology*, Marcel Dekker; Janoff (ed.) (1998) *Liposomes: Rational Design*, Marcel Dekker). The term "liposome" encompasses both multilamellar liposomes comprised of anywhere from two to hundreds of concentric lipid bilayers alternating with layers of an aqueous phase and unilamellar vesicles that are comprised of a single lipid bilayer. Methods for making liposomes are well known in the art and are described elsewhere herein. Liposomes that comprise the cationic lipids of Formula (I) have the cationic lipids incorporated into the lipid bilayer of the liposome.

As used herein, the term "exterior surface" has the ordinary meaning of the term and refers to the outside surface of the lipid vehicle, as opposed to the inner core of the vehicle.

The lipid vehicles of the delivery systems encapsulate a bioactive compound. The terms "encapsulate" and "entrap" are used herein interchangeably and refer to the incorporation or association of a substance or molecule (e.g., a bioactive compound) in or with a lipid vehicle. For example, in those embodiments in which the lipid vehicle is a liposome, the substance or molecule can be associated with the lipid bilayer (for example, if the substance or molecule is hydrophobic) or be present in the aqueous interior of the liposome (for example, if the substance or molecule is hydrophilic), or both. Hydrophobic drugs also can be encapsulated within micelles, a microemulsion, or a macroemulsion.

1. Cationic Liposomes

In accordance with the invention, the lipid vehicle of the delivery system can be a cationic liposome. The term "cationic liposome" as used herein is intended to encompass any liposome as defined above which has a net positive charge or has a zeta potential of greater than 0 mV at physiological pH. The zeta potential or charge of the liposome can be measured using any method known to one of skill in the art. It should be noted that the liposome itself is the entity that is being determined as cationic, meaning that the liposome that has a measurable positive charge at physiological pH can, within an in vivo environment, become attached to other substances. These other substances can be negatively charged and thereby result in the formation of a structure that does not have a positive charge. After a delivery system comprising a cationic liposome is produced, molecules such as lipid-PEG conjugates can be post-inserted into the bilayer of the liposome as described elsewhere herein, thus shielding the surface charge and reducing the zeta potential of the delivery system.

In those embodiments in which the lipid vehicle of the delivery system is a cationic liposome, the cationic liposome comprises a cationic lipid of formula (I) and optionally comprises additional cationic lipids, including, but not limited to those described elsewhere herein. The cationic liposome need not be comprised completely of cationic lipids, however, but must be comprised of a sufficient amount of cationic lipid such that the liposome has a positive charge at physiological pH. The cationic liposomes also can contain co-lipids that are negatively charged or neutral, so long as the net charge of the liposome is positive and/or the surface of the liposome is positively charged at physiological pH.

In these embodiments, the ratio of cationic lipids to co-lipids is such that the overall charge of the resulting liposome is positive at physiological pH. For example, the cationic lipid is present in the liposome at from about 10 mole % to about 100 mole % of total liposomal lipid, in some embodiments, from about 20 mole % to about 80 mole % and, in other embodiments, from about 20 mole % to about 60 mole %. The neutral lipid, when included in the liposome, can be present at a concentration of from about 0 mole % to about 90 mole % of the total liposomal lipid, in some embodiments from about 20 mole % to about 80 mole %, and in other embodiments, from about 40 mole % to about 80 mole %. The negatively charged lipid, when included in the liposome, can be present at a concentration ranging from about 0 mole % to about 49 mole % of the total liposomal lipid, and in certain embodiments, from about 0 mole % to about 40 mole %.

In some embodiments, the cationic liposomes of the delivery systems comprise a cationic lipid of formula (I) and the neutral co-lipid cholesterol at a 1:1 molar ratio.

In some embodiments in which the lipid vehicle of the delivery system is a cationic liposome, the cationic liposome encapsulates an anionic bioactive compound (i.e., a bioactive compound that is negatively charged at physiological pH). In these embodiments, the positively charged cationic lipids comprising the cationic liposomes are physically associated with the negatively charged anionic bioactive compound by attraction between opposite molecular charges.

In some embodiments in which the lipid vehicle is a cationic liposome and the bioactive compound is anionic, the delivery system has a net positive charge, as described in U.S. Pat. No. 6,008,202, which is herein incorporated by reference in its entirety. By "net positive charge" is meant that the positive charges of the cationic lipid (and optionally, polycation, as described elsewhere herein) exceed the negative charge of the anionic bioactive compound. It is to be understood, however, that the present invention also encompasses delivery systems comprising a lipid vehicle having a positively charged surface irrespective of whether the net charge of the complex is positive, neutral or even negative. The charge of the surface of a cationic liposome of a delivery system can be measured by the migration of the complex in an electric field by methods known to those in the art, such as by measuring zeta potential (Martin, Swarick, and Cammarata (1983) Physical Pharmacy & Physical Chemical Principles in the Pharmaceutical Sciences, 3rd ed. Lea and Febiger) or by the binding affinity of the delivery system complex to cell surfaces. Complexes exhibiting a positively charged surface have a greater binding affinity to cell surfaces than complexes having a neutral or negatively charged surface. Further, it is to be understood that the positively charged surface can be sterically shielded by the addition of non-ionic polar compounds, for example, polyethylene glycol, as described elsewhere herein.

2. Bioactive Compounds

By "bioactive compound" is intended any agent that has an effect on a living cell, tissue, or organism, or an agent that can interact with a component (e.g., enzyme) of a living cell, tissue, or organism, including, but not limited to, polynucleotides, polypeptides, polysaccharides, organic and inorganic small molecules. The term "bioactive compound" encompasses both naturally occurring and synthetic bioactive compounds. The term "bioactive compound" can also refer to a detection or diagnostic agent that interacts with a biological molecule to provide a detectable readout that reflects a particular physiological or pathological event.

The bioactive compound of the delivery system can be a drug, including, but not limited to, antimicrobials, antibiotics, antimycobacterial, antifungals, antivirals, neoplastic agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholinergics, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, antioxidants, vaso-active agents, bone-active agents, antiarthritics, and diagnostic agents.

In certain embodiments, the bioactive compound can be a cytotoxic bioactive compound, such as a chemotherapeutic agent, including those frequently used to treat cancers. As used herein, a "cytotoxic bioactive compound" is one that has cytotoxic activity as described elsewhere herein. Chemotherapeutic agents are well known in the art (see e.g., Gilman A. G., et al., The Pharmacological Basis of Therapeutics, 8th Ed., Sec 12:1202-1263 (1990)) and include, but are not limited to, alkylating agents, antimetabolites, natural products and their derivatives, hormones and steroids (including synthetic analogs), toxins, and synthetics. Examples of alkylating agents (e.g., nitrogen mustards, ethylenimine derivatives, alkyl sulfonates, nitrosoureas and triazenes) include uracil mustard, chlormethine, cyclophosphamide (Cytoxan®), ifosfamide, melphalan, chlorambucil, pipobroman, triethylenemelamine, triethylenethiophosphoramine, busulfan, carmustine, lomustine, streptozocin, dacarbazine, and temozolomide. Antimetabolites (including folic acid antagonists, pyrimidine analogs, purine analogs and adenosine deaminase inhibitors) can include, for example, methotrexate, 5-fluorouracil, floxuridine, cytarabine, 6-mercaptopurine, 6-thioguanine, fludarabine phosphate, pentostatine, and gemcitabine. Natural products and their derivatives (including vinca alkaloids, antitumor antibiotics, enzymes, lymphokines and epipodophyllotoxins) also can be used and include, for example, vinblastine, vincristine, vindesine, bleomycin, dactinomycin, daunorubicin, doxorubicin, epirubicin, idarubicin, paclitaxel (paclitaxel is commercially available as taxol, mithramycin, deoxyco-formycin, mitomycin-C, L-asparaginase, interferons (especially IFN-alpha), etoposide, and teniposide. Hormones and steroids (including synthetic analogs) include, for example, 17-alpha-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, or zoladex. Non-limiting examples of toxins include ricin A and diphtheria toxin. Exemplary synthetics (including inorganic complexes such as platinum coordination complexes) include cisplatin, carboplatin, hydroxyurea, amsacrine, procarbazine, mitotane, mitoxantrone, levamisole, and hexamethylmelamine.

As used herein, the term "deliver" refers to the transfer of a substance or molecule (e.g., a bioactive compound) to a physiological site, tissue, or cell. This encompasses delivery to the intracellular portion of a cell or to the extracellular space.

As used herein, the term "intracellular" or "intracellularly" has its ordinary meaning as understood in the art. In general, the space inside of a cell, which is encircled by a membrane, is defined as "intracellular" space. Similarly, as used herein, the term "extracellular" or "extracellulary" has its ordinary meaning as understood in the art. In general, the space outside of the cell membrane is defined as "extracellular" space.

In certain embodiments, the delivery system comprises a cytotoxic delivery system. As used herein, a "cytotoxic delivery system" is one that has cytotoxic activity, as described elsewhere herein. The lipid vehicle of the cytotoxic delivery systems comprises a cationic lipid of formula (I). The cytotoxic activity of the cytotoxic delivery system can be imparted from a cytotoxic cationic lipid of formula (I), a cytotoxic bioactive compound, or both. Thus, in some embodiments, the cytotoxic delivery system comprises a lipid vehicle encapsulating a cytotoxic bioactive compound, wherein the lipid vehicle comprises a cytotoxic cationic lipid of formula (I).

a. Polynucleotide of Interest

In some embodiments, the bioactive compound of the delivery system comprising a cationic lipid of formula (I) comprises a polynucleotide. While not being bound by any theory or mechanism of action, it is believed that the guanidinium headgroup within the cationic lipids of formula (I) functionally mimics the arginyl residues in DNA binding proteins, such as histones and protamine, and aids in the condensation of polynucleotides. The guandinium headgroup also forms characteristic parallel zwitterionic hydrogen bonds with phosphate ions, such as those found in nucleic acid backbones, and can form hydrogen bonds with nucleic acid bases, contributing to the stability of polynucleotide delivery systems (Vigneron et al. (1996) Proc. Natl. Acad. Sci. USA 93:9682-9686).

The term "polynucleotide" is intended to encompass a singular nucleic acid, as well as plural nucleic acids, and refers to a nucleic acid molecule or construct, e.g., messenger RNA (mRNA), plasmid DNA (pDNA), or short interfering RNA (siRNA). A polynucleotide can be single-stranded or double-stranded, linear or circular. A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. The term "polynucleotide" can refer to an isolated nucleic acid or polynucleotide, wherein by "isolated" nucleic acid or polynucleotide is intended a nucleic acid molecule, DNA or RNA, that has been removed from its native environment. Examples of an isolated polynucleotide include recombinant polynucleotides maintained in heterologous host cells or purified (partially or substantially) polynucleotides in solution. Isolated polynucleotides or nucleic acids according to the present invention further include such molecules produced synthetically. Isolated polynucleotides also can include isolated expression vectors, expression constructs, or populations thereof. "Polynucleotide" also can refer to amplified products of itself, as in a polymerase chain reaction. The "polynucleotide" can contain modified nucleic acids, such as phosphorothioate, phosphate, ring atom modified derivatives, and the like. The "polynucleotide" can be a naturally occurring polynucleotide (i.e., one existing in nature without human intervention), or a recombinant polynucleotide (i.e., one existing only with human intervention). While the terms "polynucleotide" and "oligonucleotide" both refer to a polymer of nucleotides, as used herein, an oligonucleotide is typically less than 100 nucleotides in length.

As used herein, the term "polynucleotide of interest" refers to a polynucleotide that is to be delivered to a cell to elicit a desired effect in the cell (e.g., a therapeutic effect, a change in gene expression). A polynucleotide of interest can be of any length and can include, but is not limited to a polynucleotide comprising a coding sequence for a polypeptide of interest or a polynucleotide comprising a silencing element. In certain embodiments, when the polynucleotide is expressed or introduced into a cell, the polynucleotide of interest or polypeptide encoded thereby has therapeutic activity.

The term "polynucleotide delivery system" refers to a delivery system wherein the bioactive compound comprises a polynucleotide. Polynucleotide delivery systems of the present invention comprise the novel cationic lipids of formula (I) as described elsewhere herein. Typically, the lipid vehicle of the polynucleotide delivery system is a cationic liposome. In these embodiments, the cationic liposome is physically associated with the negatively-charged polynucleotide by attraction between opposite molecular charges.

In particular non-limiting embodiments wherein the lipid vehicle comprises a cationic liposome, the polynucleotide delivery system has a +:− charge ratio of between 0.5:1 and 100:1, including but not limited to about 0.5:1, about 1:1, about 2:1, about 3:1, about 4:1, about 5:1, about 6:1, about 7:1, about 8:1, about 9:1, about 10:1, about 15:1, about 20:1, about 40:1, or about 100:1. In some embodiments, the charge ratio is between about 0.5:1 and about 40:1, between about 0.5:1 and about 20:1, between about 0.5:1 and about 10:1, between about 2:1 and about 40:1, between about 2:1 and about 20:1, between about 2:1 and about 15:1, or between about 3:1 and about 9:1. In a specific non-limiting embodiment, the +:− charge ratio is about 5:1. The positive charge is imparted from the cationic liposome and in some embodiments, from the polycation as well. The negative charge is imparted by the polynucleotide and in some embodiments, by a polyanionic carrier macromolecule as well. Thus, in some embodiments, the liposome (+): polycation (+): polynucleotide/polyanionic carrier macromolecule (−) charge ratio is about 4:1:1.

Methods for generating polynucleotide delivery systems comprising liposomes as the lipid vehicle are known in the art and are reviewed in Li and Szoka (2007) *Pharm. Res.* 24:438-449.

i. Polynucleotides Encoding Polypeptides

In some embodiments, the polynucleotide delivery systems comprise a polynucleotide comprising a coding sequence for a polypeptide of interest.

For the purposes of the present invention, a "coding sequence for a polypeptide of interest" or "coding region for a polypeptide of interest" refers to the polynucleotide sequence that encodes that polypeptide. As used herein, the terms "encoding" or "encoded" when used in the context of a specified nucleic acid mean that the nucleic acid comprises the requisite information to direct translation of the nucleotide sequence into a specified polypeptide. The information by which a polypeptide is encoded is specified by the use of codons. The "coding region" or "coding sequence" is the portion of the nucleic acid that consists of codons that can be translated into amino acids. Although a "stop codon" or "translational termination codon" (TAG, TGA, or TAA) is not translated into an amino acid, it can be considered to be part of a coding region. Likewise, a transcription initiation codon (ATG) may or may not be considered to be part of a coding region. Any sequences flanking the coding region, however, for example, promoters, ribosome binding sites, transcriptional terminators, introns, and the like, are not considered to be part of the coding region. In some embodiments, however, while not considered part of the coding region per se, these regulatory sequences and any other regulatory sequence, particularly signal sequences or sequences encoding a peptide tag, may be part of the polynucleotide sequence encoding the polypeptide of interest. Thus, a polynucleotide sequence encoding a polypeptide of interest comprises the coding sequence and optionally any sequences flanking the coding region that contribute to expression, secretion, and/or isolation of the polypeptide of interest.

The term "expression" has its meaning as understood in the art and refers to the process of converting genetic information encoded in a gene or a coding sequence into RNA (e.g., mRNA, rRNA, tRNA, or snRNA) through "transcription" of a polynucleotide (e.g., via the enzymatic action of an RNA polymerase), and for polypeptide-encoding polynucleotides, into a polypeptide through "translation" of mRNA. Thus, an "expression product" is, in general, an RNA transcribed from the gene (e.g., either pre- or post-processing) or polynucleotide or a polypeptide encoded by an RNA transcribed from the gene (e.g., either pre- or post-modification).

As used herein, the term "polypeptide" or "protein" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

The term "polypeptide of interest" refers to a polypeptide that is to be delivered to a cell or is encoded by a polynucleotide that is to be delivered to a cell to elicit a desired effect in the cell (e.g., a therapeutic effect). The polypeptide of interest can be of any species and of any size. In certain embodiments, however, the protein or polypeptide of interest is a therapeutically useful protein or polypeptide. In some embodiments, the protein can be a mammalian protein, for example a human protein. In certain embodiments, the polynucleotide comprises a coding sequence for a tumor suppressor or a cytotoxin (e.g., diphtheria toxin (DT), Pseudomonas exotoxin A (PE), pertussis toxin (PT), and the pertussis adenylate cyclase (CYA)).

The term "tumor suppressor" refers to a polypeptide or a gene encoding a polypeptide that is capable of inhibiting the development, growth, or progression of cancer. Tumor suppressor polypeptides include those proteins that regulate cellular proliferation or responses to cellular and genomic damage, or induce apoptosis. Non-limiting examples of tumor suppressor genes include p53, p110Rb, and p72. Thus, in some embodiments, the lipid/polynucleotide delivery systems of the present invention comprise a polynucleotide comprising a coding sequence for a tumor suppressor.

Extensive sequence information required for molecular genetics and genetic engineering techniques is widely publicly available. Access to complete nucleotide sequences of mammalian, as well as human, genes, cDNA sequences, amino acid sequences and genomes can be obtained from GenBank at the website www.ncbi.nlm.nih.gov/Entrez. Additional information can also be obtained from GeneCards, an electronic encyclopedia integrating information about genes and their products and biomedical applications from the Weizmann Institute of Science Genome and Bioinformatics (bioinformatics.weizmann.ac.il/cards), nucleotide sequence information can be also obtained from the EMBL Nucleotide Sequence Database (www.ebi.ac.uk/embl) or the DNA Databank or Japan (DDBJ, www.ddbi.nig.ac.jp). Additional sites for information on amino acid sequences include Georgetown's protein information resource website (www-.pir.georgetown.edu) and Swiss-Prot (au.expasy.org/sprot/sprot-top.html).

ii. Silencing Elements

In some embodiments, the polynucleotide of the polynucleotide delivery systems of the invention comprise a silencing element, wherein expression or introduction of the silencing element into a cell reduces the expression of a target polynucleotide or polypeptide encoded thereby.

As used herein, the terms "introduce" and "introducing" when referring to a polynucleotide or silencing element refers to the presentation of the polynucleotide or silencing element to a cell in such a manner that the polynucleotide or silencing element gains access to the intracellular region of the cell.

As used herein, the term "silencing element" refers to a polynucleotide, which when expressed or introduced into a cell is capable of reducing or eliminating the level of expression of a target polynucleotide sequence or the polypeptide encoded thereby.

The silencing element can comprise or encode an antisense oligonucleotide or an interfering RNA (RNAi). The term "interfering RNA" or "RNAi" refers to any RNA molecule which can enter an RNAi pathway and thereby reduce the expression of a target polynucleotide of interest. The RNAi pathway features the Dicer nuclease enzyme and RNA-induced silencing complexes (RISC) that function to degrade or block the translation of a target mRNA. RNAi is distinct from antisense oligonucleotides that function through "antisense" mechanisms that typically involve inhibition of a target transcript by a single-stranded oligonucleotide through an RNase H-mediated pathway. See, Crooke. (ed.) (2001) "*Antisense Drug Technology: Principles, Strategies, and Applications*" (1st ed), Marcel Dekker; ISBN: 0824705661; 1st edition.

As used herein, a "target polynucleotide" comprises any polynucleotide sequence that one desires to decrease the level of expression. By "reduces" or "reducing" the expression level of a polynucleotide or a polypeptide encoded thereby is intended to mean, the level of the polynucleotide or the encoded polypeptide is statistically lower than the target polynucleotide level or encoded polypeptide level in an appropriate control which is not exposed to the silencing element. In particular embodiments, reducing the target polynucleotide level and/or the encoded polypeptide level according to the presently disclosed subject matter results in less than 95%, less than 90%, less than 80%, less than 70%, less than 60%, less than 50%, less than 40%, less than 30%, less than 20%, less than 10%, or less than 5% of the target polynucleotide level, or the level of the polypeptide encoded thereby in an appropriate control. Methods to assay for the level of the RNA transcript, the level of the encoded polypeptide, or the activity of the polynucleotide or polypeptide are discussed elsewhere herein.

In some embodiments, the target polynucleotide is an oncogene or a proto-oncogene. The term "oncogene" is used herein in accordance with its art-accepted meaning to refer to those polynucleotide sequences that encode a gene product that contributes to cancer initiation or progression. The term "oncogene" encompasses proto-oncogenes, which are genes that do not contribute to carcinogenesis under normal circumstances, but that have been mutated, overexpressed, or activated in such a manner as to function as an oncogene. Non-limiting examples of oncogenes include growth factors or mitogens (e.g., c-Sis), receptor tyrosine kinases (e.g., epidermal growth factor receptor (EGFR), platelet-derived growth factor receptor (PDGFR), vascular endothelial growth factor receptor (VEGFR), HER2/neu), cytoplasmic tyrosine kinases (e.g., src, Abl) cytoplasmic serine/threonine kinases (e.g., raf kinase, cyclin-dependent kinases), regulatory GTPases (e.g., ras), and transcription factors (e.g., myc). In some embodiments, the target polynucleotide is EGFR.

The term "complementary" is used herein in accordance with its art-accepted meaning to refer to the capacity for precise pairing via hydrogen bonds (e.g., Watson-Crick base pairing or Hoogsteen base pairing) between two nucleosides, nucleotides or nucleic acids, and the like. For example, if a nucleotide at a certain position of a first nucleic acid is capable of stably hydrogen bonding with a nucleotide located opposite to that nucleotide in a second nucleic acid, when the nucleic acids are aligned in opposite 5' to 3' orientation (i.e., in anti-parallel orientation), then the nucleic acids are considered to be complementary at that position (where position may be defined relative to either end of either nucleic acid, generally with respect to a 5' end). The nucleotides located opposite one another can be referred to as a "base pair." A complementary base pair contains two complementary nucleotides, e.g., A and U, A and T, G and C, and the like, whereas a noncomplementary base pair contains two noncomplementary nucleotides (also referred to as a mismatch). Two polynucleotides are said to be complementary to each other when a sufficient number of corresponding positions in each molecule are occupied by nucleotides that hydrogen bond with each other, i.e., a sufficient number of base pairs are complementary.

As used herein, the term "gene" has its meaning as understood in the art. In general, a gene is taken to include gene regulatory sequences (e.g., promoters, enhancers, and the like) and/or intron sequences, in addition to coding sequences (open reading frames). It will further be appreciated that definitions of "gene" include references to nucleic acids that do not encode proteins but rather encode functional RNA molecules, or precursors thereof, such as microRNA or siRNA precursors, tRNAs, and the like.

The term "hybridize" as used herein refers to the interaction between two complementary nucleic acid sequences in which the two sequences remain associated with one another under appropriate conditions.

A silencing element can comprise the interfering RNA or antisense oligonucleotide, a precursor to the interfering RNA or antisense oligonucleotide, a template for the transcription of an interfering RNA or antisense oligonucleotide, or a template for the transcription of a precursor interfering RNA or antisense oligonucleotide, wherein the precursor is processed within the cell to produce an interfering RNA or antisense oligonucleotide. Thus, for example, a dsRNA silencing element includes a dsRNA molecule, a transcript or polyribonucleotide capable of forming a dsRNA, more than one transcript or polyribonucleotide capable of forming a dsRNA, a DNA encoding a dsRNA molecule, or a DNA encoding one strand of a dsRNA molecule. When the silencing element comprises a DNA molecule encoding an interfering RNA, it is recognized that the DNA can be transiently expressed in a cell or stably incorporated into the genome of the cell. Such methods are discussed in further detail elsewhere herein.

The silencing element can reduce or eliminate the expression level of a target polynucleotide or encoded polypeptide by influencing the level of the target RNA transcript, by influencing translation, or by influencing expression at the pre-transcriptional level (i.e., via the modulation of chromatin structure, methylation pattern, etc., to alter gene expression). See, for example, Verdel et al. (2004) *Science* 303:672-676; Pal-Bhadra et al. (2004) *Science* 303:669-672; Allshire (2002) *Science* 297:1818-1819; Volpe et al. (2002) *Science* 297:1833-1837; Jenuwein (2002) *Science* 297:2215-2218; and Hall et al. (2002) *Science* 297:2232-2237. Methods to assay for functional interfering RNA that are capable of reducing or eliminating the level of a sequence of interest are disclosed elsewhere herein.

Any region of the target polynucleotide can be used to design a domain of the silencing element that shares sufficient sequence identity to allow for the silencing element to decrease the level of the target polynucleotide or encoded polypeptide. For instance, the silencing element can be designed to share sequence identity to the 5' untranslated region of the target polynucleotide(s), the 3' untranslated region of the target polynucleotide(s), exonic regions of the target polynucleotide(s), intronic regions of the target polynucleotide(s), and any combination thereof.

The ability of a silencing element to reduce the level of the target polynucleotide can be assessed directly by measuring the amount of the target transcript using, for example, Northern blots, nuclease protection assays, reverse transcription (RT)-PCR, real-time RT-PCR, microarray analysis, and the like. Alternatively, the ability of the silencing element to reduce the level of the target polynucleotide can be measured directly using a variety of affinity-based approaches (e.g., using a ligand or antibody that specifically binds to the target polypeptide) including, but not limited to, Western blots, immunoassays, ELISA, flow cytometry, protein microarrays, and the like. In still other methods, the ability of the silencing element to reduce the level of the target polynucleotide can be assessed indirectly, e.g., by measuring a functional activity of the polypeptide encoded by the transcript or by measuring a signal produced by the polypeptide encoded by the transcript.

Various types of silencing elements are discussed in further detail below.

1) Double Stranded RNA Silencing Elements

In one embodiment, the silencing element comprises or encodes a double stranded RNA molecule. As used herein, a "double stranded RNA" or "dsRNA" refers to a polyribonucleotide structure formed either by a single self-complementary RNA molecule or a polyribonucleotide structure formed by the expression of least two distinct RNA strands. Accordingly, as used herein, the term "dsRNA" is meant to encompass other terms used to describe nucleic acid molecules that are capable of mediating RNA interference or gene silencing, including, for example, small RNA (sRNA), short-interfering RNA (siRNA), double-stranded RNA (dsRNA), micro-RNA (miRNA), hairpin RNA, short hairpin RNA (shRNA), and others. See, for example, Meister and Tuschl (2004) *Nature* 431:343-349 and Bonetta et al. (2004) *Nature Methods* 1:79-86.

In specific embodiments, at least one strand of the duplex or double-stranded region of the dsRNA shares sufficient sequence identity or sequence complementarity to the target polynucleotide to allow for the dsRNA to reduce the level of expression of the target polynucleotide or encoded polypeptide. As used herein, the strand that is complementary to the target polynkleotide is the "antisense strand," and the strand homologous to the target polynucleotide is the "sense strand."

In one embodiment, the dsRNA comprises a hairpin RNA. A hairpin RNA comprises an RNA molecule that is capable of folding back onto itself to form a double stranded structure. Multiple structures can be employed as hairpin elements. For example, the hairpin RNA molecule that hybridizes with itself to form a hairpin structure can comprise a single-stranded loop region and a base-paired stem. The base-paired stem region can comprise a sense sequence corresponding to all or part of the target polynucleotide and further comprises an antisense sequence that is fully or partially complementary to the sense sequence. Thus, the base-paired stem region of the silencing element can determine the specificity of the silencing. See, for example, Chuang and Meyerowitz (2000) *Proc. Natl. Acad. Sci. USA* 97:4985-4990, herein incorporated by reference. A transient assay for the efficiency of hpRNA constructs to silence gene expression in vivo has been described by Panstruga et al. (2003) *Mol. Biol. Rep.* 30:135-140, herein incorporated by reference.

2) siRNA Silencing Elements

A "short interfering RNA" or "siRNA" comprises an RNA duplex (double-stranded region) and can further comprise one or two single-stranded overhangs, e.g., 3' or 5' overhangs. The duplex can be approximately 19 base pairs (bp) long, although lengths between 17 and 29 nucleotides, including 17, 18, 19, 20, 21, 22, 23, 24, 25, 26, 27, 28, and 29 nucleotides, can be used. An siRNA can be formed from two RNA molecules that hybridize together or can alternatively be generated from a single RNA molecule that includes a self-hybridizing portion. The duplex portion of an siRNA can include one or more bulges containing one or more unpaired and/or mismatched nucleotides in one or both strands of the duplex or can contain one or more noncomplementary nucleotide pairs. One strand of an siRNA (referred to herein as the antisense strand) includes a portion that hybridizes with a target transcript. In certain embodiments, one strand of the siRNA (the antisense strand) is precisely complementary with a region of the target transcript over at least about 17 nucleotides, 18 nucleotides, 19 nucleotides, 20 nucleotides, 21 nucleotides, or more meaning that the siRNA antisense strand hybridizes to the target transcript without a single mismatch (i.e., without a single noncomplementary base pair) over that length. In other embodiments, one or more mismatches between the siRNA antisense strand and the targeted portion of the target transcript can exist. In embodiments in which perfect complementarity is not achieved, any mismatches between the siRNA antisense strand and the target transcript can be located at or near the 3' end of the siRNA antisense strand. For example, in certain embodiments, nucleotides 1-9, 2-9, 2-10, and/or 1-10 of the antisense strand are perfectly complementary to the target.

Considerations for the design of effective siRNA molecules are discussed in McManus et al. (2002) *Nature Reviews Genetics* 3: 737-747 and in Dykxhoorn et al. (2003) *Nature Reviews Molecular Cell Biology* 4: 457-467. Such considerations include the base composition of the siRNA, the position of the portion of the target transcript that is complementary to the antisense strand of the siRNA relative to the 5' and 3' ends of the transcript, and the like. A variety of computer programs also are available to assist with selection of siRNA sequences, e.g., from Ambion (web site having URL www.ambion.com), at the web site having the URL www.sinc.sunysb.edu/Stu/shilin/rnai.html. Additional design considerations that also can be employed are described in Semizarov et al. *Proc. Natl. Acad. Sci.* 100: 6347-6352.

3) Short Hairpin RNA Silencing Elements

The term "short hairpin RNA" or "shRNA" refers to an RNA molecule comprising at least two complementary portions hybridized or capable of hybridizing to form a double-stranded (duplex) structure sufficiently long to mediate RNAi (generally between approximately 17 and 29 nucleotides in length, including 17, 18, 19, 20, 21, 22, 23, 24, 25, 26, 27, 28, and 29 nucleotides in length, and in some embodiments, typically at least 19 base pairs in length), and at least one single-stranded portion, typically between approximately 1 and 20 or 1 to 10 nucleotides in length that forms a loop connecting the two nucleotides that form the base pair at one end of the duplex portion. The duplex portion can, but does not require, one or more bulges consisting of one or more unpaired nucleotides. In specific embodiments, the shRNAs comprise a 3' overhang. Thus, shRNAs are precursors of siRNAs and are, in general, similarly capable of inhibiting expression of a target transcript.

In particular, RNA molecules having a hairpin (stem-loop) structure can be processed intracellularly by Dicer to yield an siRNA structure referred to as short hairpin RNAs (shRNAs), which contain two complementary regions that hybridize to one another (self-hybridize) to form a double-stranded (duplex) region referred to as a stem, a single-stranded loop connecting the nucleotides that form the base pair at one end of the duplex, and optionally an overhang, e.g., a 3' overhang. The stem can comprise about 19, 20, or 21 bp long, though shorter and longer stems (e.g., up to about 29 nt) also can be used. The loop can comprise about 1-20, including 1, 2, 3, 4, 5, 6, 7, 8, 9, 10, 11, 12, 13, 14, 15, 16, 17, 18, 19, 20 nt, about 4-10, or about 6-9 nt. The overhang, if present, can comprise approximately 1-20 nt or approximately 2-10 nt. The loop can be located at either the 5' or 3' end of the region that is complementary to the target transcript whose inhibition is desired (i.e., the antisense portion of the shRNA).

Although shRNAs contain a single RNA molecule that self-hybridizes, it will be appreciated that the resulting duplex structure can be considered to comprise sense and antisense strands or portions relative to the target mRNA and can thus be considered to be double-stranded. It will therefore be convenient herein to refer to sense and antisense strands, or sense and antisense portions, of an shRNA, where the antisense strand or portion is that segment of the molecule that forms or is capable of forming a duplex with and is complementary to the targeted portion of the target polynucleotide, and the sense strand or portion is that segment of the molecule that forms or is capable of forming a duplex with the antisense strand or portion and is substantially identical in sequence to the targeted portion of the target transcript. In general, considerations for selection of the sequence of the antisense strand of an shRNA molecule are similar to those for selection of the sequence of the antisense strand of an siRNA molecule that targets the same transcript.

4) MicroRNA Silencing Elements

In one embodiment, the silencing element comprises or encodes an miRNA or an miRNA precursor. "MicroRNAs" or "miRNAs" are regulatory agents comprising about 19 ribonucleotides which are highly efficient at inhibiting the expression of target polynucleotides. See, for example, Saetrom et al. (2006) *Oligonucleotides* 16:115-144, Wang et al. (2006) *Mol. Cell.* 22:553-60, Davis et al. (2006) *Nucleic Acid Research* 34:2294-304, Pasquinelli (2006) *Dev. Cell* 10:419-24, all of which are herein incorporated by reference. For miRNA interference, the silencing element can be designed to express a dsRNA molecule that forms a hairpin structure containing a 19-nucleotide sequence that is complementary to the target polynucleotide of interest. The miRNA can be synthetically made, or transcribed as a longer RNA which is subsequently cleaved to produce the active miRNA. Specifically, the miRNA can comprise 19 nucleotides of the sequence having homology to a target polynucleotide in sense orientation and 19 nucleotides of a corresponding antisense sequence that is complementary to the sense sequence.

It is recognized that various forms of an miRNA can be transcribed including, for example, the primary transcript (termed the "pri-miRNA") which is processed through various nucleolytic steps to a shorter precursor miRNA (termed the "pre-miRNA"); the pre-miRNA; or the final (mature) miRNA, which is present in a duplex, the two strands being referred to as the miRNA (the strand that will eventually basepair with the target) and miRNA*. The pre-miRNA is a substrate for a form of dicer that removes the miRNA/miRNA* duplex from the precursor, after which, similarly to siRNAs, the duplex can be taken into the RISC complex. It has been demonstrated that miRNAs can be transgenically expressed and be effective through expression of a precursor form, rather than the entire primary form (McManus et al. (2002) *RNA* 8:842-50). In specific embodiments, 2-8 nucleotides of the miRNA are perfectly complementary to the target. A large number of endogenous human miRNAs have been identified. For structures of a number of endogenous miRNA precursors from various organisms, see Lagos-Quintana et al. (2003) *RNA* 9(2):175-9; see also Bartel (2004) *Cell* 116:281-297.

A miRNA or miRNA precursor can share at least about 80%, 85%, 90%, 91%. 92%, 93%, 94%, 95%, 96%, 97%, 98%, 99%, or 100% sequence complementarity with the target transcript for a stretch of at least about 15, 16, 17, 18, 19, 20, 21, 22, 23, 24, 25, 26, 27, 28, 29, or 30 nucleotides. In specific embodiments, the region of precise sequence complementarity is interrupted by a bulge. See, Ruvkun (2001) *Science* 294: 797-799, Zeng et al. (2002) *Molecular Cell* 9:1-20, and Mourelatos et al. (2002) *Genes Dev* 16:720-728.

5) Antisense Silencing Elements

In some embodiments, the silencing element comprises or encodes an antisense oligonucleotide. An "antisense oligonucleotide" is a single-stranded nucleic acid sequence that is wholly or partially complementary to a target polynucleotide, and can be DNA, or its RNA counterpart (i.e., wherein T residues of the DNA are U residues in the RNA counterpart).

The antisense oligonucleotides of this invention are designed to be hybridizable with target RNA (e.g., mRNA) or DNA. For example, an oligonucleotide (e.g., DNA oligonucleotide) that hybridizes to a mRNA molecule can be used to target the mRNA for RnaseH digestion. Alternatively, an oligonucleotide that hybridizes to the translation initiation site of an mRNA molecule can be used to prevent translation of the mRNA. In another approach, oligonucleotides that bind to double-stranded DNA can be administered. Such oligonucleotides can form a triplex construct and inhibit the transcription of the DNA. Triple helix pairing prevents the double helix from opening sufficiently to allow the binding of polymerases, transcription factors, or regulatory molecules. Recent therapeutic advances using triplex DNA have been described (see, e.g., J. E. Gee et al., 1994, Molecular and Immunologic Approaches, Futura Publishing Co., Mt. Kisco, N.Y.). Such oligonucleotides of the invention can be constructed using the base-pairing rules of triple helix formation and the nucleotide sequences of the target genes.

As non-limiting examples, antisense oligonucleotides can be targeted to hybridize to the following regions: mRNA cap region; translation initiation site; translational termination site; transcription initiation site; transcription termination site; polyadenylation signal; 3' untranslated region; 5' untranslated region; 5' coding region; mid coding region; and 3' coding region. In some embodiments, the complementary oligonucleotide is designed to hybridize to the most unique 5' sequence of a gene, including any of about 15-35 nucleotides spanning the 5' coding sequence.

Accordingly, the antisense oligonucleotides in accordance with this invention can comprise from about 10 to about 100 nucleotides, including, but not limited to about 10, 11, 12, 13, 14, 15, 16, 17, 18, 19, 20, 21, 22, 23, 24, 25, 30, 40, 50, 60, 70, 80, 90, or about 100 nucleotides.

Antisense nucleic acids can be produced by standard techniques (see, for example, Shewmaker et al., U.S. Pat. No. 5,107,065). Appropriate oligonucleotides can be designed using OLIGO software (Molecular Biology Insights, Inc., Cascade, Colo.; http://www.oligo.net).

6) Preparing Silencing Elements

Those of ordinary skill in the art will readily appreciate that a silencing element can be prepared according to any available technique including, but not limited to, chemical synthesis, enzymatic or chemical cleavage in vivo or in vitro, template transcription in vivo or in vitro, or combinations of the foregoing.

iii. Recombinant Expression Vectors and Host Cells

As discussed above, the silencing elements employed in the methods and compositions of the invention can comprise a DNA molecule which when transcribed produces an interfering RNA or a precursor thereof, or an antisense oligonucleotide. In such embodiments, the DNA molecule encoding the silencing element is found in an expression cassette. In addition, polynucleotides that comprise a coding sequence for a polypeptide of interest are found in an expression cassette.

The expression cassette comprises one or more regulatory sequences, selected on the basis of the cells to be used for expression, operably linked to a polynucleotide encoding the silencing element or polypeptide of interest. "Operably linked" is intended to mean that the nucleotide sequence of interest (i.e., a DNA encoding a silencing element or a coding sequence for a polypeptide of interest) is linked to the regulatory sequence(s) in a manner that allows for expression of the nucleotide sequence (e.g., in an in vitro transcription/translation system or in a cell when the expression cassette or vector is introduced into a cell). "Regulatory sequences" include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cells and those that direct expression of the nucleotide sequence only in certain host cells (e.g., tissue-specific regulatory sequences). It will be appreciated by those skilled in the art that the design of the expression cassette can depend on such factors as the choice of the host cell to be transformed, the level of expression of the silencing element or polypeptide of interest desired, and the like. Such expression cassettes typically include one or more appropriately positioned sites for restriction enzymes, to facilitate introduction of the nucleic acid into a vector.

It will further be appreciated that appropriate promoter and/or regulatory elements can readily be selected to allow expression of the relevant transcription units/silencing elements in the cell of interest. In certain embodiments, the promoter utilized to direct intracellular expression of a silencing element is a promoter for RNA polymerase III (Pol III). References discussing various Pol III promoters, include, for example, Yu et al. (2002) *Proc. Natl. Acad. Sci.* 99(9), 6047-6052; Sui et al. (2002) *Proc. Natl. Acad. Sci.* 99(8), 5515-5520 (2002); Paddison et al. (2002) *Genes and Dev.* 16, 948-958; Brummelkamp et al. (2002) *Science* 296, 550-553; Miyagashi (2002) *Biotech.* 20, 497-500; Paul et al. (2002) *Nat. Biotech.* 20, 505-508; Tuschl et al. (2002) *Nat. Biotech.* 20, 446-448. According to other embodiments, a promoter for RNA polymerase I, e.g., a tRNA promoter, can be used. See McCown et al. (2003) *Virology* 313(2):514-24; Kawasaki (2003) *Nucleic Acids Res.* 31 (2):700-7. In some embodiments in which the polynucleotide comprises a coding sequence for a polypeptide of interest, a promoter for RNA polymerase II can be used.

The regulatory sequences can also be provided by viral regulatory elements. For example, commonly used promoters are derived from polyoma, Adenovirus 2, cytomegalovirus, and Simian Virus 40. For other suitable expression systems for both prokaryotic and eukaryotic cells, see Chapters 16 and 17 of Sambrook et al. (1989) *Molecular Cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.).

In vitro transcription can be performed using a variety of available systems including the T7, SP6, and T3 promoter/polymerase systems (e.g., those available commercially from Promega, Clontech, New England Biolabs, and the like). Vectors including the T7, SP6, or T3 promoter are well known in the art and can readily be modified to direct transcription of silencing elements. When silencing elements are synthesized in vitro, the strands can be allowed to hybridize before introducing into a cell or before administration to a subject. As noted above, silencing elements can be delivered or introduced into a cell as a single RNA molecule including self-complementary portions (e.g., an shRNA that can be processed intracellularly to yield an siRNA), or as two strands hybridized to one another. In other embodiments, the silencing elements employed are transcribed in vivo. As discussed elsewhere herein, regardless of if the silencing element is transcribed in vivo or in vitro, in either scenario, a primary transcript can be produced which can then be processed (e.g., by one or more cellular enzymes) to generate the interfering RNA that accomplishes gene inhibition.

In those embodiments in which the silencing element is an interfering RNA, the interfering RNA can be generated by transcription from a promoter, either in vitro or in vivo. For instance, a construct can be provided containing two separate transcribable regions, each of which generates a 21 nt transcript containing a 19 nt region complementary with the other. Alternatively, a single construct can be utilized that contains opposing promoters and terminators positioned so that two different transcripts, each of which is at least partly complementary to the other, are generated. Alternatively, an RNA-inducing agent can be generated as a single transcript, for example by transcription of a single transcription unit encoding self complementary regions. A template is employed that includes first and second complementary regions, and optionally includes a loop region connecting the portions. Such a template can be utilized for in vitro transcription or in vivo transcription, with appropriate selection of promoter and, optionally, other regulatory elements, e.g., a terminator.

In some embodiments, the polynucleotide delivery system comprises a cytotoxic polynucleotide delivery system. As used herein, a "cytotoxic polynucleotide delivery system" is one that has cytotoxic activity, as defined herein. The lipid vehicle of the cytotoxic polynucleotide delivery system comprises a cationic lipid of formula (I). The cytotoxic activity of the cytotoxic polynucleotide delivery system can be imparted from a cytotoxic cationic lipid of formula (I), a cytotoxic polynucleotide, or both. A "cytotoxic polynucleotide" has cytotoxic activity when expressed or introduced into a cell. Non-limiting examples of cytotoxic polynucleotides include polynucleotides that encode a polypeptide that is able to induce cell death, such as an apoptosis-inducing gene. Other cytotoxic polynucleotides include polynucleotides that comprise a silencing element that when expressed or introduced into a cell reduces the expression of a target polynucleotide that is essential for cellular survival or growth. For example, a silencing element that targets the epidermal growth factor receptor has cytotoxic activity. Thus, in some embodiments, the cytotoxic lipid/polynucleotide delivery system comprises a lipid vehicle encapsulating a cytotoxic polynucleotide, wherein the lipid vehicle comprises a cytotoxic cationic lipid of formula (I).

b. Polypeptides of Interest

In some embodiments, the presently disclosed delivery systems comprise a lipid vehicle encapsulating a polypeptide of interest that is to be delivered to a cell. The delivery systems disclosed herein are capable of introducing a polypeptide into the intracellular region of a cell. Importantly, targeted delivery systems comprising a lipid vehicle encapsulating a polypeptide are capable of specifically delivering a given polypeptide into a cell.

In some embodiments, the delivery system capable of delivering a polypeptide of interest into a cell comprises a cationic liposome encapsulating the polypeptide. In certain embodiments, the cationic liposome comprises the cationic lipid DOTAP and the co-lipid cholesterol in a 1:1 molar ratio. In some of these embodiments, the polypeptide that is delivered into the cell comprises an anionic polypeptide. As used herein, an "anionic polypeptide" is a polypeptide as described herein that has a net negative charge at physiological pH. The anionic polypeptide can comprise at least about 20%, 30%, 40%, 50%, 60%, 70%, 75%, 80%, 85%, 90%, 95%, 96%, 97%, 98%, 99%, or 100% amino acid residues that have a negative charge at physiological pH. These include aspartic acid (D), asparagine (N), glutamic acid (E), and glutamine (Q).

In particular embodiments, the polypeptide of interest is acetylated at the amino and/or carboxyl termini to enhance the negative charge of the polypeptide. In some embodiments, the delivery system further comprises a polycation, as described elsewhere herein. In other embodiments, the delivery system comprises a polyanionic carrier macromolecule, such as heparin sulfate. In particular embodiments, the delivery system comprises a LPH nanoparticle, which comprises a cationic liposome encapsulating a polypeptide of interest, heparin sulfate, and a polycation (e.g., protamine). In some of these embodiments, the polypeptide comprises an anionic polypeptide. In certain embodiments, the delivery system comprises a cationic liposome encapsulating an anionic polypeptide, and optionally a polyanionic carrier macromolecule (e.g., heparin sulfate) and a polycation (e.g., protamine) and the surface charge of the cationic liposome is shielded by the post-insertion of lipid-polyethylene glycol conjugates into the lipid bilayer of the liposome. In some of these embodiments, the delivery system is a stealth delivery system. To provide specific targeting to a targeted cell or tissue, the outer leaflet of the lipid bilayer of the liposome of the delivery system can further comprise a targeting ligand.

In some embodiments, the delivery systems comprising a polypeptide of interest comprise polypeptides of interest having at least about 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, 500, or more amino acid residues. In some embodiments, the polypeptide of interest comprises between about 5 and about 50 amino acid residues.

In some embodiments, the polypeptide of interest is cytotoxic. In some of these embodiments, the polypeptide of interest is capable of blocking an essential intracellular signaling event upon delivery to a cell.

3. Polycation

In some embodiments, the delivery system can further comprise a polycation, wherein the lipid vehicle encapsulates said polycation. Polycations can physically associate with an anionic bioactive compound, such as a polynucleotide, by the attraction of opposite charges. Thus, in some embodiments in which the delivery system comprises a polycation, the anionic bioactive compound is a polynucleotide. In those embodiments in which the lipid vehicle of the delivery system comprises a cationic liposome and the bioactive compound is a polynucleotide, and wherein the delivery system further comprises a polycation that physically associates with the polynucleotide within the core of the cationic liposome, the resulting complex can be referred to as a "lipid/polycation/polynucleotide nanoparticle" or "LPP". The polynucleotide component of the "lipid/polycation/polynucleotide nanoparticle" or "LPP" can be DNA or RNA (see, for example, U.S. Pat. No. 5,795,587 and U.S. Pat. No. 6,008,202, herein incorporated by reference). In those embodiments in which the polyanionic carrier macromolecule of the LPP nanoparticle comprises hyaluronic acid or heparin sulfate, the complex is referred to as a "lipid/polycation/hyaluronic acid (or heparin sulfate) nanoparticle" or "LPH nanoparticle" or "LPH-NP." In certain embodiments, the overall net charge of the lipid/polycation/polynucleotide nanoparticle is positive at physiological pH.

Without being bound by any theory or mechanism of action, it is believed that the polycation serves to condense the polynucleotide, allowing the size of the delivery system complex to be reduced as compared to those polynucleotide delivery system complexes that lack a polycation, and contributes to the stabilization of the overall complex. Likewise, polycations serve to associate with and condense other anionic bioactive compounds. In general, LPP nanoparticles are about 100 nm in diameter. In particular non-limiting embodiments, the LPP nanoparticles have a diameter of about 50 nm, about 60 nm, about 70 nm, about 80 nm, about 90 nm, about 100 nm, about 125, about 150, about 175, about 200 nm, about 225 nm, or about 250 nm.

As used herein, a "polycation" refers to a macromolecule with many positively charged groups that are positively charged at physiological pH. The polycation can be selected from organic polycations having a molecular weight of between about 300 and about 200,000. In some embodiments, these polycations have a valence of between about 3 and about 1000 at pH 7.0. Polycations can include, but are not limited to, natural or synthetic amino acids, peptides, polypeptides, polyamines, carbohydrates and any synthetic cationic polymers. Non-limiting examples of polycations include polyarginine, polyornithine, protamines and polylysine, polybrene (hexadimethrine bromide), histone, cationic dendrimer, spermine, spermidine and synthetic polypeptides derived from SV40 large T antigen that have excess positive charges and represent a nuclear localization signal.

In some embodiments, the polycation is a polycationic polypeptide having an amino acid composition in which arginine residues comprise at least 30% of the amino acid residues of the polypeptide and lysine residues comprise less than 5% of the amino acid residues of the polypeptide. In certain embodiments, histidine, lysine and arginine together make up from about 45% to about 85% of the amino acid residues of the polypeptide and serine, threonine and glycine make up from about 10% to about 25% of the amino acid residues of the polypeptide. In still other embodiments, arginine residues constitute from about 65% to about 75% of the amino acid residues of the polypeptide and lysine residues constitute from about 0 to about 3% of the amino acid residues of the polypeptide.

In addition to the above recited percentages of arginine and lysine residues, the polycationic polypeptides can also contain from about 20% to about 30% hydrophobic residues, or about 25% hydrophobic residues. The polycationic polypeptide to be used in producing polynucleotide delivery system complexes can be up to 500 amino acids in length, from about 20 to about 100 amino acids in length, or from about 25 to about 50 amino acids in length, and in other embodiments, from about 25 to about 35 amino acids in length.

In one embodiment, the arginine residues present in the polycationic polypeptide are found in clusters of 3-8 contiguous arginine residues or in clusters of 4-6 contiguous arginine residues.

In another embodiment, the polycationic polypeptide is about 25 to about 35 amino acids in length and about 65 to about 70% of its residues are arginine residues and 0 to 3% of its residues are lysine residues.

The polycationic polypeptides to be used in formulating the complexes of the invention can be provided as naturally occurring proteins, particularly certain protamines having a high arginine to lysine ratio as discussed above, as a chemically synthesized polypeptide, as a recombinant polypeptide expressed from a nucleic acid sequence which encodes the polypeptide, or as a salt of any of the above polypeptides where such salts include, but are not limited to, phosphate, chloride and sulfate salts. In certain embodiments, the polycation comprises protamine sulfate.

In some embodiments, the lipid/polycation/polynucleotide nanoparticle comprises a cytotoxic lipid/polycation/polynucleotide nanoparticle. As used herein, a "cytotoxic lipid/polycation/polynucleotide nanoparticle" is one that has cytotoxic activity, as described elsewhere herein. The lipid vehicle of the cytotoxic lipid/polycation/polynucleotide nanoparticle comprises a cationic lipid of formula (I). The cytotoxic activity of the cytotoxic LPP nanoparticle can be imparted from a cytotoxic cationic lipid of formula (I), a cytotoxic polynucleotide, or both. Thus, in some embodiments, the cytotoxic lipid/polycation/polynucleotide nanoparticle comprises a lipid vehicle encapsulating a polycation and a cytotoxic polynucleotide, wherein the lipid vehicle comprises a cytotoxic cationic lipid of formula (I). Methods for generating LPP nanoparticles and cytotoxic LPP nanoparticles are described elsewhere herein.

4. Polyanionic Carrier Macromolecules

The present invention embodies delivery systems comprising a cationic lipid of formula (I). In some embodiments in which the lipid vehicle of the delivery system comprises a cationic liposome, the complex further comprises a polyanionic carrier macromolecule that is encapsulated by the lipid vehicle, wherein the polyanionic carrier macromolecule aids in the delivery of the polynucleotide. A "polyanionic carrier macromolecule" refers to any molecule that carries more than one negative charge at physiological pH (e.g., multivalent) that can interact with the cationic lipids of the cationic liposome of a delivery system through charge-charge interactions in such a way as to allow the delivery system to deliver the encapsulated bioactive compound to a cell, either in an in vitro or in vivo system. The ability of a delivery system to deliver an encapsulated bioactive compound to a cell can be measured using assays described elsewhere herein (see, for example, Experimental Examples 2 and 3). In some embodiments, the polyanionic carrier macromolecule has a molecular weight of between about 5 and about 20,000 kDa, including but not limited to, about 5 kDa, about 10 kDa, about 20 kDa, about 30 kDa, about 40 kDa, about 50 kDa, about 60 kDa, about 70 kDa, about 80 kDa, about 90 kDa, about 100 kDa, about 200 kDa, about 300 kDa, about 400 kDa, about 500 kDa, about 600 kDa, about 700 kDa, about 800 kDa, about 900 kDa, about 1,000 kDa, about 5,000 kDa, about 10,000 kDa, and about 20,000 kDa.

In some embodiments, the polyanionic carrier macromolecule has a valence of between about 20 and about 100,000, including but not limited to, about 20, about 30, about 40, about 50, about 60, about 70, about 80, about 90, about 100, about 500, about 1,000, about 10,000, and about 100,000 at physiological pH. Non-limiting examples of polyanionic carrier macromolecules include polymers, such as polyanionic polysaccharides, polyanionic polypeptides, and combinations thereof (e.g., glycoproteins, proteoglycans), and polyanionic polynucleotides. The polyanionic carrier macromolecules may be naturally occurring (i.e., one existing in nature without human intervention), chemically synthesized, or in the case of polynucleotides, may be a recombinant polynucleotide (i.e., one existing only with human intervention).

In some embodiments, the polyanionic carrier macromolecule comprises a carrier polynucleotide, wherein a carrier polynucleotide is a polynucleotide that can be used in polynucleotide delivery systems to enhance the delivery of a polynucleotide of interest to a cell. Generally, unlike the polynucleotide of interest, once delivered to a cell, the carrier polynucleotide does not exert a desired phenotypic change in a cell (e.g., a therapeutic effect, expression of a polypeptide of interest, a change in the expression level of an endogenous gene when delivered to a cell in vitro or in vivo). Non-limiting examples of carrier polynucleotides are genomic DNA (e.g., calf thymus DNA) and bacterially produced plasmid DNA. In some embodiments, the polyanionic carrier macromolecule is calf thymus DNA.

In some embodiments, the polyanionic carrier macromolecule comprises a polyanioinic carrier polysaccharide. The term "polysaccharide" refers to a carbohydrate molecule comprised of two or more monomers (monosaccharides)

joined together by glycosidic bonds. Thus, disaccharides, trisaccharides, oligosaccharides, or any other term used to refer to a carbohydrate molecule comprising more than one monosaccharides linked together by glycosidic bonds are included within the definition of "polysaccharide," and the term "polysaccharide" can be used instead of, or interchangeably with any of these terms. The term "polysaccharide" encompasses both homopolysaccharides (a polysaccharide comprised of only one type of monosaccharide) and heteropolysaccharides (a polysaccharide comprising more than one type of monosaccharide). A heteropolysaccharide can include polysaccharides comprised of repeating disaccharide units, trisaccharide units, tetrasaccharide units, or a repeating unit of any length. A "polyanionic polysaccharide" is a polysaccharide comprising a multiplicity of negative charges at physiological pH. In some embodiments, the polyanionic polysaccharide comprises 2 to 2000 monosaccharide units, including but not limited to, about 2, about 5, about 10, about 20, about 30, about 40, about 50, about 60, about 70, about 80, about 90, about 100, about 125, about 150, about 175, and about 200 monosaccharide units. In some embodiments, about 10%, about 20%, about 30%, about 40%, about 50%, about 60%, about 70%, about 80%, about 90%, about 100% of the monosaccharide units that make up the polyanionic macromolecules have at least one negative charge.

In some embodiments, the polyanionic carrier polysaccharide comprises a polyanionic glycosaminoglycan. A glycosaminoglycan is an unbranched polysaccharide comprising repeating disaccharide units, wherein one of the monosaccharide units of the disaccharide comprises an amino sugar, including, but not limited to, D-galactosamine or D-glucosamine. In some embodiments, the other monosaccharide unit of the repeating disaccharide comprises a uronic acid, including but not limited to D-glucuronic acid. (GlcA) or L-iduronic acid (IdoA). In general, at least one of the monosaccharide monomers of the disaccharide unit has a negatively charged side group (e.g., carboxylate, sulfate). In some of these embodiments, the glycosaminoglycan comprises heparin, heparin sulfate, hyaluronic acid, chondroitin sulfate, dermatin sulfate, and dextran sulfate. In certain embodiments, the glycosaminoglycan comprises hyaluronic acid. In some embodiments, the glycosaminoglycan is not heparin or heparin sulfate.

In other embodiments, the polyanionic carrier macromolecule comprises a polyanionic carrier polypeptide. A "polyanionic polypeptide" is a polypeptide, as defined elsewhere herein, comprising a multiplicity of negative charges at physiological pH. Unlike a polypeptide of interest, a polyanionic carrier polypeptide does not exert a desired phenotypic change in a cell upon delivery to the cell. The polyanionic carrier polypeptides may comprise glutamic acid residues, aspartic acid residues, or both. In some embodiments, the polyanionic carrier polypeptide has an amino acid composition in which glutamic acid residues, aspartic acid residues or both residues comprise at least 30% of the amino acid residues of the polypeptide, at least 40% of the amino acid residues of the polypeptide, at least 50% of the amino acid residues of the polypeptide, at least 60% of the amino acid residues of the polypeptide, at least 70% of the amino acid residues of the polypeptide, at least 80% of the amino acid residues of the polypeptide, at least 90% of the amino acid residues of the polypeptide, at least 95% of the amino acid residues of the polypeptide, at least 96% of the amino acid residues of the polypeptide, at least 97% of the amino acid residues of the polypeptide, at least 98% of the amino acid residues of the polypeptide, at least 99% of the amino acid residues of the polypeptide, or at least 100% of the amino acid residues of the polypeptide.

In some embodiments, the polyanionic carrier polypeptide is from about 2 amino acids to about 100,000 amino acids in length, including but not limited to about 2, about 5, about 10, about 20, about 30, about 40, about 50, about 60, about 70, about 80, about 90, about 100, about 200, about 500, about 1,000, about 10,000, about 50,000, and about 100,000 amino acids in length.

The polyanionic carrier polypeptides to be used in formulating the complexes of the invention can be provided as naturally occurring proteins, as a chemically synthesized polypeptide, as a recombinant polypeptide expressed from a nucleic acid sequence which encodes the polypeptide, or as a salt of any of the above polypeptides where such salts include, but are not limited to, phosphate, chloride and sulfate salts.

In certain embodiments, the polyanionic carrier macromolecule comprises a polyanionic proteoglycan or a polyanionic glycopeptide. A proteoglycan comprises a glycosaminoglycan covalently bound to a polypeptide. Polyanionic proteoglycans may be comprised of a polyanionic glycosaminoglycan bound to a non-polyanionic (e.g., neutral, cationic) or a polyanionic polypeptide. A glycopeptide comprises a monosaccharide or polysaccharide covalently bound to a polypeptide. Polyanionic glycopeptides may be comprised of a polyanionic polysaccharide bound to a non-polyanionic polypeptide, a non-polyanionic polysaccharide bound to a polyanionic polypeptide, or a polyanionic polysaccharide bound to a polyanionic polypeptide.

In some embodiments, the molar ratio of the polyanionic carrier macromolecule to the polynucleotide of interest (polyanionic carrier macromolecule:polynucleotide of interest) comprises about 1:1 to about 100:1, including but not limited to about 1:1, about 2:1, about 3:1, about 4:1, about 5:1, about 6:1, about 7:1, about 8:1, about 9:1, about 10:1, about 20:1, about 30:1, about 40:1, about 50:1, about 60:1, about 70:1, about 80:1, about 90:1, and about 100:1.

5. PEGylated Delivery Systems

In some embodiments, the surface charge of the lipid vehicle of the delivery system can be minimized by incorporating lipids comprising polyethylene glycol (PEG) moieties into the lipid vehicle. Reducing the surface charge of the lipid vehicle of the delivery system can reduce the amount of aggregation between the delivery system complexes and serum proteins and enhance the circulatory half-life of the complex (Yan, Scherphof, and Kamps (2005) *J Liposome Res* 15:109-139). Thus, in some embodiments, the exterior surface of the lipid vehicle of the delivery system comprises a PEG molecule. Such complexes are referred to herein as a PEGylated delivery system. The PEGylated delivery system can be generated through the post-insertion of a lipid-PEG conjugate into the lipid vehicle of the delivery system through incubation of the delivery system with micelles comprising lipid-PEG conjugates, as known in the art and described elsewhere herein (Ishida et al. (1999) *FEBS Lett.* 460:129-133; Perouzel et al. (2003) *Bioconjug. Chem.* 14:884-898; see Experimental section). By "lipid-polyethylene glycol conjugate" or "lipid-PEG conjugate" is intended a lipid molecule that is covalently bound to at least one polyethylene glycol molecule. In some embodiments, the lipid-PEG conjugate comprises 1,2-distearoyl-sn-glycero-3-phosphoethanolamine-N-carboxy-polyethylene glycol (DSPE-PEG). As described immediately below, these lipid-PEG conjugates can be further modified to include a targeting ligand (e.g., DSPE-PEG-AA). The term "lipid-PEG conjugate" also refers to these lipid-PEG-targeting ligand conjugates and delivery systems comprising lipid vehicle comprising a lipid-PEG targeting ligand conjugate are considered to be PEGylated and targeted delivery systems, as described immediately below.

PEGylation of lipid vehicles enhances the circulatory half-life of the delivery system by reducing clearance of the delivery system complex by the reticuloendothelial (RES) system. While not being bound by any particular theory or mechanism of action, it is believed that a PEGylated lipid vehicle can evade the RES system by sterically blocking the opsonization of the particles (Owens and Peppas (2006) *Int J Pharm* 307: 93-102). In order to provide enough steric hindrance to avoid opsonization, the exterior surface of the lipid vehicle must be completely covered by PEG molecules in the "brush" configuration. At low surface coverage, the PEG chains will typically have a "mushroom" configuration, wherein the PEG molecules will be located closer to the surface of the lipid vehicle. In the "brush" configuration, the PEG molecules are extended further away from the particle surface, enhancing the steric hindrance effect. However, over-crowdedness of PEG on the surface may decrease the mobility of the polymer chains and thus decrease the steric hindrance effect (Owens and Peppas (2006) *Int J Pharm* 307:93-102). The conformation of PEG depends upon the surface density and the molecular mass of the PEG on the surface of the lipid vehicle. The controlling factor is the distance between the PEG chains on the vehicle surface (D) relative to their Flory dimension, $R_F$, which is defined as $\alpha N^{3/5}$, wherein $\alpha$ is the persistence length of the monomer, and N is the number of monomer units in the PEG (Nicholas et al. (2000) *Biochim Biophys Acta* 1463:167-178). Three regimes can be defined: (1) when $D>2 R_F$ (interdigitated mushrooms); (2) when $D<2 R_F$ (mushrooms); and (3) when $D<R_F$ (brushes) (Nicholas et al.).

In certain embodiments, the PEGylated delivery system comprises a stealth delivery system. By "stealth delivery system" is intended a delivery system comprising a lipid vehicle, wherein the exterior surface of the lipid vehicle comprises a sufficient number of PEG molecules in a configuration that allows the delivery system to exhibit a reduced uptake by the RES system in the liver as compared to non PEGylated delivery systems when administered to a subject. RES uptake can be measured using assays known in the art, including, but not limited to the liver perfusion assay described elsewhere herein (see Experimental Example 4). In some of these embodiments, the stealth delivery system comprises a lipid vehicle, wherein the exterior surface of the lipid vehicle comprises PEG molecules, wherein said $D<R_F$.

In those embodiments in which the PEGylated delivery system is a stealth delivery system, the outer leaflet of the lipid bilayer of the cationic liposome comprises a lipid-PEG conjugate at a concentration of about 4 mol % to about 15 mol % of the outer leaflet lipids, including, but not limited to, about 4 mol %, about 5 mol %, about 6 mol %, about 7 mol %, 8 mol %, about 9 mol %, about 10 mol %, about 11 mol %, about 12 mol %, about 13 mol %, about 14 mol %, and about 15 mol % PEG. In certain embodiments, the outer leaflet of the lipid bilayer of the cationic liposome of the stealth polynucleotide delivery system comprises about 10.6 mol % PEG. The polyethylene glycol moiety of the lipid-PEG conjugate can have a molecular weight ranging from about 100 to about 20,000 g/mol, including but not limited to about 100 g/mol, about 200 g/mol, about 300 g/mol, about 400 g/mol, about 500 g/mol, about 600 g/mol, about 700 g/mol, about 800 g/mol, about 900 g/mol, about 1000 g/mol, about 5000 g/mol, about 10,000 g/mol, about 15,000 g/mol, and about 20,000 g/mol. In some of these embodiments, the lipid-PEG conjugate comprises a PEG molecule having a molecular weight of about 2000 g/mol. In certain embodiments, the lipid-PEG conjugate comprises DSPE-PEG$_{2000}$.

6. Delivery Systems with a Supported Bilayer

The delivery system of the invention can comprise a supported bilayer. A delivery system comprising a supported bilayer can be PEGylated, for example, through a post-insertion step to neutralize the surface charge and reduce RES uptake, limiting non-specific binding and enhancing the pharmacokinetic properties of the delivery system. A "supported bilayer" when referring to a delivery system is a bilayer, wherein one or both of the leaflets (e.g., inner leaflet, outer leaflet) of the bilayer has been sufficiently stabilized through an electrostatic force or covalent bonding to allow the bilayer to remain intact while incorporating a high enough percentage of lipid-PEG conjugates to completely shield the surface charge (e.g., the zeta potential of the liposome has a zeta potential of about 0) or to reduce the RES uptake of the PEGylated delivery system when compared to a delivery system lacking PEG. A bilayer is said to "remain intact" when there is not a substantial increase in the permeability of the lipid bilayer, which can be measured using techniques known in the art (Nicholas et al. (2000) *Biochim. Biophys. Acta* 1463:167-178), or a substantial increase in the small particle population (e.g., less than 50 nm, not including lipid-PEG micelles), which can be measured using techniques known in the art.

In some embodiments, the supported bilayer comprises a "core supported bilayer." By "core supported bilayer" is intended a bilayer that has been stabilized through an electrostatic or covalent interaction between members of the bilayer and the contents of the inner core of the lipid vehicle. A non-limiting example of a delivery system comprising a lipid vehicle comprising a core supported bilayer is the LPP nanoparticle described herein, wherein the negatively charged components of the liposome core (e.g., polynucleotide of interest, polyanioinic carrier macromolecule) interact with the cationic lipids of the cationic liposome through charge-charge interactions.

In other embodiments, the supported bilayer comprises a leaflet supported bilayer. As used herein, a "leaflet supported bilayer" comprises a bilayer that has been stabilized through electrostatic or covalent interactions between members of the leaflets that comprise the bilayer (e.g., inner leaflet, outer leaflet). A covalent leaflet supported bilayer refers to a covalent bilayer as described in PCT International Patent Application Serial No. PCT/US2009/042485, entitled "Methods and Compositions for the Delivery of Bioactive Compounds," filed concurrently herewith and herein incorporated by reference in its entirety, that is sufficiently stabilized through covalent bonding between at least two amphipathic molecules within the inner leaflet, between at least two amphipathic molecules within the outer leaflet, or between at least two amphipathic molecules within the inner leaflet and between at least two amphipathic molecules within the outer leaflet to allow the bilayer to remain intact while incorporating a high enough percentage of lipid-PEG conjugates to completely shield the surface charge (e.g., the zeta potential of the lipid vehicle has a zeta potential of about 0) or to reduce the RES uptake of the PEGylated delivery system when compared to a delivery system lacking PEG. The leaflet supported bilayer, wherein the stability is imparted by interactions between the members of the bilayer is distinct from a core supported bilayer, wherein the stability is imparted by interactions between members of the bilayer and the components of the vehicle core. However, a delivery system could comprise a supported bilayer, wherein the support is imparted from both the interactions between components of the bilayer (a leaflet supported bilayer) and from interactions between the core components and the bilayer (a core supported bilayer). An example of such a delivery system is a covalent leaflet supported bilayer as described herein, wherein the hydrophilic head groups or side chains within the inner leaflet of the bilayer are cationic and there exists a charge-charge interaction between these cationic amphipathic molecules of the inner leaflet and an anionic bioactive agent present within the core of the lipid vehicle.

It should be understood that in some embodiments of the invention, a delivery system comprising a leaflet supported bilayer can be one in which the members of the inner leaflet of the bilayer interact with members of the outer leaflet of the bilayer.

In some of those embodiments in which the supported bilayer has been stabilized through covalent bonds between members of the bilayer and the contents of the inner core of the lipid vehicle or between the amphipathic molecules within the leaflets of the bilayer, the covalent bonds comprise biocleavable covalent bonds. Biocleavable bonds are those that can be cleaved or broken upon entering a cell or an organism. The presence of biocleavable covalent bonds facilitates the release of the encapsulated bioactive compound.

In some embodiments, the biocleavable covalent bonds are those that are more specifically cleaved after entering the cell (intracellular cleavage). In some embodiments, the biocleavable covalent bonds are cleavable in acidic conditions like those found in lysosomes. One non-limiting example is an acid-sensitive (or acid-labile) hydrazone linkage, such as an acylhydrazone bond as described by Greenfield et al. (1990) Cancer Res. 50, 6600-6607, which is herein incorporated by reference in its entirety. Another non-limiting example is certain linkages or bonds subject to hydrolysis that include various aldehyde bonds with amino or sulfhydryl groups. Also included are amide bonds such as when N-hydroxysuccinimide ester (NHS ester) reacts with amines. Another non-limiting example is an acid-labile maleamate bond (see Rozema et al. (2007) Proc Natl Acad Sci USA 104:12982-12987, which is herein incorporated by reference in its entirety). In certain embodiments, the biocleavable covalent bonds are cleavable by enzymes more commonly found in endosomes or lysosomes, such as lysosomal acid hydrolases.

It is to be understood that the present invention encompasses any delivery system comprising a lipid vehicle that encapsulates a bioactive compound (e.g., polynucleotide, polypeptide, small molecule, drug) and is capable of delivering the bioactive compound to a cell or tissue, wherein the lipid vehicle comprises a supported bilayer and a cationic lipid of formula (I). In some embodiments, the delivery system comprises a polynucleotide delivery system as described herein, including but not limited to, a LPP or LPH nanoparticle.

7. Targeted Delivery Systems

In some embodiments, the delivery systems comprise a lipid vehicle wherein the exterior surface of the lipid vehicle comprises a targeting ligand, forming a targeted delivery system. As discussed herein, a targeting ligand is a molecule that targets a physically associated molecule or complex to a targeted cell or tissue. Thus, a "targeted delivery system" is one in which the exterior surface of the lipid vehicle of the delivery system comprises a targeting ligand that targets the targeted delivery system to a targeted cell or tissue. In certain embodiments, the targeting ligand comprises a benzamide derivative. In some of these embodiments, the benzamide derivative comprises anisamide.

The targeting ligand can be covalently bound to the cationic lipids of formula (I) described herein, other cationic lipids, or co-lipids comprising the lipid vehicle of the delivery system, forming a lipid-targeting ligand conjugate. Some lipid-targeting ligand conjugates comprise an intervening molecule in between the lipid and the targeting ligand, which is covalently bound to both the lipid and the targeting ligand. In some of these embodiments, the intervening molecule is polyethylene glycol (PEG), thus forming a lipid-PEG-targeting ligand conjugate. An example of such a lipid-targeting conjugate is DSPE-PEG-AA, in which the lipid 1,2-distearoyl-sn-glycero-3-phosphoethanolamine-N-carboxyl (DSPE) is bound to polyethylene glycol (PEG), which is bound to the targeting ligand anisamide (AA). Thus, in some embodiments, the lipid vehicle of the targeted delivery system comprises the lipid-targeting ligand conjugate DSPE-PEG-AA.

In certain embodiments, the targeting ligand targets the targeted delivery system to a targeted cell, wherein the targeted cell is a cancer cell. In some of these embodiments, including those in which the targeting ligand is anisamide, the cancer cell is a lung cancer cell.

C. Pharmaceutical Compositions

The lipids and delivery systems of the invention are useful in mammalian tissue culture systems, in animal studies, and for therapeutic purposes. The cytotoxic cationic lipids of formula (I), and delivery systems comprising a cationic lipid of formula (I), wherein the cationic lipids of formula (I) have cytotoxic activity, delivery systems comprising a cationic lipid of formula (I), wherein the bioactive compound has therapeutic activity, and delivery systems comprising a cytotoxic cationic lipid of formula (I) and a bioactive compound with therapeutic activity can be used in therapeutic applications. The presently disclosed subject matter therefore provides pharmaceutical compositions comprising cytotoxic cationic lipids of formula (I) or delivery systems comprising cationic lipids of formula (I).

The presently disclosed compositions can be formulated for delivery, i.e., administering to the subject, by any available route including, but not limited to, parenteral (e.g., intravenous), intradermal, subcutaneous, oral, nasal, bronchial, opthalmic, transdermal (topical), transmucosal, rectal, and vaginal routes. In some embodiments, the route of delivery is intravenous, parenteral, transmucosal, nasal, bronchial, vaginal, and oral.

The presently disclosed pharmaceutical compositions also can include a cytotoxic cationic lipid of formula (I) or a delivery system comprising a cationic lipid of formula (I) in combination with a pharmaceutically acceptable carrier. As used herein the term "pharmaceutically acceptable carrier" includes solvents, dispersion media, coatings, antibacterial and antifungal agents, isotonic and absorption delaying agents, and the like, compatible with pharmaceutical or cosmetic administration. Supplementary active compounds also can be incorporated into the compositions.

As one of ordinary skill in the art would appreciate, a presently disclosed pharmaceutical composition is formulated to be compatible with its intended route of administration. Solutions or suspensions used for parenteral (e.g., intravenous), intramuscular, intradermal, or subcutaneous application can include the following components: a sterile diluent such as water for injection, saline solution, fixed oils, polyethylene glycols, glycerine, propylene glycol or other synthetic solvents; antibacterial agents, such as benzyl alcohol or methyl parabens; antioxidants, such as ascorbic acid or sodium bisulfite; chelating agents, such as ethylenediaminetetraacetic acid; buffers, such as acetates, citrates or phosphates; and agents for the adjustment of tonicity, such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF, Parsippany, N.J.) or phosphate buffered saline (PBS). The composition should be sterile and should be fluid to the extent that easy syringability exists. In some embodiments, the pharmaceutical compositions are stable under the conditions of manufacture and storage and should be preserved against the contaminating action of microorganisms, such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, isotonic agents, for example, sugars, polyalcohols, such as manitol or sorbitol, or sodium chloride are included in the formulation. Prolonged absorption of the injectable formulation can be brought about by including in the formulation an agent that delays absorption, for example, aluminum monostearate and gelatin.

Sterile injectable solutions can be prepared by incorporating the active compound (e.g., cytotoxic cationic lipid of formula (I) or a delivery system comprising a cationic lipid of formula (I)) in the required amount in an appropriate solvent with one or a combination of ingredients enumerated above, as required, followed by filtered sterilization. In certain embodiments, solutions for injection are free of endotoxin. Generally, dispersions are prepared by incorporating the active compound into a sterile vehicle which contains a basic dispersion medium and the required other ingredients from those enumerated above. In those embodiments in which sterile powders are used for the preparation of sterile injectable solutions, the solutions can be prepared by vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions also can be prepared using a fluid carrier for use as a mouthwash. Pharmaceutically or cosmetically compatible binding agents, and/or adjuvant materials can be included as part of the composition. The tablets, pills, capsules, troches, and the like can contain any of the following ingredients, or compounds of a similar nature: a binder, such as microcrystalline cellulose, gum tragacanth or gelatin; an excipient, such as starch or lactose, a disintegrating agent, such as alginic acid, Primogel, or corn starch; a lubricant, such as magnesium stearate or Sterotes; a glidant, such as colloidal silicon dioxide; a sweetening agent, such as sucrose or saccharin; or a flavoring agent, such as peppermint, methyl salicylate, or orange flavoring. Compositions for oral delivery can advantageously incorporate agents to improve stability within the gastrointestinal tract and/or to enhance absorption.

For administration by inhalation, the presently disclosed compositions can be delivered in the form of an aerosol spray from a pressured container or dispenser which contains a suitable propellant, e.g., a gas such as carbon dioxide, or a nebulizer. Liquid aerosols, dry powders, and the like, also can be used.

Systemic administration of the presently disclosed compositions also can be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds also can be prepared in the form of suppositories (e.g., with conventional suppository bases such as cocoa butter and other glycerides) or retention enemas for rectal delivery.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical or cosmetic carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of individuals. Guidance regarding dosing is provided elsewhere herein.

1. Articles of Manufacture

The present invention also includes an article of manufacture providing a cytotoxic cationic lipid of formula (I) or a delivery system comprising a cationic lipid of formula (I).

The article of manufacture can include a vial or other container that contains a composition suitable for the present method together with any carrier, either dried or in liquid form. The article of manufacture further includes instructions in the form of a label on the container and/or in the form of an insert included in a box in which the container is packaged, for carrying out the method of the invention. The instructions can also be printed on the box in which the vial is packaged. The instructions contain information such as sufficient dosage and administration information so as to allow the subject or a worker in the field to administer the pharmaceutical composition. It is anticipated that a worker in the field encompasses any doctor, nurse, technician, spouse, or other caregiver that might administer the composition. The pharmaceutical composition can also be self-administered by the subject.

II. Methods

The present invention provides methods for delivering a drug to a cell, for killing a cell, and for treating a diseased subject with a cytotoxic cationic lipid of formula (I) or delivery systems comprising a cationic lipid of formula (I). Further provided herein are methods for making delivery systems comprising cationic lipids of formula (I).

A. Methods of Delivery

Delivery systems comprising lipid vehicles comprising a cationic lipid of formula (I) can be used to deliver a bioactive compound to a cell. Such methods comprise contacting a cell with a delivery system comprising a lipid vehicle encapsulating the bioactive compound, wherein the lipid vehicle comprises a cationic lipid of formula (I). As described elsewhere herein, the term "deliver" when referring to a composition of the invention (e.g., a bioactive compound, a cytotoxic lipid) refers to the process resulting in the placement of the composition within the intracellular space of the cell or the extracellular space surrounding the cell. The term "cell" encompasses cells that are in culture and cells within a subject. In those embodiments in which the bioactive compound is a polynucleotide, the delivery of a polynucleotide into an intracellular space is referred to as "transfection."

The delivery of a polynucleotide to a cell can comprise an in vitro approach, an ex vivo approach, in which the transfection of the polynucleotide into a cell occurs outside of a subject (the transfected cells can then be transplanted into the subject), and an in vivo approach, wherein the transfection occurs within the subject itself.

In some embodiments, the polynucleotide is delivered by a polynucleotide delivery system, wherein the lipid vehicle of the delivery system comprises a cationic lipid of formula (I) and a co-lipid. In certain embodiments, the co-lipid is cholesterol.

B. Methods for Making a Delivery System

The present invention provides methods for making a delivery system, wherein the lipid vehicle of the delivery system comprises a cationic lipid of formula (I). Methods for making a delivery system comprising a lipid vehicle and a bioactive compound, wherein the lipid vehicle encapsulates the bioactive compound comprise mixing a lipid vehicle comprising a cationic lipid of formula (I) with a bioactive compound, thereby forming the delivery system. In some embodiments, the mixing step produces a lipid vehicle comprising a core supported bilayer.

In some embodiments, the lipid vehicle comprises a cytotoxic cationic lipid of formula (I). Thus, provided herein are methods for making a cytotoxic delivery system comprising a cytotoxic cationic lipid of formula (I). In some of these embodiments, the bioactive compound of the cytotoxic delivery system comprises a cytotoxic bioactive compound. In certain embodiments wherein a cytotoxic delivery system is made, the cytotoxic delivery system comprises a lipid vehicle comprising a cytotoxic cationic lipid of formula (I) encapsulating a cytotoxic bioactive compound.

Also provided are methods for making a polynucleotide delivery system comprising a lipid vehicle encapsulating a polycation and a polynucleotide, the method comprising the steps of:

a) mixing a polynucleotide and a polycation, thereby forming a polynucleotide/polycation solution; and b) mixing a lipid vehicle comprising a cationic lipid of formula (I) with the polynucleotide/polycation solution, thereby forming the delivery system.

Alternatively, in some embodiments, the methods for making a polynucleotide delivery system comprising a lipid vehicle encapsulating a polycation and a polynucleotide, comprise the steps of:

a) mixing a lipid vehicle comprising a cationic lipid of formula (I) and a polycation, thereby forming a lipid vehicle/polycation solution; and b) mixing the lipid vehicle/polycation solution with a polynucleotide, thereby forming the delivery system.

In some of these embodiments in which a polynucleotide delivery system is made, the delivery system further comprises a polyanionic carrier macromolecule. In these embodiments, the polyanionic carrier macromolecule can be mixed with the polynucleotide prior to the addition of the polycation. In other embodiments, the polynucleotide, polyanionic carrier macromolecule, and polycation can be mixed together simultaneously.

In certain embodiments wherein a polynucleotide delivery system is made, step b) produces a lipid vehicle comprising a core supported bilayer.

In some embodiments, the lipid vehicle comprises a liposome. In some of these embodiments, the liposome comprises a cationic liposome. In those embodiments in which the lipid vehicle comprises a liposome, the polynucleotide can be slowly added to the solution of liposomes or liposomes plus polycation and mixed with a stirring bar, where the mixing is allowed to proceed second after addition of polynucleotide. Alternatively, the liposome or liposome/polycation solution can be added into a single chamber from a first inlet at the same time the polynucleotide is added to the chamber through a second inlet. The components are then simultaneously mixed by mechanical means in a common chamber. The complexes can also be produced by first mixing the polynucleotide with the polycation and then adding the prepared liposomes.

Methods for preparing liposomes are known in the art. For example, a review of methodologies of liposome preparation may be found in *Liposome Technology* (CFC Press NY 1984); *Liposomes* by Ostro (Marcel Dekker, 1987); Lichtenberg and Barenholz (1988) *Methods Biochem Anal.* 33:337-462 and U.S. Pat. No. 5,283,185. For example, a mixture of the cationic lipids of formula (I) and optionally additional cationic lipids and/or co-lipids, from which the solvents have been removed, can be emulsified by the use of a homogenizer, lyophilized, and melted to obtain multilamellar liposomes. Alternatively, unilamellar liposomes can be produced by the reverse phase evaporation method (Szoka and Papahadjopoulos (1978) *Proc. Natl. Acad. Sci. USA* 75:4194-4198). In some embodiments, the liposomes are produced using thin film hydration, as described elsewhere herein (see Experimental section; Bangham et al. (1965) *J. Mol. Biol.* 13:238-252). In certain embodiments, the liposome formulation can be briefly sonicated and incubated at 50° C. for a short period of time (e.g., about 10 minutes) prior to sizing (see Templeton et al. (1997) *Nature Biotechnology* 15:647-652).

In some embodiments, the method for making a delivery system further comprises a sizing step after the liposomes have been prepared, wherein the sizing step comprises selecting a population of the liposomes based on the size (e.g., diameter) of the liposomes. The liposomes can be sized using techniques such as ultrasonication, high-speed homogenization, and pressure filtration (Hope et al. (1985) *Biochimica et Biophysica Acta* 812:55; U.S. Pat. Nos. 4,529,561 and 4,737,323). Sonicating a liposome suspension either by bath or probe sonication produces a progressive size reduction down to small unilamellar vesicles less than about 0.05 microns in size. Multilamellar vesicles can be recirculated through a standard emulsion homogenizer to the desired liposome size, typically between about 0.1 microns and about 0.5 microns. The size of the liposomal vesicles can be determined by quasi-elastic light scattering (QELS) (Bloomfield (1981) *Ann. Rev. Biophys. Bioeng.* 10:421-450). The average liposome diameter can be reduced by sonication of formed liposomes. Intermittent sonication cycles can be alternated with QELS assessment to guide efficient liposome synthesis. Alternatively, liposomes can be extruded through a smallpore polycarbonate membrane or an asymmetric ceramic membrane to yield a well-defined size distribution. Typically, a suspension is cycled through the membrane one or more times until the desired liposome size distribution is achieved. The liposomes can be extruded through successively smaller-pore membranes, to achieve a gradual reduction in liposome size.

In certain embodiments, the methods for making the delivery system can further comprise a purification step after the final step, wherein the delivery system complexes are purified from excess free bioactive agent, free lipid vehicle, and in some embodiments, free polycation. Purification can be accomplished through any method known in the art, including, but not limited to, centrifugation through a sucrose density gradient or other media which is suitable to form a density gradient. It is understood, however, that other methods of purification such as chromatography, filtration, phase partition, precipitation or absorption can also be utilized. In one method, purification via centrifugation through a sucrose density gradient is utilized. The sucrose gradient can range from about 0% sucrose to about 60% sucrose or from about 5% sucrose to about 30% sucrose. The buffer in which the sucrose gradient is made can be any aqueous buffer suitable for storage of the fraction containing the complexes and in some embodiments, a buffer suitable for administration of the complex to cells and tissues.

In some embodiments, a targeted delivery system or a PEGylated delivery system is made, wherein the methods further comprise a post-insertion step following the preparation of the lipid vehicle or following the final step in the methods, wherein at least one of a lipid-targeting ligand conjugate and a PEGylated lipid is post-inserted into the lipid vehicle (e.g., a liposome). Lipid vehicles comprising a lipid-targeting ligand conjugate or a PEGylated lipid can be prepared following techniques known in the art, including but not limited to those presented herein (see Experimental section; Ishida et al. (1999) *FEBS Lett.* 460:129-133; Perouzel et al. (2003) *Bioconjug. Chem.* 14:884-898). The post-insertion step can comprise mixing the lipid vehicle with the lipid-targeting ligand conjugate or a PEGylated lipid and incubating the particles at about 50° C. to about 60° C. for a brief period of time (e.g., about 5 minutes, about 10 minutes).

In some embodiments, the polynucleotide delivery systems are incubated with a lipid-PEG conjugate at a concentration of about 5 to about 20 mol %, including but not limited to about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, and about 20 mol %, to form a stealth polynucleotide delivery system. In some of these embodiments, the concentration of the lipid-PEG conjugate is about 10 mol %. The polyethylene glycol moiety of the lipid-PEG conjugate can have a molecular weight ranging from about 100 to about 20,000 g/mol, including but not limited to about 100 g/mol, about 200 g/mol, about 300 g/mol, about 400 g/mol, about 500 g/mol, about 600 g/mol, about 700 g/mol, about 800 g/mol, about 900 g/mol, about 1000 g/mol, about 5000 g/mol, about 10,000 g/mol, about 15,000 g/mol, and about 20,000 g/mol. In certain embodiments, the lipid-PEG conjugate comprises a PEG molecule having a molecular weight of about 2000 g/mol. In some embodiments, the lipid-PEG conjugate comprises DSPE-PEG$_{2000}$.

In certain embodiments wherein the delivery system complex has a net positive charge and/or the lipid vehicle of the delivery system has a positively charged surface at physiological pH, the amounts and ratios of the cytotoxic cationic lipid of formula (I), the polycation, and the polynucleotide that are mixed are such that the polynucleotide to lipid ratio allows for the delivery system complex to have a net positive charge at physiological pH (see, for example, U.S. Pat. No. 7,335,509, which is herein incorporated by reference).

In some embodiments wherein a polynucleotide delivery system comprising a lipid vehicle encapsulating a polycation and a polynucleotide are made, the lipid vehicle comprises a cytotoxic cationic lipid of formula (I). In some embodiments, the bioactive compound of the cytotoxic delivery system comprises a cytotoxic polynucleotide. In yet other embodiments, a cytotoxic polynucleotide delivery system is made, wherein the cytotoxic delivery system comprises a lipid vehicle comprising a cytotoxic cationic lipid of formula (I) encapsulating a polycation and a cytotoxic polynucleotide.

C. Methods for Killing Cells

The invention encompasses methods for killing a cell in which the cell is contacted with a cytotoxic cationic lipid of formula (I) or a cytotoxic delivery system. The cytotoxic delivery systems comprise a cationic lipid of formula (I) and the cytotoxic activity may be imparted by a cytotoxic bioactive compound, a cytotoxic cationic lipid of formula (I), or both.

As used herein, the term "kill" in relation to a cell refers to a process that results in a cell that is no longer able to reproduce, is no longer metabolically active, or is in any stage of apoptosis or necrosis (e.g., early stage, late stage). These methods can be used in vitro to kill cells that are in culture or in vivo to contact and kill cells within a subject. Methods for measuring cell death are well known in the art and are presented elsewhere herein.

When a cell is combined with other types of cells in culture or within an in vivo setting, wherein the cell is part of a subject, a particular cell type can be targeted and selectively killed through the use of a lipid-targeting ligand conjugate, wherein the lipid is a cytotoxic cationic lipid of formula (I). Thus, the invention provides methods for selectively killing a targeted cell, wherein the method comprises contacting the targeted cell with a lipid-targeting ligand conjugate, wherein the lipid is a cytotoxic cationic lipid of formula (I). Additionally, the invention presents methods for selectively killing a targeted cell comprising contacting the targeted cell with a targeted cytotoxic delivery system, wherein the exterior surface of the lipid vehicle of the targeted delivery system comprises a cationic lipid of formula (I). In some of these embodiments, the cationic lipid of formula (I) has cytotoxic activity. In other embodiments, the bioactive compound has cytotoxic activity. In still other embodiments, both the cationic lipid and the bioactive compound have cytotoxic activity.

In these embodiments, the targeted cell is selectively killed over a control cell. A control cell can be any type of suitable control cell known to one of skill in the art. For example, a control cell can be a cell that is not capable of interacting with the targeting ligand (e.g., does not express the cell surface protein that interacts with the targeting ligand) or the control cell might interact with the targeting ligand to a lesser extent than the targeted cell (e.g., the control cell expresses the cell surface protein that interacts with the targeting ligand to a lesser extent than the targeted cell). In some embodiments, about 2, about 3, about 4, about 5, about 10, about 20, about 30, about 40, about 50, about 60, about 70, about 80, about 90, about 100, about 500, or about 1000 times the number of targeted cells are killed over the number of killed control cells.

In some embodiments in which a targeted cell is selectively killed using the presently disclosed methods, the targeted cell is a cancer cell. Thus, the present invention provides methods for selectively killing a cancer cell by contacting a cancer cell with a lipid-targeting ligand conjugate or a targeted delivery system comprising a cytotoxic cationic lipid of formula (I). The targeted delivery system can optionally comprise a cytotoxic compound.

In some embodiments wherein a cancer cell is selectively killed and the bioactive compound of the targeted delivery system comprises a cytotoxic polynucleotide, the polynucleotide comprises a silencing element that when expressed or introduced into the cell reduces the expression of an oncogene. In certain embodiments, the oncogene comprises EGFR.

D. Methods of Treatment or Prevention

The cytotoxic cationic lipids of formula (I), delivery systems comprising a cationic lipid of formula (I), wherein the cationic lipid of formula (I) has cytotoxic activity, delivery systems comprising a cationic lipid of formula (I) and a bioactive compound that has therapeutic activity, and delivery systems comprising a cytotoxic cationic lipid of formula (I) and a bioactive compound with therapeutic activity can be used for the treatment of a subject afflicted with a disease or unwanted condition.

As used herein, "therapeutic activity" when referring to a bioactive compound is intended one that is able to elicit a desired pharmacologic and/or physiologic effect when administered to a subject in need thereof.

Thus methods for the treatment of a disease or unwanted condition in a subject comprise administering to the subject a pharmaceutical composition comprising a cytotoxic cationic lipid of formula (I), a pharmaceutical composition comprising a delivery system comprising a cationic lipid of formula (I), wherein the cationic lipid of formula (I) has cytotoxic activity, a pharmaceutical composition comprising a delivery system comprising a cationic lipid of formula (I) and a bioactive compound that has therapeutic activity against the disease or unwanted condition (e.g., is capable of treating the disease or unwanted condition). In some embodiments, the bioactive compound with therapeutic activity comprises a cytotoxic bioactive compound.

As used herein, the terms "treatment" or "prevention" refer to obtaining a desired pharmacologic and/or physiologic effect. The effect may be prophylactic in terms of completely or partially preventing a particular infection or disease or sign or symptom thereof and/or may be therapeutic in terms of a partial or complete cure of an infection or disease and/or adverse effect attributable to the infection or the disease. Accordingly, the method "prevents" (i.e., delays or inhibits) and/or "reduces" (i.e., decreases, slows, or ameliorates) the detrimental effects of a disease or disorder in the subject receiving the compositions of the invention. The subject may be any animal, including a mammal, such as a human, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

Any type of unwanted condition or disease can be treated therapeutically with the presently disclosed compositions. In some embodiments, the disease or unwanted condition that is to be treated is a cancer. As described elsewhere herein, the term "cancer" encompasses any type of unregulated cellular growth and includes all forms of cancer. In some embodiments, the cancer to be treated is a lung cancer. Methods to detect the inhibition of cancer growth or progression are known in the art and include, but are not limited to, measuring the size of the primary tumor to detect a reduction in its size, delayed appearance of secondary tumors, slowed development of secondary tumors, decreased occurrence of secondary tumors, and slowed or decreased severity of secondary effects of disease.

It will be understood by one of skill in the art that the administration of cytotoxic cationic lipids of formula (I) and delivery systems of the invention can be used alone or in conjunction with other therapeutic modalities, including, but not limited to, surgical therapy, radiotherapy, or treatment with any type of therapeutic agent, such as a drug. In those embodiments in which the subject is afflicted with cancer, the cytotoxic cationic lipids of formula (I) and delivery systems can be delivered in combination with any chemotherapeutic agent well known in the art, including, but not limited to, the chemotherapeutic agents described elsewhere herein, or any other cytotoxic drug, as described elsewhere herein or immunotherapy.

In one embodiment, the cytotoxic activity of a cytotoxic bioactive compound is enhanced in a subject in need thereof by administering to the subject the cytotoxic bioactive compound and a cytotoxic cationic lipid of formula (I). As used herein, the terms "enhance," "enhanced," or "enhancement" refers to an additive or synergistic increase. Thus, when the cytotoxic activity of a cytotoxic bioactive compound is enhanced by administering a cytotoxic cationic lipid of formula (I), or a cytotoxic delivery system, the cytotoxic activity is additively or synergistically increased relative to the administration of the cytotoxic bioactive compound or the cytotoxic cationic lipid alone.

In some embodiments, the cytotoxic bioactive compound and the cytotoxic cationic lipid can be administered simultaneously to the subject, wherein the cytotoxic bioactive compound and the cytotoxic cationic lipid are both present within a single composition that is administered to the subject. Alternatively, in other embodiments, the cytotoxic bioactive compound and the cytotoxic cationic lipid are administered in separate compositions sequentially. By "sequentially" is intended that the two compounds are administered one after the other to the subject, with two separate administrations of two distinct compositions, wherein one composition comprises the cytotoxic bioactive compound and the other composition comprises the cytotoxic cationic lipid. In some of the embodiments in which the cytotoxic bioactive compound and the cytotoxic cationic lipid are administered sequentially, the cytotoxic bioactive compound is administered first, followed by the cytotoxic cationic lipid. In other embodiments, the cytotoxic cationic lipid is administered to the subject in need thereof prior to the administration of the cytotoxic bioactive compound. In certain embodiments, the cytotoxic bioactive compound comprises cisplatin.

In other embodiments of the invention, the cytotoxic activity of a cytotoxic bioactive compound is enhanced in a subject by administering a delivery system comprising a lipid vehicle encapsulating said cytotoxic bioactive compound, wherein said lipid vehicle comprises a cationic lipid of formula (I) with cytotoxic activity. In some of these embodiments, the cytotoxic bioactive compound comprises a cytotoxic polynucleotide.

When administered to a subject in need thereof, the cytotoxic cationic lipid of formula (I) or delivery systems comprising the cationic lipid of formula (I) can further comprise a targeting ligand, as discussed elsewhere herein. In these embodiments, the targeting ligand will target the physically associated ligand or complex to a targeted cell or tissue within the subject. In some embodiments, the targeted delivery system is cytotoxic. In certain embodiments, the targeted cell or tissue will be diseased or characterized by the unwanted condition.

1. Dosing

Delivery of a therapeutically effective amount of a cytotoxic cationic lipid of formula (I) or a delivery system comprising a cationic lipid of formula (I) can be obtained via administration of a pharmaceutical composition comprising a therapeutically effective dose of this agent. By "therapeutically effective amount" or "dose" is meant the concentration of a cytotoxic cationic lipid of formula (I) or delivery system complex comprising a cationic lipid of formula (I) that is sufficient to elicit the desired therapeutic effect.

As used herein, "effective amount" is an amount sufficient to effect beneficial or desired clinical or biochemical results. An effective amount can be administered one or more times.

The effective amount of the cytotoxic cationic lipid of formula (I) or a delivery system complex comprising a cationic lipid of formula (I) will vary according to the weight, sex, age, and medical history of the subject. Other factors which influence the effective amount can include, but are not limited to, the severity of the subject's condition, the disorder being treated, the stability of the compound or complex, and, if desired, the adjuvant therapeutic agent being administered along with the lipid or lipid-comprising complex. Methods to determine efficacy and dosage are known to those skilled in the art. See, for example, Isselbacher et al. (1996) *Harrison's Principles of Internal Medicine* 13 ed., 1814-1882, herein incorporated by reference.

The pharmaceutical composition can be administered at various intervals and over different periods of time as required, e.g., multiple times per day, daily, every other day, once a week for between about 1 to 10 weeks, between 2 to 8 weeks, between about 3 to 7 weeks, about 4, 5, or 6 weeks, and the like. The skilled artisan will appreciate that certain factors can influence the dosage and timing required to effectively treat a subject, including but not limited to the severity of the disease, disorder, or unwanted condition, previous treatments, the general health and/or age of the subject, and other diseases or unwanted conditions present. Generally, treatment of a subject can include a single treatment or, in many cases, can include a series of treatments.

It is to be understood that appropriate doses of a compound depend upon its potency and can optionally be tailored to the particular recipient, for example, through administration of increasing doses until a preselected desired response is achieved. It is understood that the specific dose level for any particular animal subject can depend on a variety of factors including the activity of the specific compound employed, the age, body weight, general health, gender, and diet of the subject, the time of administration, the route of administration, the rate of excretion, any drug combination, and the degree of expression or activity to be modulated.

In another embodiment of the invention, a therapeutically effective dose of the cytotoxic cationic lipid of formula (I) or the delivery system comprising a cationic lipid of formula (I) is administered intermittently. By "intermittent administration" is intended administration of a therapeutically effective dose of the lipid or lipid-comprising complex, followed by a time period of discontinuance, which is then followed by another administration of a therapeutically effective dose, and so forth. Administration of the therapeutically effective dose can be achieved in a continuous manner, as for example with a sustained-release formulation, or it can be achieved according to a desired daily dosage regimen, as for example with one, two, three, or more administrations per day. By "time period of discontinuance" is intended a discontinuing of the continuous sustained-released or daily administration of the lipid or lipid-comprising complex. The time period of discontinuance may be longer or shorter than the period of continuous sustained-release or daily administration. During the time period of discontinuance, the level of the cationic lipid or lipid-comprising complexes of the invention in the relevant tissue is substantially below the maximum level obtained during the treatment. In some embodiments, the discontinuance period depends on the concentration of the effective dose. The discontinuance period can be at least 2 days, at least 4 days or at least 1 week. In other embodiments, the period of discontinuance is at least 1 month, 2 months, 3 months, 4 months or greater. When a sustained-release formulation is used, the discontinuance period must be extended to account for the greater residence time of the lipid or lipid-comprising complex at the therapeutic site. Alternatively, the frequency of administration of the effective dose of the sustained-release formulation can be decreased accordingly. An intermittent schedule of administration of the lipid or lipid-comprising complexes can continue until the desired therapeutic effect, and ultimately treatment of the disease or unwanted condition is achieved.

One of ordinary skill in the art upon review of the presently disclosed subject matter would appreciate that the presently disclosed compounds, including pharmaceutically acceptable salts and pharmaceutical compositions thereof, can be administered directly to a cell, a cell culture, a cell culture medium, a tissue, a tissue culture, a tissue culture medium, and the like. When referring to the novel cationic lipids of the invention or delivery systems of the invention, the term "administering," and derivations thereof, comprises any method that allows for the compound to contact a cell. The presently disclosed compounds, or pharmaceutically acceptable salts or pharmaceutical compositions thereof, can be administered to (or contacted with) a cell or a tissue in vitro or ex vivo. The presently disclosed compounds, or pharmaceutically acceptable salts or pharmaceutical compositions thereof, also can be administered to (or contacted with) a cell or a tissue in vivo by administration to an individual subject, e.g., a patient, for example, by systemic administration (e.g., intravenous, intraperitoneal, intramuscular, subdermal, or intracranial administration) or topical application, as described elsewhere herein.

III. Definition of Chemical Terms

While the following terms are believed to be well understood by one of ordinary skill in the art, the following definitions are set forth to facilitate explanation of the presently disclosed subject matter.

Throughout the specification and claims, a given chemical formula or name shall encompass all optical and stereoisomers, as well as racemic mixtures where such isomers and mixtures exist.

When the term "independently selected" is used, the substituents being referred to (e.g., R groups, such as groups $R_1$, $R_2$, and the like, or groups $Q_1$ and $Q_2$), can be identical or different. For example, both $R_1$ and $R_2$ can be substituted alkyls, or $R_1$ can be hydrogen and $R_2$ can be a substituted alkyl, and the like.

A named "R" or "Q" group will generally have the structure that is recognized in the art as corresponding to a group having that name, unless specified otherwise herein. For the purposes of illustration, certain representative "R" and "Q" groups as set forth above are defined below. These definitions are intended to supplement and illustrate, not preclude, the definitions that would be apparent to one of ordinary skill in the art upon review of the present disclosure.

As used herein, the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, such as a 3- to 7-member substituted or unsubstituted cycloalkyl ring system, including one or more heteroatoms, which can be the same or different, and are selected from the group consisting of N, O, and S, and optionally can include one or more double bonds. The cycloheteroalkyl ring can be optionally fused to or otherwise attached to other cycloheteroalkyl rings and/or non-aromatic hydrocarbon rings. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The term "alkenyl" as used herein refers to a straight or branched hydrocarbon of a designed number of carbon atoms containing at least one carbon-carbon double bond. Examples of "alkenyl" include vinyl, allyl, 2-methyl-3-heptene, and the like.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a straight or branched hydrocarbon of a designed number of carbon atoms containing at least one carbon-carbon triple bond. Examples of "alkynyl" include propargyl, propyne, and 3-hexyne.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Alkoxyl" refers to an alkyl-O— group wherein alkyl is as previously described. The term "alkoxyl" as used herein can refer to $C_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

The term "alkyl-thio-alkyl" as used herein refers to an alkyl-5-alkyl thioether, for example, a methylthiomethyl or a methylthioethyl group.

"Aralkyl" refers to an aryl-alkyl-group wherein aryl and alkyl are as previously described, and included substituted aryl and substituted alkyl. Exemplary aralkyl groups include benzyl, phenylethyl, and naphthyl methyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbbnyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

"Acyloxyl" refers to an acyl-O— group wherein acyl is as previously described.

The term "amino" refers to the —$NH_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

The term "alkylamino" refers to an —NHR group wherein R is an alkyl group and/or a substituted alkyl group as previously described. Exemplary alkylamino groups include methylamino, ethylamino, and the like.

"Dialkylamino" refers to an —NRR' group wherein each of R and R' is independently an alkyl group and/or a substituted alkyl group as previously described. Exemplary dialkylamino groups include ethylmethylamino, dimethylamino, and diethylamino.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.
The term "carboxyl" refers to the —COOH group.
The terms "halo", "halide", or "halogen" as used herein refer to fluoro, chloro, bromo, and iodo groups.
The term "hydroxyl" refers to the —OH group.
The term "hydroxyalkyl" refers to an alkyl group substituted with an —OH group.
The term "mercapto" refers to the —SH group.
The term "oxo" refers to a compound described previously herein wherein a carbon atom is replaced by an oxygen atom.
The term "nitro" refers to the —$NO_2$ group.
The term "thio" refers to a compound described previously herein wherein a carbon or oxygen atom is replaced by a sulfur atom.
The term "sulfate" refers to the —$SO_4$ group.
The term "guanidino" refers to a radical having the general chemical structure of:

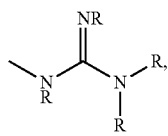

wherein each R can independently be, for example, H or alkyl.

The term "guanidinium" refers to the catinonic group having the general chemical structure of:

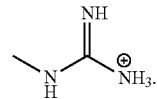

One of ordinary skill in the art would recognize that the guanidinium cation can exist in the following resonance canonical forms:

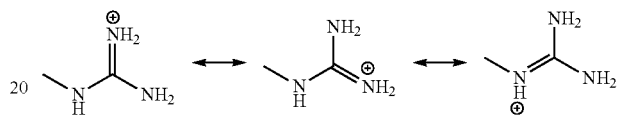

The following examples are offered by way of illustration and not by way of limitation.

EXPERIMENTAL

Materials and Methods for Examples 1-8

Fast atom bombardment mass spectrometry (FABMS) data were acquired by the liquid secondary ion mass spectrometry (LSIMS) technique using meta-nitrobenzyl alcohol as the matrix. LSIMS analysis was performed in the scan range 100-1000 amu at the rate of 3 scans/s. $^1$H NMR spectra were recorded on a Gemini 300 MHz spectrometer. Tetradecylamine, bromotetradecane N,N'-dicyclohexyl cardodiimide, N-epsilon-benzyloxycarbonyl-L-lysine, N-alpha-benzyloxycarbonyl-L-lysine, bromoethylamine hydrobromide, N-hydroxysuccinimide, Amberlite Cl ion exchange resin, trifluoroacetic acid, glacial acetic acid, 10% Pd—C, ammonium formate, celite, methyl iodide, thiourea, mercury chloride, Boc-anhydride, sodium hydride, and bromoethylaminehydrobromide were procured from Sigma Aldrich. Solvents like dichloromethane, chloroform, methanol, dimethylformamide, tetrahydrofuran, ethylacetate, and petroleum ether were purchased from Acros Organics. DOTAP and cholesterol were purchased from Avanti Polar Lipids, Inc. (Alabaster, Ala.). Protamine sulfate (fraction X from salmon) and calf thymus DNA (for hybridization, phenol-chloroform extracted and ethanol precipitated) were from Sigma-Aldrich (St. Louis, Mo.).

The progress of the reactions was monitored by thin layer chromatography on 0.25 mm silica gel plates purchased from Sigma Aldrich. Column chromatography was performed with silica gel (Sigma Aldrich, Grade 62, 60-200 mesh, 150 Å).

The EGFR and control siRNA sequences are adopted from previous studies (Banerjee et al. (2004) *Int. J. Cancer* 112: 693-700). Synthetic siRNAs were purchased from Dharmacon (Lafayette, Colo.). The sense strand of the EGFR siRNA has the sequence 5'-AACACAGUGGAGCGAAUUCCU-3' (set forth in SEQ ID NO: 1) and the sense strand of the high-purity control siRNA is 5'-AAUUCUCCGAACGUGU-CACGU-3' (SEQ ID NO: 2). For quantitative studies, FAM was conjugated to the 5' end of the sense sequence. 5' FAM-labeled siRNA was also obtained from Integrated DNA Technologies.

Synthesis of Lipids 1-3

Lipids 1-3 (FIG. 1) were synthesized following the procedures depicted schematically in FIG. 2. The synthetic procedure for a representative lipid, lipid 2, is detailed below. For the other two lipids, only TLC, $^1$H NMR and mass spectral data are provided below. Due to extensive line broadening in $^1$H NMR spectra of the final deprotected lipids (particularly in the region δ/ppm=3-5), all the final lipids were characterized by LSIMS.

Synthesis of N,N-Dimyristoyl-N-methyl-N-2[N'—(N$^2$-guanidino-L Lysinyl)]aminoethyl ammonium Chloride (Lipid 2)

Step (a) Solid HOSu (0.15 g, 1.3 mmol) and DCC (0.29 g, 1.4 mmol) were added sequentially to an ice cold and stirred solution of N$^ε$, -tert-butyloxycarbonyl-N$^α$-benzyloxylcarbonyl-L-Lysine (0.48 g, 1.3 mmol, prepared from N$^α$-benzyloxycarbonyl-L-Lysine and di-tert-butyldicarbonate as described previously (Bodanszky and Bodanszky (1984) Springer-Verlag, Berlin, Heidelberg, p. 20) in dry DCM/dry DMF (9:1, v/v). After half an hour, N-aminoethyl-N,N-di-n-tetradecylamine (0.57 g, 1.3 mmol, prepared as described previously (Kumar et al. (2003) *Gene Ther.* 10:1206-1215) and DMAP (catalytic) dissolved in dry DCM were added to the reaction mixture. The resulting solution was stirred at room temperature for 24 h, solid DCU was filtered and the solvent from the filtrate was evaporated. The residue was dissolved in ethyl acetate (100 mL) and washed sequentially with ice-cold 1N HCl (3×100 mL), saturated sodium bicarbonate (3×100 mL) and water (3×100 mL). The organic layer was dried over anhydrous sodium sulfate, filtered, and the solvent from the filtrate removed by rotary evaporation. The residue was loaded upon a chromatographic purification column with 60-120 mesh silica gel using 2-2.5% methanol-dichloromethane (v/v) as the eluent, which afforded 0.612 g (58%) of the pure intermediate, N-2-[N'—(N$^ε$-BOC, N$^α$-Benzyloxycarbonyl-L-Lysinyl)]aminoethyl-N,N-di-n-tetradecylamine. (R$_f$=0.6, 10% methanol-dichloromethane, v/v). $^1$H NMR (300 MHz, CDCl$_3$): δ/ppm=0.9 [t, 6H, CH$_3$—(CH$_2$)$_{11}$—]; 1.2-1.4 [m, 44H, —(CH$_2$)$_{11}$—]; 1.3-1.6 [m, 4H, LysC$^γ$H$_2$+LysC$^δ$H$_2$]; 1.4 [s, 9H, —CO—O—C(CH$_3$)$_3$]; 1.5 [m, 4H, —N(—CH$_2$—CH$_2$—)$_2$]; 1.8 [m, 2H, LysC$^β$H$_2$]; 2.4-2.6 [bm, 6H, —N(—CH$_2$—CH$_2$—)$_2$+—N—CH$_2$—CH$_2$—NH—CO—O—]; 3.1 [m, 2H, Lys$^ω$CH$_2$]; 3.3 [m, 2H, —N—CH$_2$—CH$_2$—NH—CO—]; 4.0-4.2 [2 m, 2H, LysC$^α$H+—CH$_2$—CH$_2$—NH—CO—]; 4.6 [m, 1H, BOC—NH]; 5.1 (s, 2H, Z—CH$_2$); 5.5 (m, 1H, Z—NH); 7.3 (m, 5H, Ar—H).

Step (b). The intermediate (0.62 g, 0.76 mmol) obtained in step (a) was dissolved in dry methanol (10 mL) containing a few drops of glacial acetic acid. Ammonium formate (0.38 g, 6.0 mmol) & 10% Pd/C (0.25 g) were added and the reaction mixture was allowed to stir under nitrogen atmosphere for 6 h. The catalyst was removed by filtration through celite and then the filtrate was dried by evaporation. The residue was dissolved in ethyl acetate (50 mL) and washed sequentially with 30% aqueous potassium carbonate (3×50 mL), saturated sodium chloride (3×50 mL) and water (3×50 mL). The organic layer was dried over anhydrous sodium sulfate, filtered, and rotatory evaporation of the solvent from the filtrate afforded 0.51 g (69%) of the intermediate N$^2$-[N'—(N$^ε$-BOC-L-Lysinyl)]aminoethyl-N,N-di-n-tetradecylamine (Scheme I) (R$_f$=0.2, 10% methanol in dichloromethane, v/v). This intermediate, without further purification was directly used for step (c).

Step (c) Mercury chloride (0.16 g, 0.57 mmol) was added to a mixture of N-2-[N'—(N$^ε$-BOC-L-Lysinyl)]aminoethyl-N,N-di-n-tetradecylamine (0.35 g. 0.5 mmol), bis-BOC thiourea (0.15 g, 0.5 mmol), and triethylamine (0.11 g, 1.1 mmol) dissolved in dry DMF (5 mL) and dry DCM (2 mL) at 0° C. with continuous stirring. The resulting mixture was stirred at 0° C. under nitrogen for 40 min, diluted with ethyl acetate (20 mL) and filtered through a pad of celite. The filtrate solution was washed with water (2×20 mL), and then brine solution (2×20 mL). The organic layer was dried over anhydrous sodium sulfate, filtered, and the solvent from the filtrate removed by rotary evaporation. The residue was loaded upon a chromatographic purification column with 60-120 mesh silica gel using 2-2.5% methanol-dichloromethane (v/v) as the eluent, which afforded 0.25 g (53%) of the pure intermediate N$^2$-[N'—(N$^ε$-BOC, N$^α$-(DiBenzyloxycarbonyl guanidino-L-Lysinyl)]aminoethyl-N,N-di-n-tetradecylamine. (R$_f$=0.8, 10% methanol-dichloromethane, (v/v).

$^1$H NMR (300 MHz, CDCl$_3$): δ/ppm=0.9 [t, 6H, CH$_3$—(CH$_2$)$_{11}$—]; 1.2-1.4 [m, 44H, —(CH$_2$)$_{11}$—]; 1.3-1.6 [m, 4H, LysC$^γ$H$_2$+LysC$^δ$H$_2$]; 1.4-1.6 [3s, 27H, CO—O—C(CH$_3$)$_3$]; 1.5 [m, 4H, —N(—CH$_2$—CH$_2$—)$_2$]; 1.75 [m, 2H, LysC$^β$H$_2$]; 2.4 [t, 4H, —N(—CH$_2$—CH$_2$—)$_2$]; 2.5 [t, 2H, —N—CH$_2$—CH$_2$—NH—CO]; 3.1 (m, 2H, Lys$^ω$CH$_2$); 3.3 [m, 2H, —N—CH$_2$—CH$_2$—NH—CO]; 4.6 [m, 1H, LysC$^α$H]; 6.7 [m, 1H, BOC—NH—CH$_2$]; 7.9 [m, 1H, —CH$_2$—NH—CO—]; 8.8 [d, 1H, —CH$_2$—NH—]; 11.4[s, 1H, C—NHBOC].

Step (d): The intermediate obtained in step (c) (0.25 g) was dissolved in 3 mL dichloromethane/methanol (2:1, v/v) and 3 mL methyl iodide was added. The solution was stirred at room temperature overnight and the solvent was removed on a rotary evaporator. The residue was loaded upon a chromatographic purification column with 60-120 mesh size silica gel, and 3-4% methanol in chloroform (v/v) as the eluent afforded 0.16 g (56% yield) of quarternised intermediate (R$_f$=0.6, 10% methanol in chloroform, v/v).

$^1$H NMR (300 MHz, CDCl$_3$): δ/ppm=0.9 [t, 6H, CH$_3$—(CH$_2$)$_{11}$—]; 1.2-1.4 [m, 44H, —(CH$_2$)$_{11}$—]; 1.3-1.6 [m, 4H, LysC$^γ$H$_2$+LysC$^δ$H$_2$]; 1.4-1.6 [3s, 27H, CO—O—C(CH$_3$)$_3$]; 1.5 [m, 4H, —N$^+$(—CH$_2$—CH$_2$—)$_2$]; 1.7 [m, 2H, LysC$^β$H$_2$]; 3.1 [m, 2H, Lys$^ω$CH$_2$]; 3.2[s, 3H, (—N$^+$—CH$_3$)]; 3.3 [m, 4H, —N(—CH$_2$—CH$_2$—)$_2$]; 3.7 [m, 2H, —N$^+$—CH$_2$—CH$_2$—NH—CO]; 3.8 [m, 2H, —N$^+$—CH$_2$—CH$_2$—NH—CO]; 4.5 [m, 1H, LysC$^α$H]; 4.7 [m, 1H, BOC—NH]; 8.2 [t, 1H, —CH$_2$—NH—CO—]; 8.7[d, 1H, —CH—NH—C—]; 11.3[s, 1H, —NHBOC].

Step (e): The intermediate obtained in step (d) (0.16 g) was dissolved in dry DCM (2 mL) and TFA (2 mL) was added at 0° C. The resulting solution was stirred at room temperature overnight to ensure complete deprotection. Excess TFA was removed by flushing nitrogen to give the title compound as a trifluoroacetate salt. Column chromatographic purification using 60-120 mesh size silica gel with 12-15% (v/v) methanol-chloroform as eluent followed by chloride ion exchange chromatography (using amberlyst A-26 chloride ion exchange resin) afforded 0.08 g (69% yield) of the pure title compound 2 (R$_f$=0.3, 20% methanol in chloroform, v/v). LSIMS (lipid 2): m/z: 637.8 [MH$^+$] (calcd for C$_{38}$H$_{81}$ON$_6$, 74%).

Lipids 1 & 3 were synthesized following the same steps as described above for lipid 2 (FIG. 2). The TLC characteristics, $^1$H NMR spectral data for the immediate precursor of the remaining final lipids, and the LSIMS data for the remaining final lipids are provided below.

Lipid 1:
$^1$H NMR (300 MHz, CDCl$_3$) of immediate precursor of N,N-di-myristoyl-N-methyl-N-2[N'—(N$^6$-guanidino-L-Lysinyl)]aminoethyl ammonium Chloride (lipid 1, DMGLA), (R$_f$=0.6, 10% methanol in dichloromethane, v/v:)

$^1$H NMR (200 MHz, CDCl$_3$): δ/ppm=0.9 [t, 6H, CH$_3$—(CH$_2$)$_{13}$—]; 1.2-1.4 [m, 44H, —(CH$_2$)$_{13}$—]; 1.3-1.6 [m, 4H, LysC$^γ$H$_2$+LysC$^δ$H$_2$]; 1.4-1.6 [3s, 27H, CO—O—C(CH$_3$)$_3$]; 1.5 [m, 4H, —N$^+$(—CH$_2$—CH$_2$—)$_2$]; 1.7 [m, 2H, LysC$^β$H$_2$]; 3.2[s, 3H, —N$^+$—CH$_3$]; 3.3 [t, 6H, —N(—CH$_2$—CH$_2$—)$_2$; Lys$^ω$CH$_2$]; 3.7 [m, 4H, —N$^+$—CH$_2$—CH$_2$—NH—CO]; 4.1 [m, 1H, LysC$^α$H]; 5.2 [m, 1H, BOC—NH]; 8.1-8.3 [2t, 2H, —CH$_2$—NH—CO—; —CH$_2$—NH—C—]; 11.45[s, 1H, —NHBOC].

LSIMS (lipid 1): m/z: 637.9 [MH$^+$] (calcd for C$_{38}$H$_{81}$ON$_6$, 57%).

Lipid 3:
$^1$H NMR (300 MHz, CDCl$_3$) of immediate precursor of N,N-Dimyristoyl-N-methyl-N-2[N'—(N$^2$,N$^6$-di-guanidino-L-Lysinyl)]aminoethyl ammonium Chloride (lipid 3), (R$_f$=0.6, 10% methanol in dichloromethane, v/v)

$^1$H NMR (200 MHz, CDCl$_3$): δ/ppm=0.9 [t, 6H, CH$_3$—(CH$_2$)$_{15}$—]; 1.2-1.4 [m, 44H, —(CH$_2$)$_{15}$—]; 1.3-1.6 [m, 4H, LysC$^γ$H$_2$+LysC$^δ$H$_2$]; 1.4 [m, 36H, CO—O—C(CH$_3$)$_3$]; 1.5-1.7 [m, 6H, —N$^+$(—CH$_2$—CH$_2$—)$_2$+LysC$^β$H$_2$]; 3.25 [s, 3H, —N$^+$—CH$_3$]; 3.3 [t, 6H, —N(—CH$_2$—CH$_2$—)$_2$; Lys$^ω$CH$_2$]; 3.7 [m, 2H, —N$^+$—CH$_2$—CH$_2$—NH—CO]; 3.8 [m, 2H, —N$^+$—CH$_2$—CH$_2$—NH—CO]; 4.5 [m, 1H, LysC$^α$H]; 8.1-8.3 [2t, 2H, —CH$_2$—NH—CO—; —CH$_2$—NH—C—]; 8.7 [d, 1H, CH—NH—C—]; 11.3-11.5 [2s, 2H, —NHBOC].

LSIMS (lipid 3): m/z: 679.8 [MH$^+$] (calcd for C$_{39}$H$_{83}$ON$_8$, 36%).

$^1$NMR (300 MHz, CDCl$_3$) of immediate precursor of N,N-di-stearoyl-N-methyl-N-2[N'—(N$^6$-guanidino-L-Lysinyl)] aminoethyl ammonium Chloride (lipid 1, DSGLA), (R$_f$=0.6, 10% methanol in dichloromethane, v/v:)

$^1$H NMR (200 MHz, CDCl$_3$): δ/ppm=0.9 [t, 6H, CH$_3$—(CH$_2$)$_{13}$-]; 1.2-1.4 [m, 60H, —(CH$_2$)$_{13}$—]; 1.3-1.6 [m, 4H, LysC$^γ$H$_2$+LysC$^δ$H$_2$]; 1.4-1.6 [3s, 27H, CO—O—C(CH$_3$)$_3$]; 1.5 [m, 4H, —N$^+$(—CH$_2$—CH$_2$—)$_2$]; 1.7 [m, 2H, LysC$^β$H$_2$]; 3.2[s, 3H, —N$^+$—CH$_3$]; 3.3 [t, 6H, —N(—CH$_2$—CH$_2$—)$_2$; Lys$^ω$CH$_2$]; 3.7 [m, 4H, —N$^+$—CH$_2$—CH$_2$—NH—CO]; 4.1 [m, 1H, LysC$^α$H]; 5.2 [m, 1H, BOC—NH]; 8.1-8.3 [2t, 2H, —CH$_2$—NH—CO—; —CH$_2$—NH—C—]; 11.45[s, 1H, —NHBOC].

LSIMS (lipid 1): m/z: 749.8 [MH$^+$] (calcd for C$_{46}$H$_{97}$ON$_6$, 47%).

Synthesis of Mono-arginylated Cationic Lipid DSAA

Step (a): N-[2-tert-butyloxycarbonylamino ethyl]-N,N-di-n-octadecylamine: A mixture of 0.6 g (4.13 mmol) of N-Boc-Ethylenediamine(I) and 4.127 g (12.39 mmol) of octadecyl-bromide was refluxed in EtoAc in the presence of anhydrous potassium carbonate (2.2 g; 16.52 mmol) for 24 h. The reaction mixture was diluted with 100 mL ethyl acetate, washed with water (2×100 mL), dried over anhydrous sodium sulfate and filtered. Ethyl acetate was removed from the filtrate on a rotary evaporator. Silica gel column chromatographic purification of the resulting residue (10% ethyl acetate in hexane, v/v, as the eluent) afforded 1.78 g (light yellow solid, 65% yield) of the title compound (R$_f$=0.4 in 30% ethyl acetate in hexane, v/v, as the TLC developing solvent).

1H NMR (300 MHz, CDCl3): δ/ppm=0.9 [t, 6H, CH3-(CH2)16-]; 1.2-1.4 [m, 64H, —(CH2)16-CH3]; 1.5 [s, 9H, —COO—C(CH3)3]; 2.4 [t, 4H, —N(CH2-(CH2-)16]; 2.5 [t, 2H, —N(CH2-CH2-NHBoc]; 3.1 [m, 2H, N(CH2-CH2-NH-Boc)]; 4.9 [bm, 1H, NHBoc].

Step (b): N-2-aminoethyl-N,N-di-n-octadecylamine: The product obtained above (1.7 g; 2.85 mmol) was dissolved in 10 mL of anhydrous dichloromethane (DCM), and 4 mL of neat trifluoroacetic acid (TFA) was added. The reaction mixture was stirred overnight at room temperature. The TFA was removed by flushing with nitrogen and the remaining residue was kept under vacuum for 15 min. The resulting trifluoroacetate salt of the title compound was dissolved in 25 mL of DCM, and 25 mL of aqueous 1 N NaOH was added. The resulting biphasic mixture was stirred at room temperature for 2 h. The organic layer was washed with water (3×50 mL), dried over anhydrous sodium sulfate, filtered, and the solvent from the filtrate was evaporated under rotary evaporator. Column chromatographic purification of the residue (2-3% methanol in chloroform, v/v, as the eluent) afforded 1.068 g of the title compound (74% yield, R$_f$=0.4 using 10% methanolic chloroform, v/v, as the TLC developing solvent).

1H NMR (300 MHz, CDCl3): δ/ppm=0.9[t, 6H, CH3-(CH2)15-]; 1.2-1.4 [m, 60-(CH2)15-]; 1.5 [m, 4H, N(—CH2-CH2-)2]; 2.5 [m, 4H, N(CH2-CH2-)2]; 2.6 [t, 2H, —N(CH2-CH2-NH2)]; 2.9 [t, 2H, —N(CH2-CH2-NH2)]; 3.5-3.7 [bm, 2H, NH2].

Step (c): Tri-Boc-Arginine(N,N-di-n-octadecylamine) ethylamide: A mixture of N-2-aminoethyl-N,N-di-n-octadecylamine (1.05 g; 1.94 mmol), N-(3-Dimethylaminopropyl)-N'-ethylcarbodiimide hydrochloride (0.372 g; 1.94 mmol), N-hydroxysuccinimide (0.223 g; 1.9 mmol) and tri-Boc-Arginine (0.92 g, 1.944 mmol) dissolved in a mixture of 10 mL dry DCM and 5 mL dry DMF were stirred for 16 h. In total, 50 mL of DCM was added to the reaction mixture, and the mixture was washed with water (3×100 mL) and dried with anhydrous sodium sulfate. Silica gel column chromatographic purification (10% acetone in hexane form, v/v, as the eluent) of the residue afforded 1.17 g of pure coupled product (yield=62%, R$_f$=0.5 using 40% acetone in hexane, v/v, as the TLC developing solvent). 1H NMR (CDCl$_3$, 300 MHz): δ/ppm=0.9[t, 6H, CH3-(CH2)16-]; 1.2-1.3 [m, 64H, CH3-(CH2)16]; 1.4-1.6 [2s, 27H, —CO—O—(CH3)3]; 1.6-1.8 [m, 4H, CH2-CH2-Arg] 2.4-2.5 [m, 6H, —N—CH2-(CH2)16-CH3; —NCH2-CH2-NH—CO—]; 3.2-3.3 [2 dd, 2H, —CH2-CH2-NH—CO—]; 3.9 [m, 2H, Arg CH2-N]; 4.2 [m, 1H, —CH(NHBoc)-CO—]; 5.7 [m, 3H, —NH—CO—O—(CH$_3$)3].

Step (d): Tri-Boc-Arginine(N,N-di-n-octadecylamine,-methyl)ethylamide: Compound IV (1.1 g, 1.0772 mmol) obtained in step (c) was dissolved in 5 mL DCM, and 3 mL methyl iodide was added. The solution was stirred overnight. Solvent was removed on rotary evaporator and silica gel column chromatography (2% methanolic chloroform, v/v, as the eluent) of the residue afforded 0.964 g of the title compound (89% yield).

1H NMR (CDCl3, 300 MHz): δ/ppm=0.9 [t, 6H, CH3-(CH2)16]; 1.2-1.3 [m, 64H, CH3-(CH2)16-]; 1.4-1.6 [2s, 27H, CO—O—C(CH3)3]; 1.6-1.8 [m, 8H, —CH2-CH2-N+—, —CH2-CH2-Arg]; 3.9 [2H, Arg CH2-N]; 3.2 [S, 3H, CH3-N+—]; 3.4 [m, 4H, —N+—CH2-(CH2)16-CH3]; 3.6-3.7 [bm, 4H, —N+—CH2-CH2-NHCO—]; 4.19 [m, 1H, —CH(NHBoc)CO—]; 5.7 [s, 3H, —NH—CO—O—(CH3)3].

Step (e): L-Arginine (N,N-di-n-octadecylamine, N-methyl)ethylamide (DASS): Compound V (0.9 g, 0.868 mmol) obtained in step (d) was dissolved in 5 mL of 3 N HCl in dioxane and the solution was stirred for 12 h. The solvent was removed with nitrogen flush and the residue was kept under vacuum for an additional 1 h. Silica gel column chromatography (12% methanolic chloroform, v/v, as the eluent) followed by chloride ion-exchange chromatography (using Amberlyst-A 26 chloride ion-exchange resin) of the dried residue afforded 450 mg of pure title compound (71% yield).

1H NMR (CD3OD, 300 MHz): δ/ppm=0.9 [s, 6H, CH3-(CH2)15-]; 1.2-1.3 [m, 60H, CH3-(CH2)15-]; 1.6-1.7 [m, 4H, CH3-(CH2)15-CH2-CH2-N+—]; 3.4-3.7 [2 m, 6H, Arg]; 3.1 [S, 3H, CH3-N+—CH2-CH2-]; 3.2-3.4 [m, 8H, (CH3-(CH2)16-CH2)2-N+(CH3)-CH2-CH2-NHCO—]; 3.9 [t, 1H, —CH(NH3+)CO—].

ESI-MS: m/z: 736 (90%).

Preparation of Liposomes

The cationic lipid and the colipid (cholesterol or DOPE) in 1:1 mole ratio were dissolved in a mixture of chloroform and methanol (3:1, v/v) in a glass vial. The solvent was removed with a thin flow of moisture-free nitrogen gas, and the dried lipid film was then kept under high vacuum for 8 h. Sterile deionized water (5 mL) was added to the vacuum-dried lipid film, and the mixture was allowed to swell overnight. The vial was then vortexed for 2-3 min at room temperature and occasionally sonicated in a bath sonicator to produce multilamellar vesicles (MLVs). MLVs were then sonicated in an ice bath until clear using a Branson 450 sonifier at 100% duty cycle and 25 W output power. The resulting clear aqueous liposomes were used in forming LPD nanoparticles.

Transfection

Figure 4:
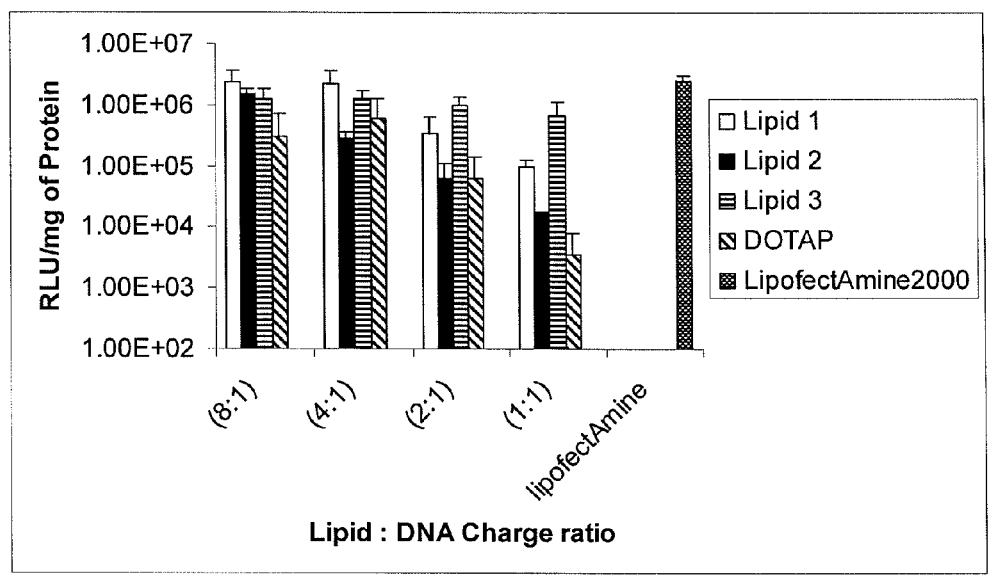
FIG. 4 presents the in vitro transfection efficiencies of lipids 1-3 in H460 cells in the presence of serum using cholesterol as a co-lipid (at a lipid/cholesterol mole ratio of 1:1). RLU/pgram of protein was plotted against the lipid to DNA (+/−) charge ratios. The transfection efficiencies of the lipids were compared to that of commercially available N-(2,3-dioleoyloxy) propyl)-N,N,N-trimethylammonium chloride (DOTAP) and Lipofectamine™ 2000. The transfection values shown are the average of triplicate experiments performed on the same day.

H460 human large-cell lung carcinoma cells were seeded at a density of 20,000 cells per well in a 96-well plate 18-24 h prior to the transfection. Plasmid DNA (0.3 μg) was complexed with varying amounts of lipids (0.9-7.2 nmol) in plain RPMI medium (total volume of 100 μL) for 20 min. The charge ratios were varied from 1:1 to 8:1 (+/−) over these ranges of the lipids. The complexes were then added to the cells. After 3 h of incubation, 100 μL of RPMI with 20% FBS was added to the cells. The reporter gene activity was estimated after 24 h. The cells were washed twice with phosphate-buffered saline (PBS, 100 μL each) and lysed in 100 μL of lysis buffer (0.1 M Tris-HCl, 2 mM EDTA, 0.5% Triton X100, pH 7.8). Care was taken to ensure complete lysis. The cell lysate was then centrifuged at 14,000 rpm for 5 min. A 10 μL aliquot of the supernatant was taken for analysis of luciferase activity. The protein concentration within the cellular lysates was quantified with the BSA standards from the Micro BSA™ Protein assay kit as supplied by Pierce Chemical Company (Rockford, Ill.). The luciferase activity for each assay is presented as relative light units per μg of soluble protein (RLU/μg protein). The transfection experiment was carried out in triplicate, and the transfection efficiency values shown in FIG. 4 are the average of triplicate experiments performed on the same day. Each transfection experiment was repeated three times. The transfection profiles obtained on different days were identical.

Preparation of Pegylated LPD Compositions

Lipid/polycation/DNA (LPD) nanoparticles were prepared as previously described with slight modifications (Cui et al. (2005) *Mol. Pharm.* 2:22-28). Briefly, small unilamellar liposomes consisting of DOTAP (or DSGLA) and cholesterol (1:1 molar ratio) were prepared by thin film hydration followed by membrane extrusion. The total lipid concentration of the liposome was fixed at 10 mM. LPD was composed of DOTAP (or DSGLA)/cholesterol liposome, protamine, and the mixture of oligonucleotide and calf thymus DNA (1:1 weight ratio). To prepare LPD, 6 μL of protamine (2 mg/mL), 47 μL of deionized water, and 8 μL of DOTAP (or DSGLA)/cholesterol liposome (total lipid concentration=10 mM) were mixed. LPD nanoparticles were kept at room temperature for another 10 min before further application. PEGylated LPD compositions were prepared by the postinsertion method (Ishida et al. (1999) *FEBS Lett.* 460:129-133; Perouzel et al. (2003) *Bioconjug. Chem.* 14:884-898). Briefly, 100 μL of preformed LPD was mixed with 0.63-16 μL of DSPE-PEG or DSPE-PEG-AA (20 mg/mL) and then incubated at 50-60° C. for 10 min. The resulting compositions were allowed to cool to room temperature before use. The particles were mixed with oligonucleotide and calf thymus DNA (2 mg/mL) in a 1.5 mL tube. The complex was allowed to stand at room temperature for 10 min before LPD and PEGylated LPD were measured using a Coulter N4 Plus particle sizer (Beckman Coulter, San Francisco, Calif.). Particle sizes were reported as the mean±standard deviation.

Cellular Growth Inhibition Study

H460 cells ($1 \times 10^4$ per well) were seeded into 12-well plates. Cells were treated with different lipids at various concentrations in serum-containing medium at 37° C. for 72 h. Cell viability was then detected by an MTT assay. Briefly, 100 μL of the MTT solution (15 mg in 50 mL of PBS) was added to each well, and the cells were incubated for 4 h at 37° C. The medium was removed, and the formazan crystals formed in the cells were dissolved in DMSO. Absorbance at 570 nm was measured in an Ultramark Microplate Imaging System. The data are expressed as the percent of viable cells compared to the untreated control cells.

Chemosensitization Study

H460 cells ($1 \times 10^4$ per well) were seeded into 12-well plates. Cells were incubated with different lipids at 10 μM and cisplatin (Sigma-Aldrich, St. Louis, Mo.) at different concentrations in serum-containing medium at 37° C. Cell viability was detected by the MTT assay 48 h later.

Cellular Uptake Study

H460 cells ($1 \times 10^5$ per well) were seeded in 12-well plates (Corning Inc., Corning, N.Y.) 12 h before experiments. Cells were treated with different compositions at a concentration of 100 nM for 5' FAM-labeled siRNA in serum-containing medium at 37° C. for 4 h. Cells were washed twice with PBS, followed by incubation with lysis buffer (0.3% Triton X-100 in PBS) at room temperature for 1 h. Fluorescence intensity of the cell lysate was determined by a Perkin-Elmer LS 50B luminescence spectrometer (Norwalk, Conn.) ($\lambda_{ex}$, 494 nm; $\lambda_{em}$, 519 nm).

Annexin V and Propidium Iodide (PI) Staining and Quantification

H460 cells ($5 \times 10^4$ per well) were seeded into 6-well plates. Cells were treated with different compositions at a concentration of 500 nM for siRNA in serum-containing medium at 37° C. for 72 h. Cells were washed once with PBS, trypsinized, and resuspended in PBS at a concentration of $1 \times 10^6$ cells/mL. Cells were then stained with Annexin V-FITC using a kit (BD Biosciences Pharmingen, San Jose, Calif.) and 1.25 μg/mL PI. Cells stained with Annexin V-FITC and PI were detected and quantified by flow cytometry (Becton-Dickinson, Heidelberg, Germany). Results were processed using the Cellquest software (Becton-Dickinson).

Assessment of Apoptosis by TUNEL Staining

TUNEL assay was conducted using a TACS™ TdT Kit (R&D Systems, Minneapolis, Minn.). H460 cells ($5 \times 10^4$ per well) were seeded into 24-well plates. Cells were treated with different compositions at a concentration of 500 nM for siRNA in serum-containing medium at 37° C. for 72 h. Cells were washed once with PBS, and then fixed in 4% buffered paraformaldehyde-PBS (pH 7.4) for 30 min at room temperature. Endogenous peroxidase was inactivated with 0.3% $H_2O_2$ methanol for 15 min at room temperature. The plates were then rinsed with PBS, and after processing with Permeabilization Buffer, labeling Buffer containing terminal deoxynucleotidyl transferase and fluorescein isothiocyanate-deoxyuridine 5-triphosphate was added to the plate. The plate was incubated in a humid atmosphere at 37° C. for 60 min. The reaction was terminated by stop solution and developed with DAB according to manufacturer's instructions. Samples were imaged using a Nikon Microphot SA microscope.

Western Blot Analysis

Cells were lysed in lysis buffer for 20 min on ice and the soluble extract was recovered by centrifugation. Extracts were separated on a 10% acrylamide gel and transferred to a PVDF membrane. Membranes were blocked for 1 h in 5% skim milk and then incubated for 1 h with monoclonal antibodies directed against pERK (Santa Cruz Biotechnology, Inc.) or polyclonal antibodies against EGFR (BD Transduction Labs). Membranes were also incubated with antibodies that recognize ERK 2 and actin (Santa Cruz Biotechnology, Inc.) for standardization. Membranes were washed in PBST (PBS, 0.1% Tween-20) and then incubated for 1 h with appropriate secondary antibodies. Membranes were again washed and then developed by an enhanced chemiluminescence system according to the manufacturer's instructions (PerkinElmer).

Immunofluorescence Microscopy

H460 cells were washed, fixed with methanol/acetone (1:1), and permeabilized with Triton X100 (1%). Cells were incubated with rabbit polyclonal anti-Apoptosis-Inducing-Factor (AIF) (Santa Cruz Biotechnology, Inc.) (1:100) for 1 h. After washing with PBS, the fluorescently-labeled secondary antibody was added and incubated for 1 h. Nuclei were counterstained with Vectashield® mounting solution (Vector Laboratories, Inc., Burlingame, Calif.) containing DAPI.

Statistical Analysis

All statistical analyses were performed by student t-test. Data were considered statistically significant when p value was less than 0.05.

Example 1

Design and Synthesis of Novel Lipids 1-3

Lipids 1 & 2 were synthesized by DCC-coupling of the appropriate tertiary-primary mixed amine intermediates (FIG. 2), prepared conventionally by reacting the corresponding N,N-di-n-alkylamine with N-tert-butyloxycarbonyl protected 2-bromoethylamine in ethyl acetate in the presence of anhydrous potassium carbonate, followed by deprotection and neutralization with $N^\alpha$, -tert-butyloxycarbonyl-$N^\epsilon$-benzyloxycarbonyl-L-Lysine and $N^\alpha$-benzyloxycarbonyl-$N^\epsilon$, -tert-butyloxycarbonyl-L-Lysine derivatives, respectively, followed by benzyloxycarbonyl deprotection with ammonium formate and 10% Pd—C.

Lipid 3 was synthesized by DCC-coupling of the same tertiary-primary mixed amine intermediates with $N^\alpha$, $N^\epsilon$-di-tert-butyloxycarbonyl-L-Lysine derivative, followed by tert-butyloxycarbonyl deprotection with trifloroacetic acid and neutralization. The resulting intermediate amines of the lipids were separately reacted with the desired amount of N,N-di-tert-butyloxycarbonyl thiourea (FIG. 2), prepared by reacting thiourea with 2 equivalents of BOC-anhydride in the presence of 2 equivalents of sodium hydride in anhydrous tetrahydrofuran (Iwanowicz et al. (1993) Synth. Commun. 23:1443-1445), mercuric chloride, and triethylamine in anhydrous N,N-dimethylformamide/dichlromethane under nitrogen atmosphere at 0° C. followed by usual work up. The resulting tertiary amines intermediate (FIG. 2), upon quaternization with excess methyl iodide followed by acid-deprotection and chloride ion exchange chromatography, afforded lipids 1, 2 and 3 (FIG. 2). Structures of all the synthetic intermediates shown in FIG. 2 were confirmed by $^1$H NMR. The presence of highly exchangeable protonated primary amine functions in the head-group regions of the final lipids (1-3), however, caused severe line broadening of the peaks in the NMR spectra, particularly in the range S 3-5 ppm. Thus, the final lipids were characterized by the molecular ion peak in LSIMS. Synthesis and spectral characterization of a representative lipid, lipid 2 and all its intermediates (FIG. 2), are described in the Materials and Methods section. Lipids 1 and 3 were synthesized following essentially the same protocols adopted for the synthesis of lipid 2.

Example 2

In Vitro Gene Delivery with Lipids 1-3

FIG. 4 summarizes the in vitro gene delivery efficacies of lipids 1-3 in transfections of H460 cells in the presence of fetal calf serum. In these in vitro transfection experiments, the cationic liposomes of lipids 1-3 were prepared in combination with an equimolar amount of cholesterol as the co-lipid, and pCMV-Luc plasmid DNA was used as the reporter gene in various lipid/DNA charge ratios of 8:1 to 1:1. The transfection efficiencies of lipid 1 (with a guanidine group at the $N^6$ position) and lipid 3 (with two guanidine groups at the $N^6$ and $N^2$ positions) are comparable to that of DOTAP and Lipofectamine 2000 (FIG. 4). The transfection efficacy of lipid 2 with a guanidine group at $N^2$ position was seriously compromised at lower charge ratios in H460 cells. Interestingly, cholesterol was found to be a more efficacious co-lipid than 1,2-dioleoylsn-glycero-3-phosphoethanolamine (DOPE) (data not shown). These experiments demonstrated the gene delivery activities of the lipids.

Example 3

Lipids 1-3 Exhibit Cytotoxic Activity

Figure 5A:
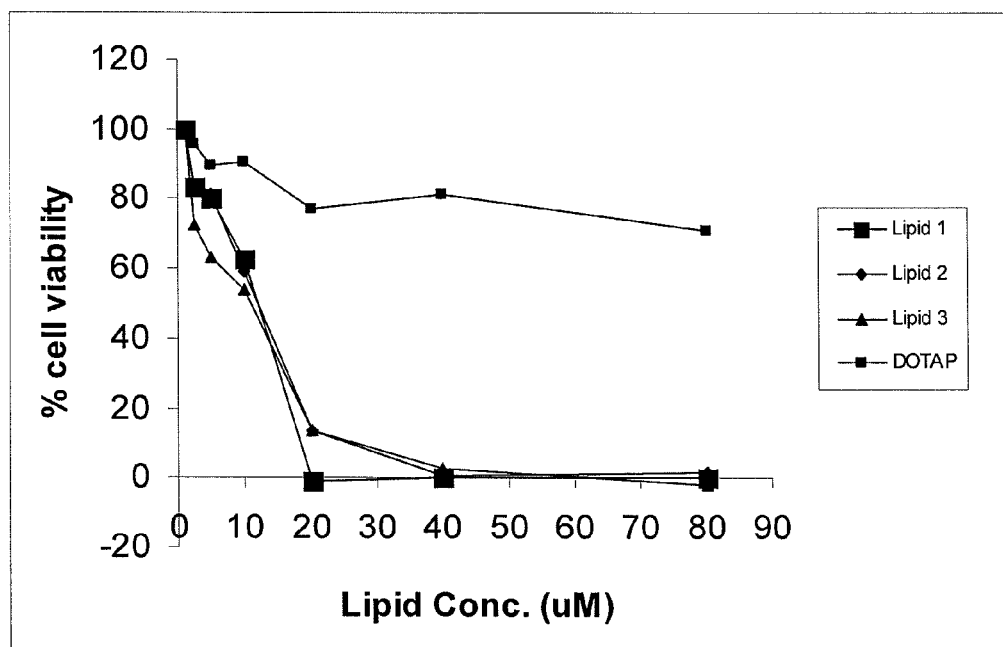
FIGS. 5A and 5B show results of viability assays performed in H460 cells that have been treated with lipids 1-3 or DOTAP for 48 h (FIG. 5A) or pretreated with 10 µM lipid 1-3 or DOTAP, and then challenged with different concentrations of cisplatin one hour later. The cell viability values shown are the averages of triplicate experiments performed on the same day.
Figure 5B:
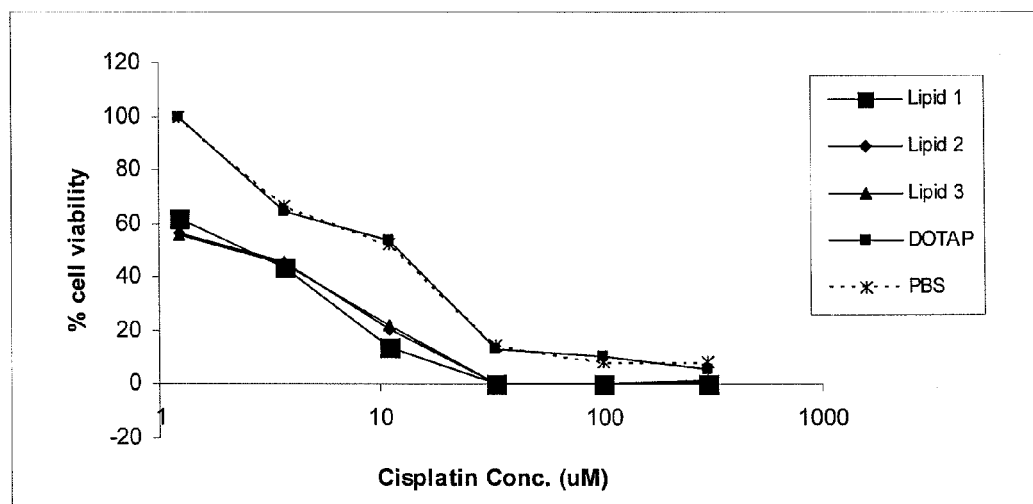

We noticed that the lipids exhibit cytotoxic activity in the transfection experiments and decided to study it in more detail. The cytotoxic effects of the three novel lipids at various concentrations were assessed in H460 cells after exposure to lipids 1-3 and DOTAP for 48 h using the MTT assay (FIG. 5A). In both the cell lines, DOTAP showed slight cytotoxicity at the concentrations examined, whereas lipids 1-3 were more toxic. FIG. 5A shows that the ED50 of lipid 1 and 3 was about 16 μM, whereas that of lipid 2 is about 22 μM in the H460 cell line. We have also tested the cytotoxicity of these lipids in the BL6 cell line and obtained similar ED50 values as in H460 cells (data not shown). Collectively, the cytotoxicity decreased in the order of lipid 1>lipid 3>lipid 2>DOTAP at 20 μM concentration of the corresponding lipids. To assess the chemo-sensitization ability of these lipids to anticancer drugs such as cisplatin, H460 cells were exposed to each of these agents for 48 h, alone and in combination with cisplatin. As shown in FIG. 5B, lipids 1-3 (10 µM), but not DOTAP (10 µM), could sensitize the cells to cisplatin. The IC50 of cisplatin was reduced from about 12 µM to 3.5 µM after treatment with lipids 1-3. These results establish the cytotoxicity of the novel lipids.

Example 4

Lipids 1-3 Inhibit ERK1/2 Activation

Figure 5C:
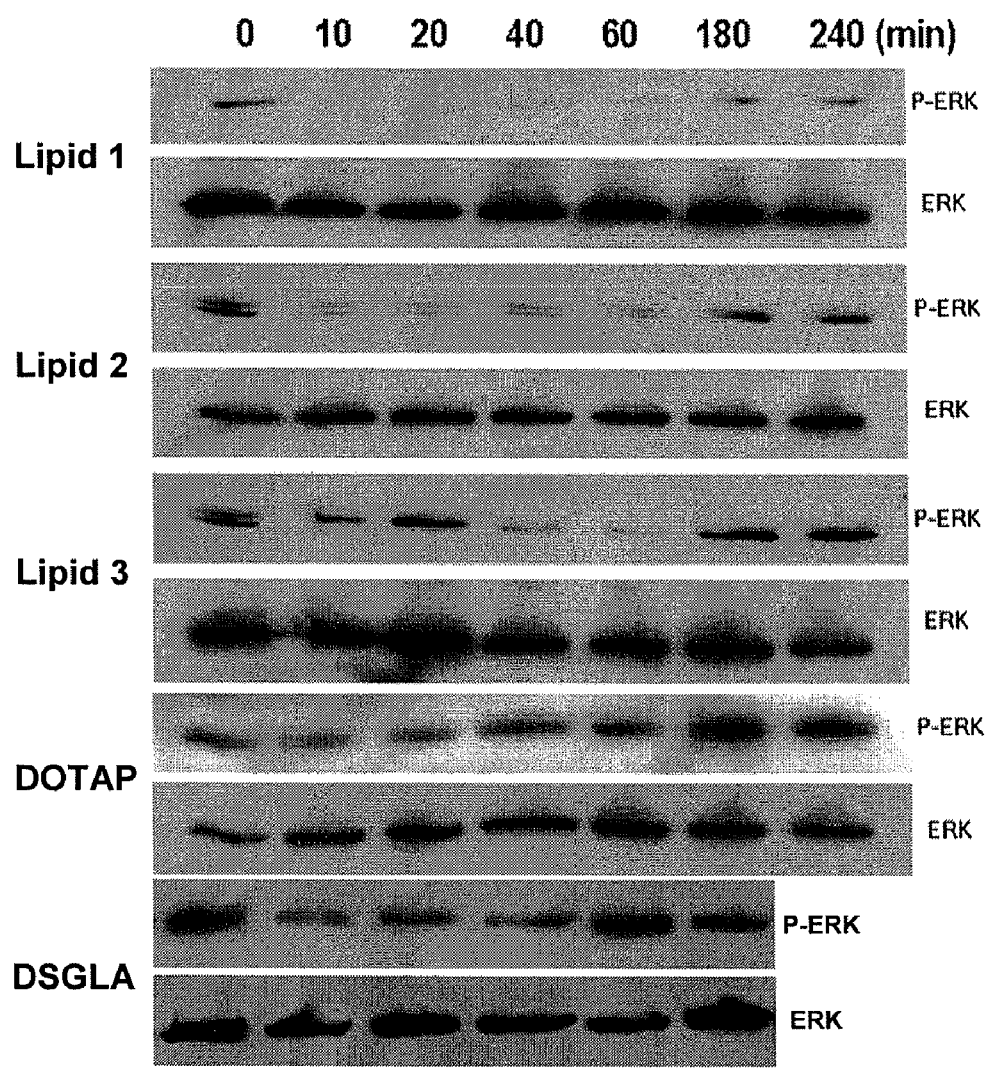
FIG. 5C shows a Western blot measuring phosphorylated extracellular signal-regulated kinase (pERK) and ERK in H460 cells after incubation with 1 µM lipid 1-3 or DOTAP for various times. Data=mean, n=3.

To identify the mechanism responsible for the enhanced cytotoxicity exhibited by the lipids, H460 cells were treated with lipids 1-3 for different time intervals, and ERK 1/2 phosphorylation which leads to the activation of the MAP kinase activity (McCubrey et al. (2007) *Biochim. Biophys. Acta* 1773:1263-1284) was measured by western blot analysis. As shown in FIG. 5C, 1 µof lipids 1-3 alone could decrease ERK1/2 activation. Total ERK1/2 expression remained unperturbed under all conditions. DOTAP at low concentrations (1 µM), however, increased ERK1/2 activation in dendritic cells, consistent with our previous findings (Yan et al. (2007) *Mol. Immunol.* 44:3672-3681). These observations suggest that interruption of the MEK/ERK signaling pathway by lipids 1-3, may play an important functional role in the cytotoxic effect and synergistic induction of cell death when combined with cisplatin treatment.

An analog of lipid 1, DSGLA (both $R_1$ and $R_2$=$C_{18}H_{37}$), was used for further formulation studies due to its higher serum compatibility. Flow cytometry with PI staining showed that the apoptosis rates of H460 cells treated with 10 µM DSGLA and lipid 1 for 3 h were 7.9±2.5% and 10.4±3.0% (n=6, p=0.13), respectively, and were significantly higher than that treated with DOTAP (4.7±0.5%) (n=3, p<0.05). There was no statistically significant difference between the cytotoxicities of DSGLA and lipid 1. In addition, DSGLA alone could also decrease ERK1/2 activation (FIG. 5C).

Example 5

DSGLA-containing Liposomes Efficiently Deliver siRNA to Tumor Cells

Figure 6A:
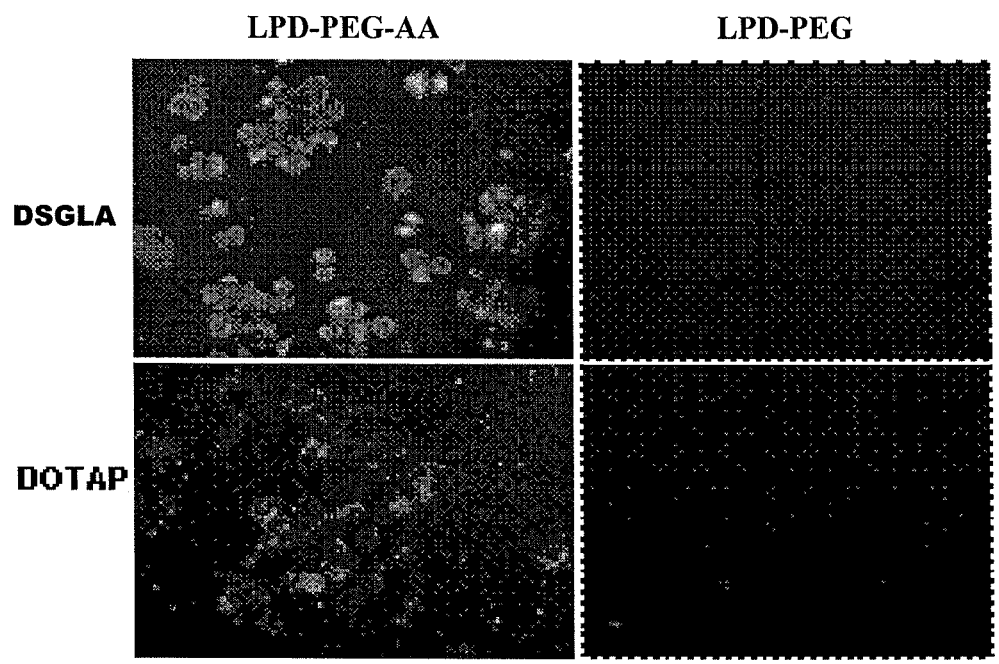
FIG. 6A presents fluorescence photographs of H460 cells after treatment with 5' FAM-labeled siRNA against an irrelevant target in lipid/polycation/DNA-polyethylene glycol (LPD-PEG) or lipid/polycation/DNA-polyethylene glycol-anisamide (LPD-PEG-AA) nanoparticles with (N,N-distearoyl-N-methyl-N-2[N'—(N-6-guanidino-L-lysinyl)] aminoethyl ammonium chloride) DSGLA or DOTAP as the cationic lipid for 4 h. The fluorescent siRNA were extracted from cells and the fluorometric quantitation is presented in FIG. 6B.
Figure 6B:
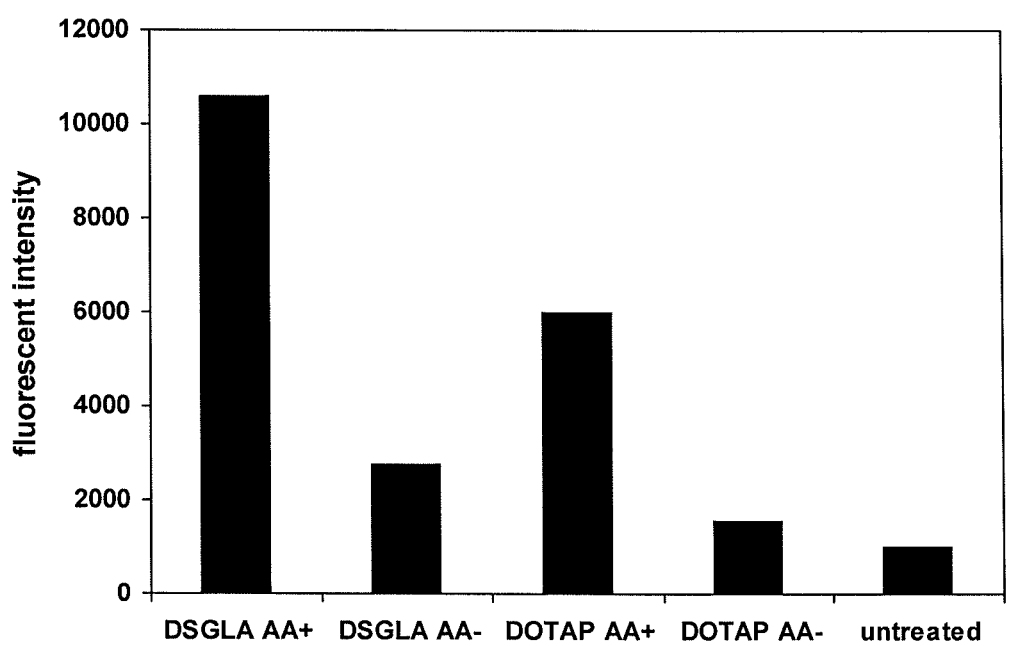
FIG. 6C shows the percentage of propidium iodide-positive cells in those samples of H460 cells treated with control siRNA in different delivery systems for 4 h and stained for propidium iodide.
FIG. 6D shows the flow cytometry analysis of H460 cells treated with control siRNA in different delivery systems for 4 h and stained with annexin V-FITC.

To achieve targeted delivery in cancer gene therapy, we employed LPD, a nonviral vector developed in our lab (Li and Huang (2006) *Mol. Pharm.* 3:579-588) as a nanocarrier for siRNA delivery. We post inserted PEGylated lipids onto our LPD formulation to increase the serum stability. In addition, we also tethered anisamide, a compound that specifically binds to the sigma receptor, to the distal end of PEG as a targeting ligand (Banerjee et al. (2004) *Int. J. Cancer* 112: 693-700). As shown in FIG. 6A, the uptake of fluorescently labeled siRNA was much greater in H460 cells, which express sigma receptor, treated with the formulation prepared with DSGLA than that prepared with DOTAP. Furthermore, the fluorescence signal in the cells treated with LPD-PEG-AA was much stronger than that of cells treated with LPD-PEG. Quantitatively (FIG. 6B), uptake of the fluorescently-labeled siRNA by LPD-PEG-AA containing DSGLA was about two-fold higher than that of LPD-PEG-AA containing DOTAP. FIG. 6B also shows that ligand conjugation increased the delivery efficiency of PEGylated LPD prepared with DSGLA by five-fold. Thus, the results indicate that the LPD-PEG-AA prepared with the novel DSGLA, can efficiently deliver siRNA to the tumor cell and the delivery is highly ligand dependent.

Example 6

DSGLA Induces Apoptosis

Figure 6C:
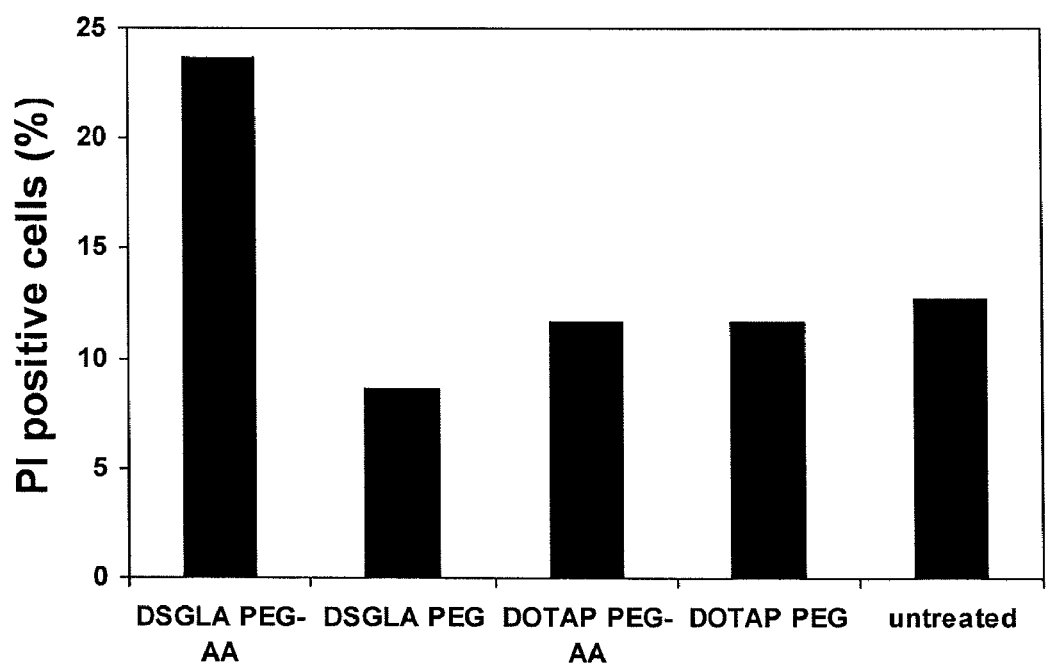
Figure 6D:
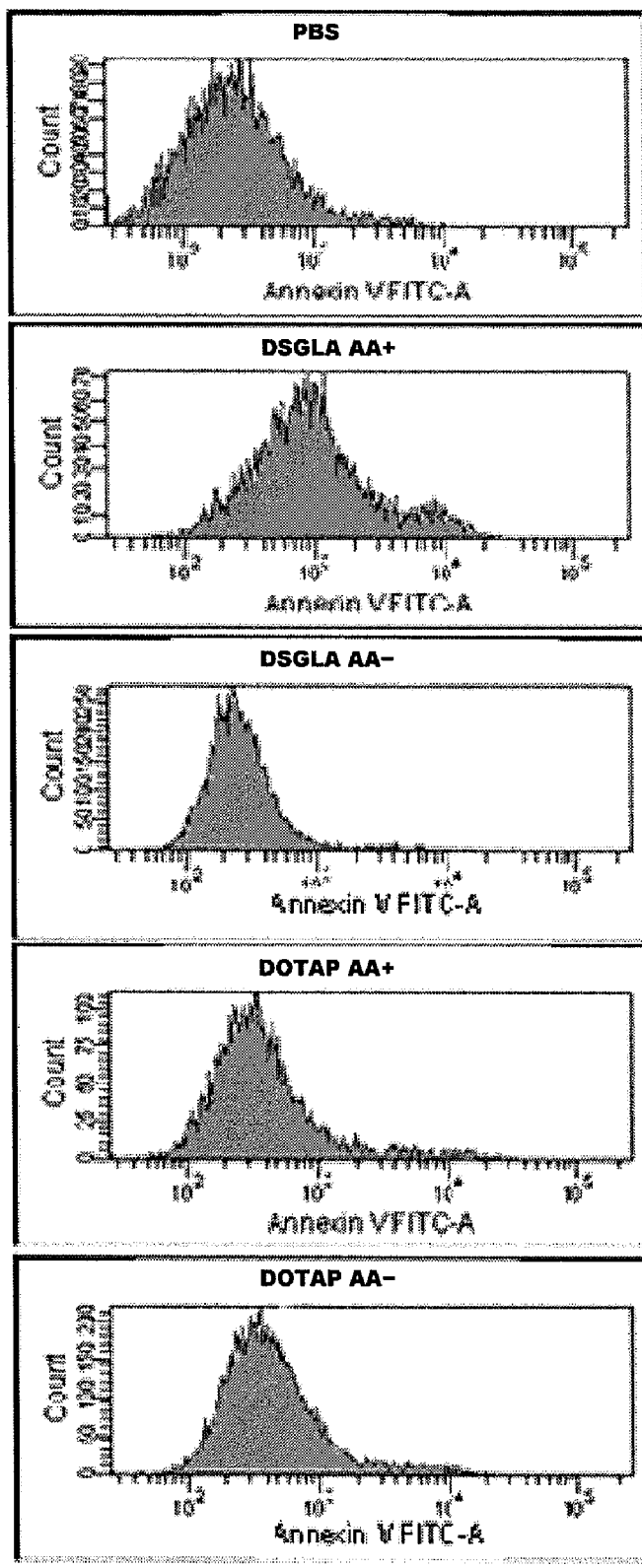

To demonstrate that the cytotoxicity of the cationic lipid is independent of siRNA and highly dependent upon the targeting ligand, DSGLA was formulated with a control siRNA (against an irrelevant target) in LPD-PEG-AA. These results were further compared with the same control siRNA formulated in LPD-PEG-AA containing DOTAP. Flow cytometry was used to analyze uptake of propidium iodide (PI) and the binding of FITC-labeled annexin V with the apoptotic cells. As shown in FIG. 6C, the percentage of PI-positive cells increased when cells were treated with LPD-PEG-AA containing DSGLA, suggesting that the cells were induced to undergo apoptosis. Furthermore, the FITC-Annexin V signal increase was also observed when the cells were treated with LPD-PEG-AA containing DSGLA. No such increase was found when cells are treated with LPD-PEG containing DSGLA or LPD-PEG-AA containing DOTAP. The cells treated with either LPD-PEG-AA or LPD-PEG containing DOTAP showed only a minor increase in FITC-Annexin V (FIG. 6D). The results clearly indicate that the formulation containing DSGLA can more effectively enhance apoptosis than those containing DOTAP, and that the induced cytotoxicity is ligand dependent.

Example 7

Inhibition of EGFR Expression in H460 Cells by DSGLA LPD Compositions

Figure 7:
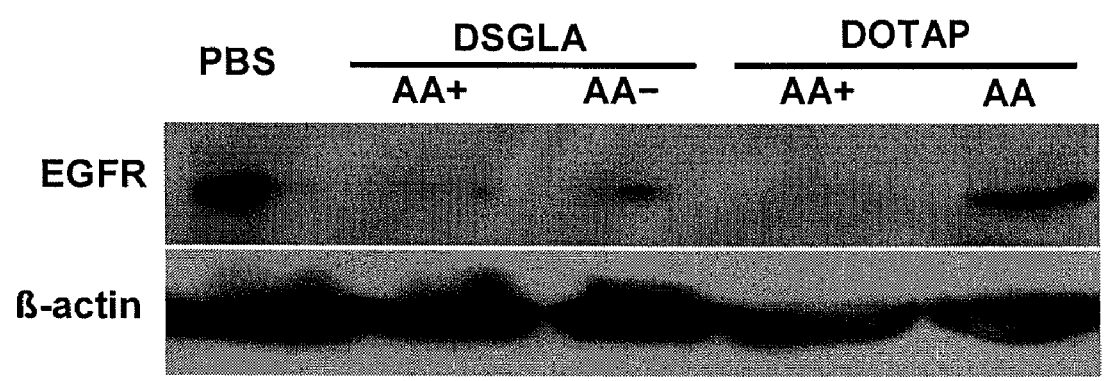
FIG. 7 depicts a Western blot analysis of epidermal growth factor receptor (EGFR) and β-actin in H460 cells treated with LPD-PEG nanoparticles with (AA+) or without (AA−) anisamide ligand. The nanoparticles were prepared with either DOTAP or DSGLA.

To further demonstrate the biological activity of the nanoparticle formulation, siRNA against EGFR was delivered by LPD compositions containing either DSGLA or DOTAP. The resulting effect on EGFR levels was determined by western blot. We compared different compositions in the presence or the absence of AA targeting ligand. Free anti-EGFR siRNA had little effect due to the poor cellular uptake of this negatively charged oligonucleotide (data not shown). H460 cells were treated with anti-EGFR siRNA-containing LPD-PEG-AA prepared with DSGLA or DOTAP. After 72 h, EGFR protein expression was significantly inhibited (FIG. 7). LPD-PEG-AA compositions with either DSGLA or DOTAP were equally efficient at knocking down EGFR expression in H460. Anti-EGFR siRNA-containing LPD-PEG (without AA) prepared with either DSGLA or DOTAP, however, could only slightly down-regulate EGFR. The data indicate that the siRNA could effectively suppress EGFR expression and the silencing activity was formulation-dependent.

Example 8

Synergistic Apoptotic Induction by LPD Comprising DSGLA and Anti-EGFR siRNA

Figure 8A:
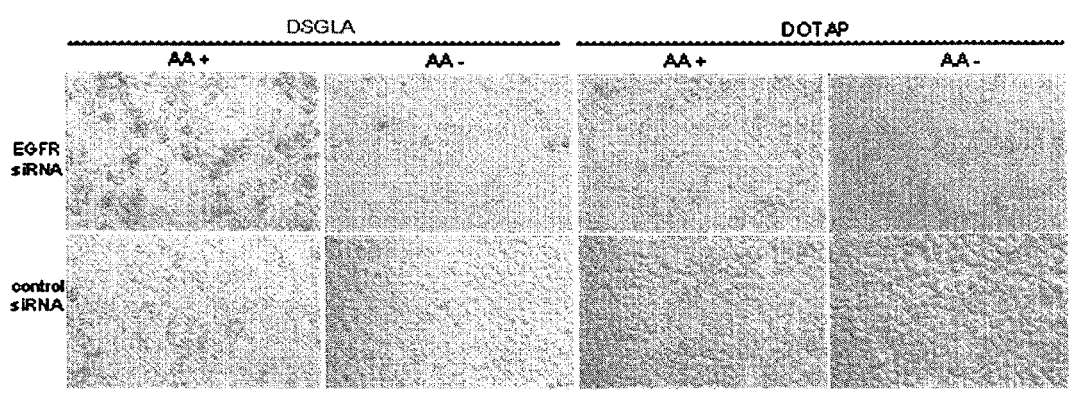
FIG. 8A shows TUNEL staining and FIG. 8B shows the distribution of apoptosis-inducing factor (AIF) in cells treated with different LPD nanoparticles with (AA+) or without (AA−) anisamide ligand for 72 h. Cells with nuclear AIF are shown by arrows. The LPD nanoparticles were prepared with either DOTAP or DSGLA.

The cytotoxic effect of the combination of anti-EGFR siRNA and DSGLA was further studied. To determine whether depletion of EGFR could promote tumor cell death, TUNEL assays were performed at 72 h after treatment with either anti-EGFR or control siRNA formulation. FIG. 8A indicates that about 15±3% of H460 cells treated with EGFR siRNA-containing LPD-PEG-AA prepared with DSGLA undergo apoptosis. This value was higher than the cells treated with EGFR siRNA-containing LPD-PEG (without AA) prepared with DSGLA, EGFR siRNA-containing LPD-PEG-AA prepared with DOTAP, or control siRNA-containing LPD-PEG-AA prepared with DSGLA (FIG. 8A). It was also observed that about 4±1% of H460 cells treated with EGFR siRNA-containing LPD-PEG-AA prepared with DOTAP underwent apoptosis, compared to less than 1% in the control siRNA- and EGFR siRNA-containing LPD-PEG (FIG. 8A). Thus, the cytotoxicity effect mediated by siRNA was sequence-specific and dependent on the efficient delivery by the targeted nanoparticle vector. In addition, about 2.5% H460 cells treated with control siRNA-containing LPD-PEG-AA prepared with DSGLA underwent apoptosis as opposed to less than 1% in the control siRNA-containing LPD-PEG (FIG. 8A). The data indicate that the cytotoxicity of DSGLA was independent of siRNA, but was ligand dependent, consistent with the data shown in FIGS. 6C and 6D. Thus, a synergistic effect between siRNA against EGFR and DSGLA, but not DOTAP, in promoting cellular apoptosis was observed and the synergy was ligand-dependent.

Figure 8B:
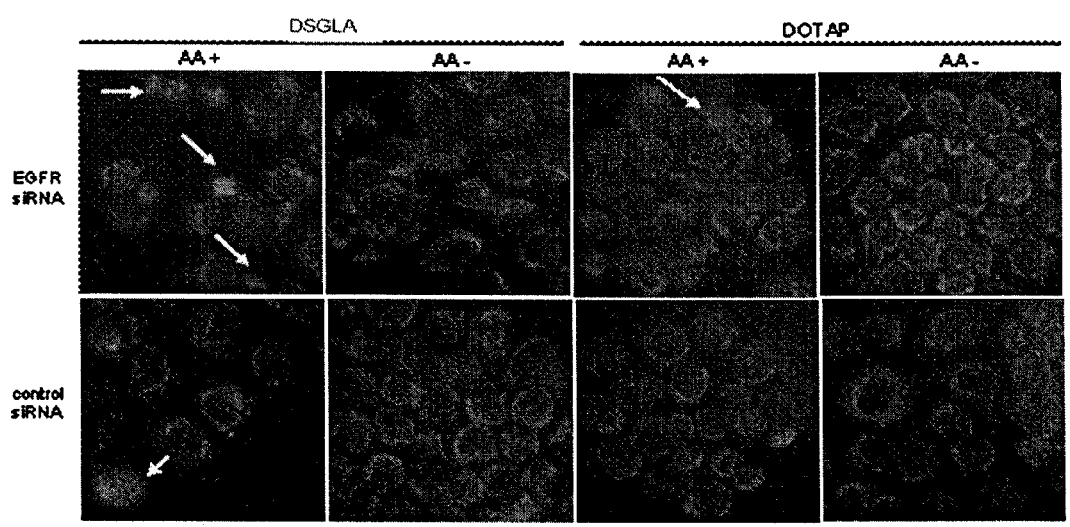

Redistribution of cytochrome c and AIF is an early event in the apoptotic process (Daugas et al. (2000) *FASEB J.* 14:729-739; Fehlberg et al. (2003) *Br. J. Pharmacol.* 139:495-500). To further evaluate the enhancement of H460 cell cytotoxicity by the combination of EGFR siRNA and DSGLA, we examined the involvement of AIF by immunofluorescence microscopy (FIG. 8B). Immunofluorescence detection of AIF in untreated control cells normally yields a punctate cytoplasmic staining pattern with some preference for the perinuclear area, which is a typical pattern for mitochondrial localization (Lorenzo et al. (1999) *Cell Death Differ.* 6:516-524; Loeffler et al. (2001) *FASEB J.* 15:758-767; Modjtahedi et al. (2006) *Trends Cell Biol.* 16:264-272). Cells treated with EGFR siRNA-containing LPD-PEG-AA prepared with DSGLA showed an increased translocation of AIF from the cytoplasm into the nucleus (FIG. 8B). No significant translocation was observed in other treatment groups. The results indicate that EGFR siRNA and DSGLA synergistically promote cell death in H460 and the synergistic effect is ligand-dependent.

Example 9

Synthesis of Mono-arginylated Cationic Lipid DSAA

DSAA, a mono-arginylated cationic lipid, was synthesized by mixing primary-tertiary amine (III) and Boc-protected arginine by the conventional EDCI (N-(3-Dimethylaminopropyl)-N'-ethylcarbodiimide hydrochloride) coupling method. Quaternization with methyl iodide and Boc deprotection of coupled product yields DSAA (VI). The mixed tertiary-primary amine III was prepared by reacting N-Boc-Ethylenediamine with octadecylbromide in ethyl acetate (EtoAc) in the presence of anhydrous potassium carbonate, followed by deprotection and neutralization of the resulting intermediate II. See FIG. 3 for schematic representation of DSAA synthesis.

Example 10

Intracellular Uptake of siRNA Delivered with LPD Formulated with DSAA

Figure 9:
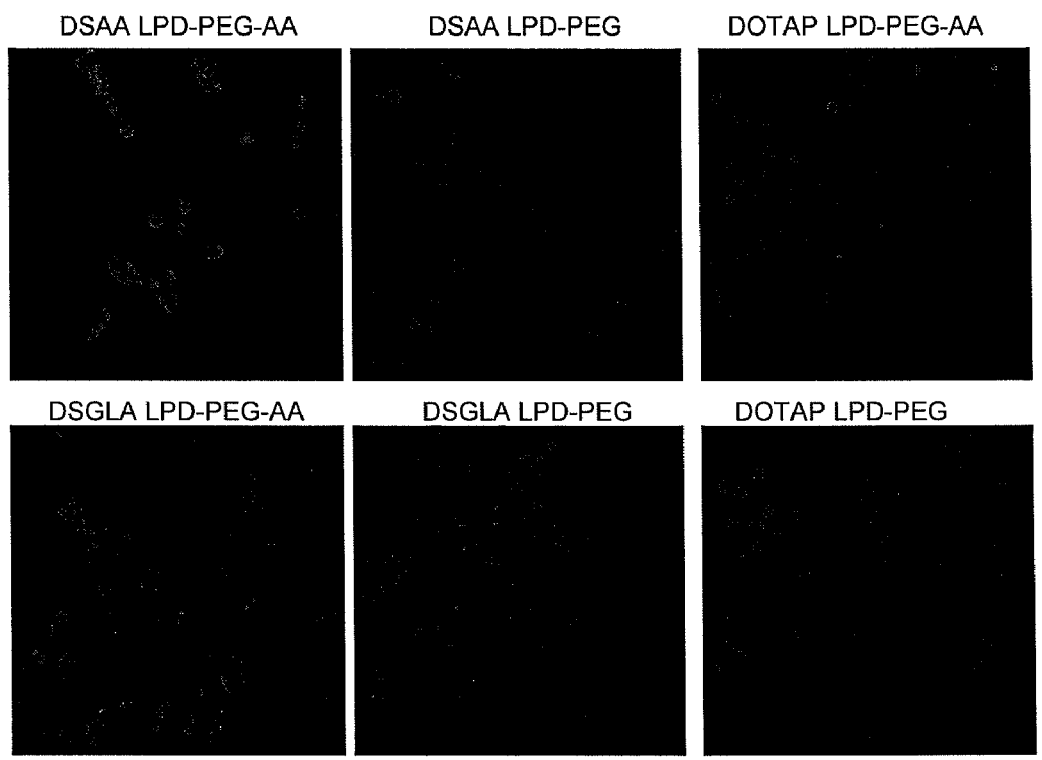
FIG. 9 presents fluorescence photographs of B16F10 cells after a 4 h treatment with 3' CY3-labeled siRNA against an irrelevant target in LPD-PEG or LPD-PEG-AA nanoparticles formulated with the cationic lipid DSAA, DSGLA, or DOTAP.

We post inserted PEGylated lipids onto a LPD formulation, a nonviral vector developed in our lab as a nanocarrier for siRNA delivery, to increase the serum stability. In addition, we also tethered anisamide, a compound that specifically binds to the sigma receptor, to the distal end of PEG as a targeting ligand. As shown in FIG. 9, the uptake of fluorescently-labeled siRNA was much greater in the B16F10 melanoma cells, which express sigma receptor, treated with the formulation prepared with DSAA or DSGLA than that prepared with DOTAP. Furthermore, the fluorescence signal in the cells treated with LPD-PEG-AA was much stronger than that of cells treated with LPD-PEG.

Example 11

In Vitro Luciferase Gene Silencing

Figure 10:
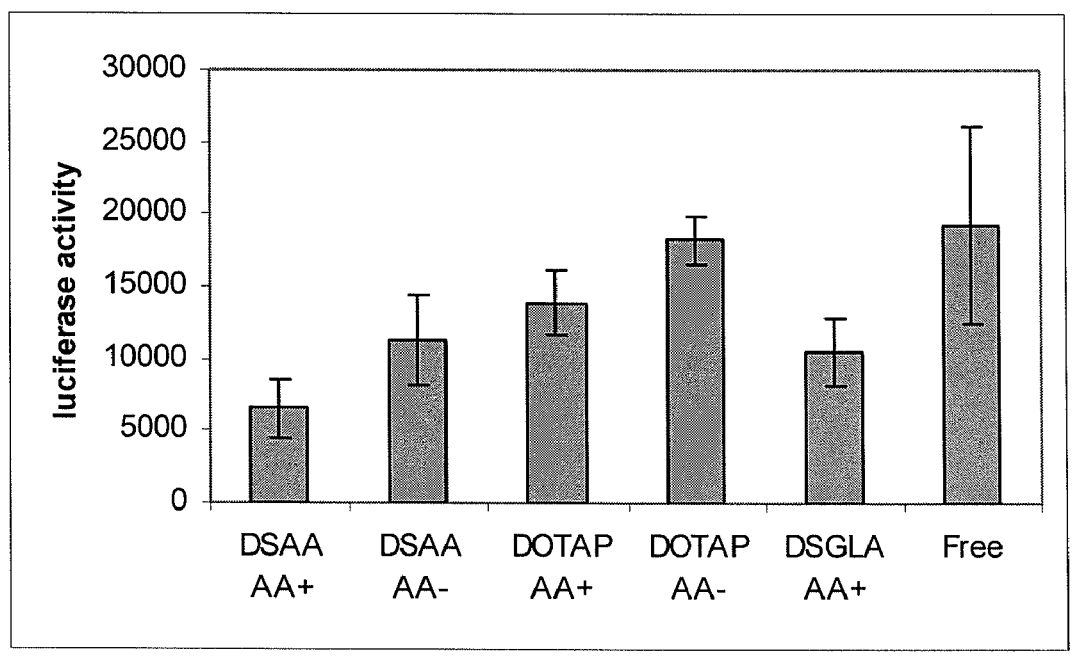
FIG. 10 shows the luciferase reporter activities of B16F10 cells that stably express luciferase and were incubated with different siRNA formulations at 37° C. for 24 h, after which, the luciferase activities of the cells ($2 \times 10^5$) were analyzed. Data=mean±SD (n=5).

We examined the gene silencing effect by siRNA in different compositions. As shown in FIG. 10, the silencing effect of anti-luciferase siRNA was greater in B16F10 cells (that stably express luciferase) treated with the formulation prepared with DSAA than that prepared with DOTAP and even DSGLA. Furthermore, the silencing effect in the cells treated with LPD-PEG-AA was much stronger than that of cells treated with LPD-PEG.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A cationic lipid of Formula (I):

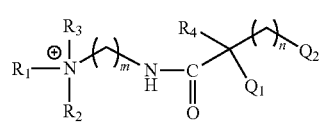

wherein:

m and n are each independently integers from 1 to 8;

$R_1$ and $R_2$ are each independently —$(CH_2)_p$—$CH_3$, wherein p is an integer from 8 to 24;

$R_3$ and $R_4$ are each independently selected from the group consisting of H, alkyl, and substituted alkyl;

$Q_1$ and $Q_2$ are selected from the group consisting of:

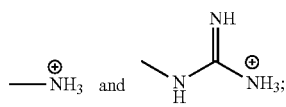

wherein at least Q1 or Q2 is:

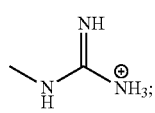

and pharmaceutically acceptable salts thereof.

2. The cationic lipid of claim 1, wherein:

m is 2;

n is 4;

p is 13;

$R_3$ and $R_4$ are each methyl; and the cationic lipid of formula (I) is selected from the group consisting of:

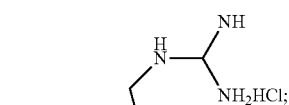

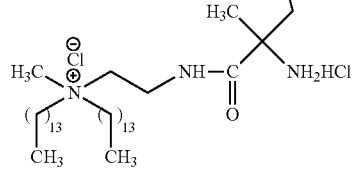

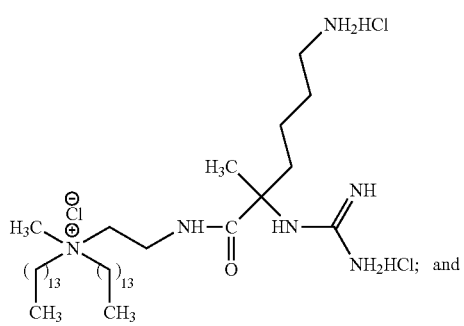

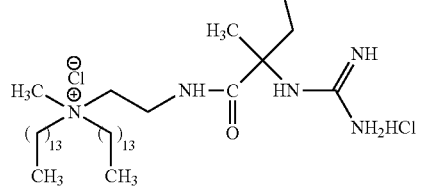

3. The cationic lipid of claim 1, wherein:

m is 2;

n is 3;

p is 17;

$R_3$ is H;

$R_4$ is methyl;

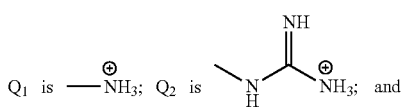

the cationic lipid of formula (I) has the following chemical structure:

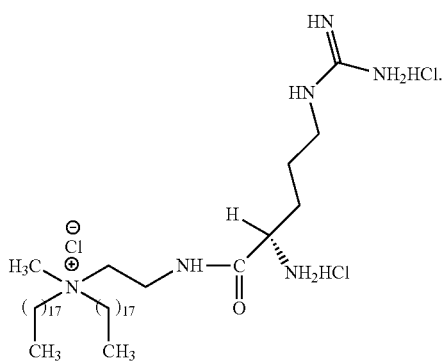

4. The cationic lipid of claim 1, wherein:
m is 2;
n is 4;
p is 17;
$R_3$ and $R_4$ are each methyl;

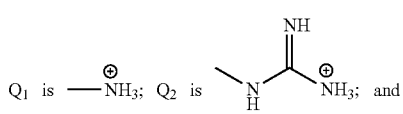

the cationic lipid of formula (I) has the following chemical structure:

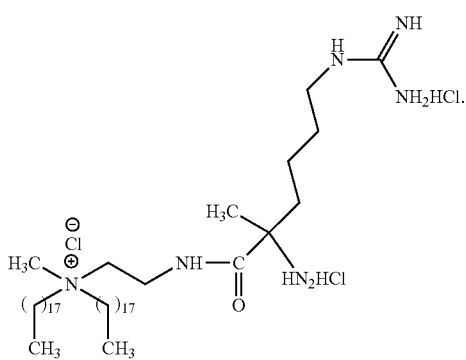

5. A pharmaceutical composition comprising a cationic lipid of claim 1 and a pharmaceutically acceptable carrier.

6. A delivery system comprising a lipid vehicle and a bioactive compound, wherein said lipid vehicle encapsulates said bioactive compound, and wherein said lipid vehicle comprises a cationic lipid according to claim 1.

7. A method for delivering a bioactive compound to a cell, said method comprising contacting said cell with the delivery system according to claim 6.

8. A method for killing a cell, said method comprising contacting said cells with the pharmaceutical composition of claim 5, wherein the pharmaceutical composition has cytotoxic activity.

9. A method for selectively killing a cell, said method comprising contacting said cell with a targeted delivery system, wherein:
(i) said targeted delivery system comprises a lipid vehicle encapsulating a bioactive compound;
(ii) said lipid vehicle comprises a cationic lipid of claim 1;
(iii) said bioactive compound, said cationic lipid, or both have cytotoxic activity; and
(iv) said lipid vehicle comprises an exterior surface comprising a targeting ligand.

10. The method of claim 9, wherein said bioactive compound comprises a cytotoxic bioactive compound.

11. The method of claim 9, wherein said targeting ligand comprises anisamide.

12. A method for treating a cancer in a subject, said method comprising administering to said subject the pharmaceutical composition according to claim 5, wherein said pharmaceutical composition has therapeutic activity against said cancer.

13. The method of claim 12, wherein said cancer is lung cancer.

14. A method for enhancing the cytotoxic activity of a cytotoxic bioactive compound in a subject, said method comprising administering to said subject the pharmaceutical composition of claim 5 and said cytotoxic bioactive compound.

15. A method for making a cytotoxic polynucleotide delivery system comprising a lipid vehicle encapsulating a polycation and a polynucleotide, said method comprising:
a) mixing a polynucleotide and a polycation, thereby forming a polynucleotide/polycation solution; and
b) mixing a lipid vehicle comprising the cationic lipid according to claim 1, wherein said cationic lipid has cytotoxic activity, with said polynucleotide/polycation solution, thereby forming said cytotoxic delivery system.

16. The method of claim 15, wherein said polynucleotide comprises a cytotoxic polynucleotide.

17. The method of claim 15, wherein step b) produces a lipid vehicle comprising a core supported bilayer.

18. The method of claim 15, further comprising post-inserting at least one of a lipid-targeting ligand conjugate and a lipid-PEG conjugate into said lipid vehicle, wherein said post-inserting step is performed after forming said delivery system or said polynucleotide delivery system.

19. The method of claim 18, wherein said lipid-PEG conjugate comprises a 1,2-distearoyl-sn-glycero-S-phosphoethanolamine-N-carboxy-polyethylene glycol$_{2000}$ (DSPE-PEG$_{2000}$).

* * * * *

SEQUENCE LISTING

```
<160> NUMBER OF SEQ ID NOS: 2

<210> SEQ ID NO 1
<211> LENGTH: 21
<212> TYPE: RNA
<213> ORGANISM: Artificial Sequence
<220> FEATURE:
<223> OTHER INFORMATION: siRNA oligonucleotide

<400> SEQUENCE: 1
aacacagugg agcgaauucc u                                              21

<210> SEQ ID NO 2
```

```
<211> LENGTH: 21
<212> TYPE: RNA
<213> ORGANISM: Artificial Sequence
<220> FEATURE:
<223> OTHER INFORMATION: siRNA oligonucleotide

<400> SEQUENCE: 2
aauucuccga acgugucacg u                                              21
```